(12) United States Patent
Suzuki et al.

(10) Patent No.: US 11,160,877 B2
(45) Date of Patent: *Nov. 2, 2021

(54) CAPSULE FOR DRUG DELIVERY SYSTEMS OF TARGETED TISSUE-SPECIFIC DELIVERY TYPE USING CARBOSILANE DENDRIMER

(71) Applicants: Saitama University, Saitama (JP); QUARRYMEN & Co. Inc., Tokyo (JP)

(72) Inventors: Miho Suzuki, Saitama (JP); Ken Hatano, Saitama (JP); Shojiro Yoshida, Saitama (JP); Yasuhiro Yamashita, Tokyo (JP)

(73) Assignees: Saitama University, Saitama (JP); QUARRYMEN & Co. Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/201,076

(22) Filed: Nov. 27, 2018

(65) Prior Publication Data

US 2019/0151467 A1 May 23, 2019

Related U.S. Application Data

(63) Continuation of application No. PCT/JP2017/019735, filed on May 26, 2017.

(30) Foreign Application Priority Data

May 27, 2016 (JP) ................................. 2016-106700

(51) Int. Cl.

| A61K 38/00 | (2006.01) |
|---|---|
| A61K 47/69 | (2017.01) |
| A61K 47/42 | (2017.01) |
| A61K 49/00 | (2006.01) |
| A61K 47/24 | (2006.01) |
| C07K 17/00 | (2006.01) |
| A61K 47/56 | (2017.01) |
| C08G 83/00 | (2006.01) |
| A61K 47/64 | (2017.01) |
| A61K 47/66 | (2017.01) |
| A61K 47/59 | (2017.01) |
| C07K 14/435 | (2006.01) |
| A61P 37/00 | (2006.01) |
| A61P 35/00 | (2006.01) |

(52) U.S. Cl.
CPC .......... *A61K 47/6941* (2017.08); *A61K 47/24* (2013.01); *A61K 47/42* (2013.01); *A61K 47/56* (2017.08); *A61K 47/59* (2017.08); *A61K 47/6425* (2017.08); *A61K 47/66* (2017.08); *A61K 47/6907* (2017.08); *A61K 47/6925* (2017.08); *A61K 47/6931* (2017.08); *A61K 49/00* (2013.01); *A61K 49/0045* (2013.01); *C07K 14/43509* (2013.01); *C07K 14/43595* (2013.01); *C07K 17/00* (2013.01); *C08G 83/003* (2013.01); *A61P 35/00* (2018.01); *A61P 37/00* (2018.01)

(58) Field of Classification Search
None
See application file for complete search history.

(56) References Cited

U.S. PATENT DOCUMENTS

| 8,969,543 B2 * | 3/2015 | Jeong .................. A61K 47/551 536/24.5 |
|---|---|---|
| 2012/0277158 A1 | 11/2012 | Castaigne et al. |
| 2017/0281782 A1 | 10/2017 | Suzuki et al. |

FOREIGN PATENT DOCUMENTS

| EP | 1655022 A1 | 5/2006 | |
|---|---|---|---|
| EP | 1655038 A1 | 5/2006 | |
| JP | 2001-206885 A | 7/2001 | |
| JP | 2005-120068 A | 5/2005 | |
| JP | 2007-001923 A | 1/2007 | |
| JP | 2007-238860 A | 9/2007 | |
| JP | 2009-046413 A | 3/2009 | |
| JP | 2010-112777 A | 5/2010 | |
| JP | 2011-063587 A | 3/2011 | |
| JP | 2013-506697 A | 2/2013 | |
| JP | 2014-073975 A | 4/2014 | |
| JP | 5629888 B2 | 11/2014 | |
| WO | 2005/011632 A1 | 2/2005 | |
| WO | 2005/011633 A1 | 2/2005 | |
| WO | 2011/050178 A2 | 4/2011 | |
| WO | WO-2011050178 A2 * | 4/2011 | ............ A61K 47/62 |
| WO | 2016/084979 A1 | 6/2016 | |

OTHER PUBLICATIONS

Aizawa, Bioorganic & Medicinal Chemistry Letters 22 (2012) 3564-3566 (Year: 2012).*

Yuning Hong et al., "Aggregation-induced emission: phenomenon, mechanism and applications," Chem Commun (Camb). May 13, 2009, pp. 4332-4353.

* cited by examiner

*Primary Examiner* — Satyanarayana R Gudibande

(74) *Attorney, Agent, or Firm* — Locke Lord LLP; James E. Armstrong, IV; Nicholas J. DiCeglie, Jr.

(57) ABSTRACT

The present invention relates to a targeting-type capsule for drug delivery systems. The present invention addresses the problem of providing a capsule for drug delivery systems by utilizing the reactivity of a thiol with an alkyl halide, wherein the capsule comprises a silole-containing carbosilane dendrimer and a labeling protein containing a target recognition site (e.g., green fluorescent protein), can include a biological polymer or another molecule therein, and can deliver the biological polymer or the like selectively into a target cell.

8 Claims, 38 Drawing Sheets

Specification includes a Sequence Listing.

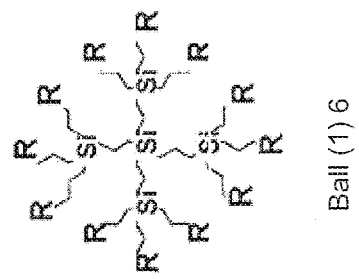
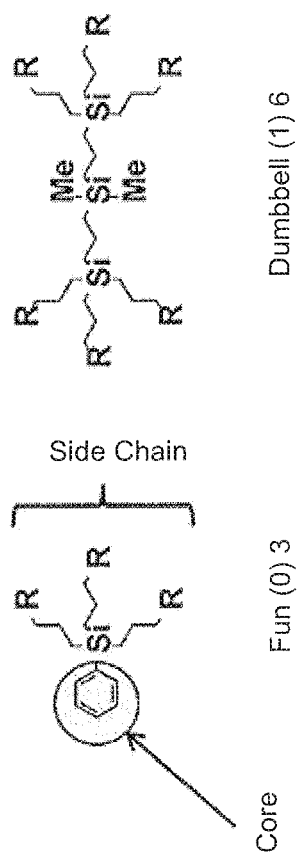

Scheme 2

20 μM GFP

50 μM Silole in PBS

20 μM GFP-Silole

20 μM GFP-Silole + DiI

20 μM GFP-Silole + Oil orange SS

20 μM GFP-Silole + Oil orange SS + IgG-Alexa

····· After PBS wash (×3)
—— 0.45 μm Filtration
– – 0.22 μm Filtration

HepG2 Targeting type 1 Protein(-)(-)
MCF7 Targeting type 1 Protein (-)(-)

HepG2 Targeting type 1 Protein (+)(+)
MCF7 Targeting type 1 Protein(+)(+)

HepG2 Targeting type 1 micelle(-)(-)
MCF7 Targeting type 1 micelle (-)(-)

HepG2 Targeting type 1 micelle(+)(+)
MCF7 Targeting type 1 micelle(+)(+)

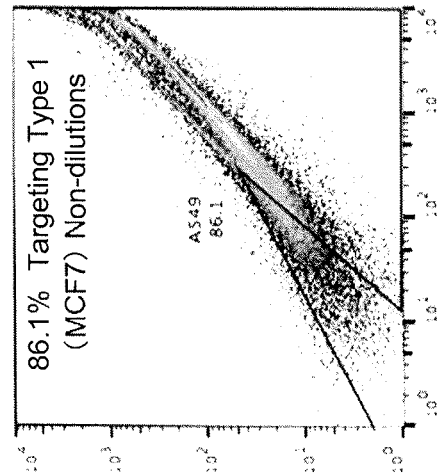
Fig. 14 (C) % Non-Targeting type Non-dilutions
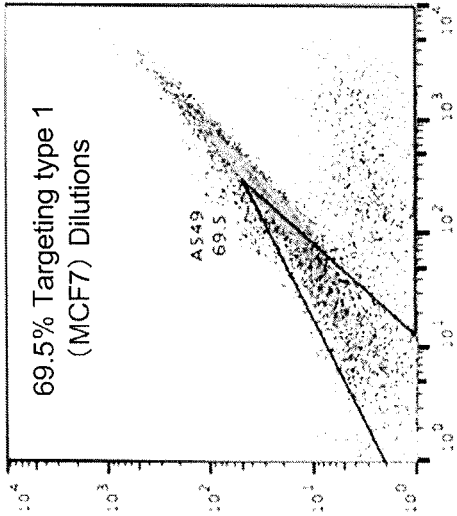
Fig. 14 (E) 86.1% Targeting Type 1 (MCF7) Non-dilutions
Fig. 14 (B) 77.5% Non-targeting type Dilutions
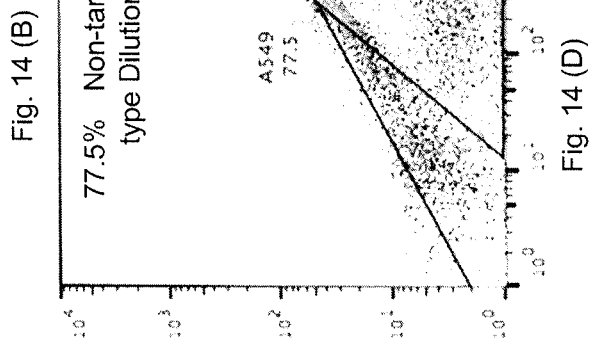
Fig. 14 (D) 69.5% Targeting type 1 (MCF7) Dilutions
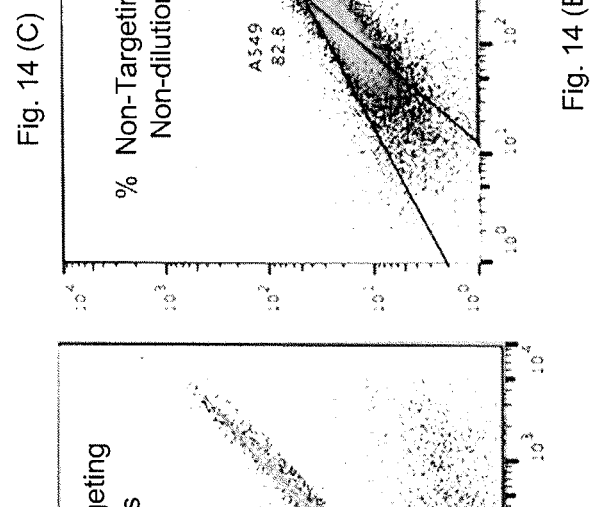
Fig. 14 (A) 5.83% Without Micelle
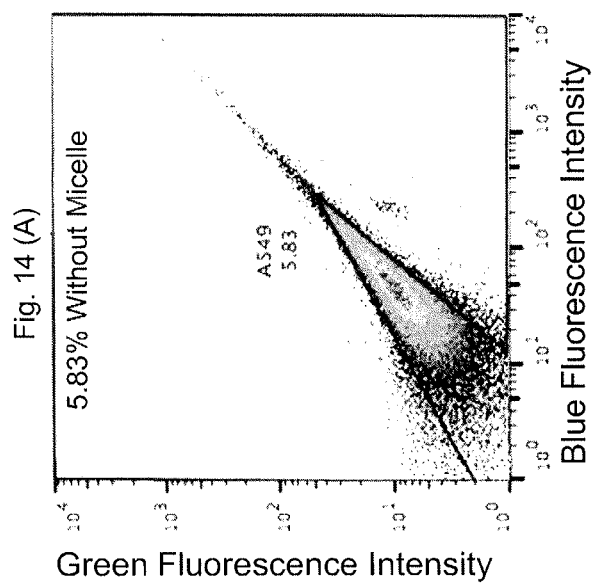
Micelle Incorporation into A549 Cell 24 hours

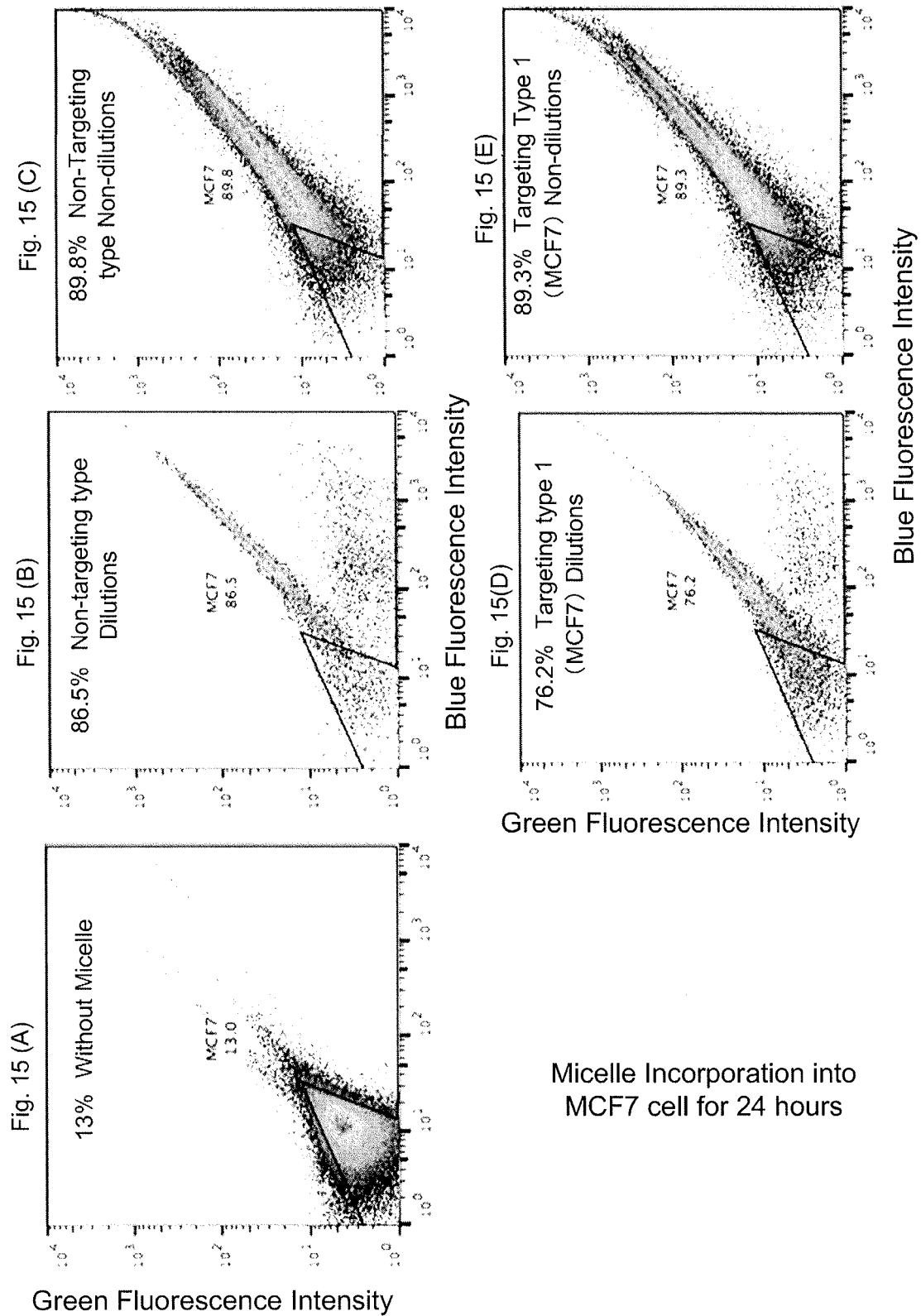

Non-targeting type (50 μM *
150 μL Prepared Micelle)

Non-targeting type' (50 μM *
150 μL Prepared Micelle)

Targeting Type 1 (50 μM *
150 μL Prepared Micelle)

Fig. 20 (A)
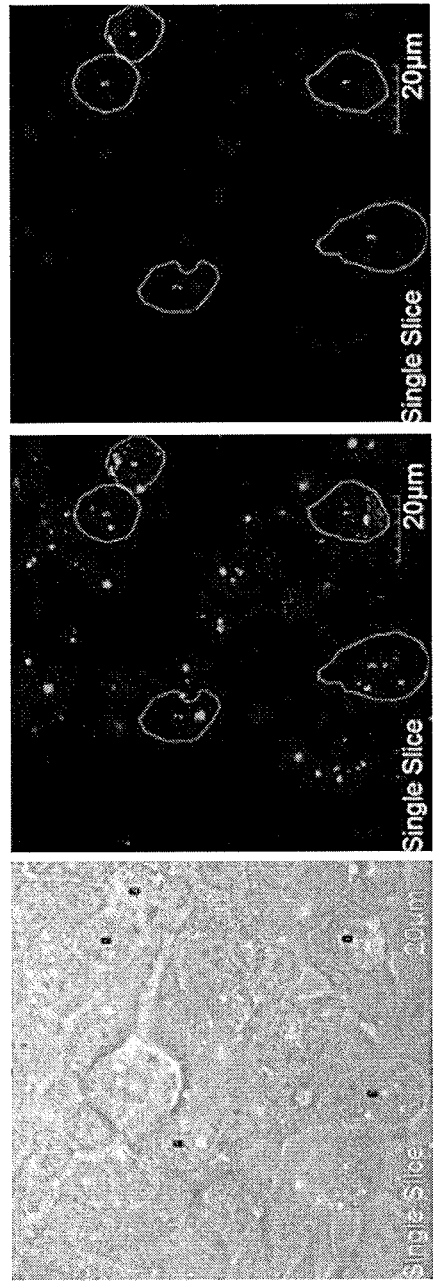 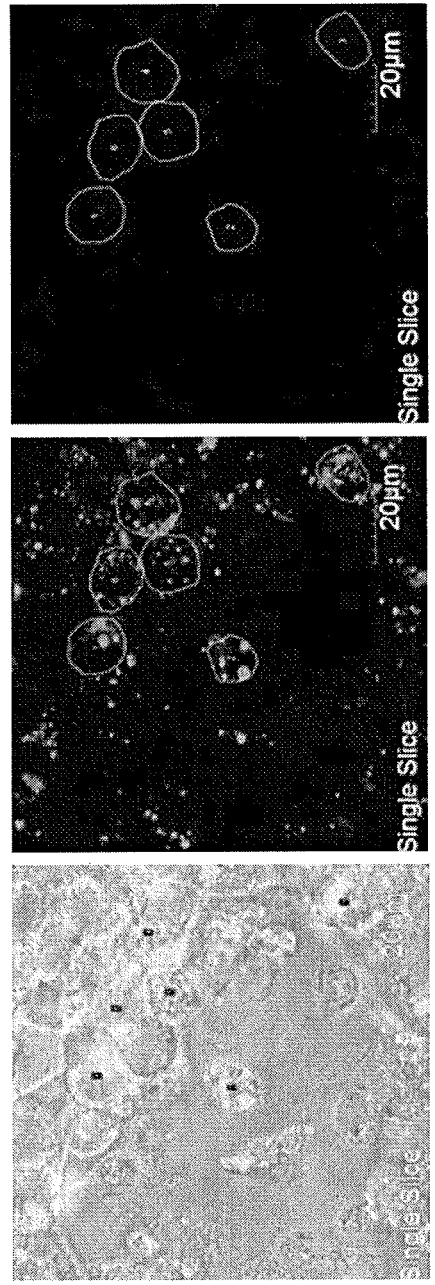

Fig. 20 (B)
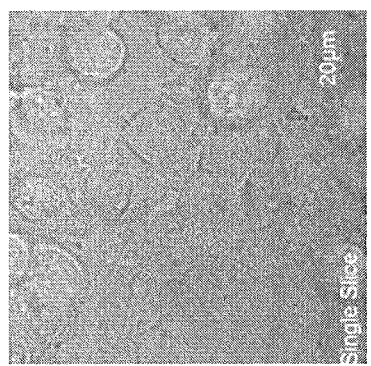
Without Micelle (Poly-d-lysine Coat Dish): 3 hr
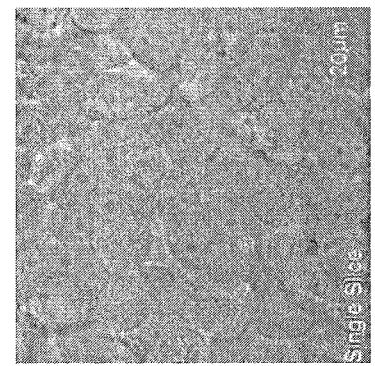
Without Micelle (Poly-d-lysine Coat Dish): 24 hr
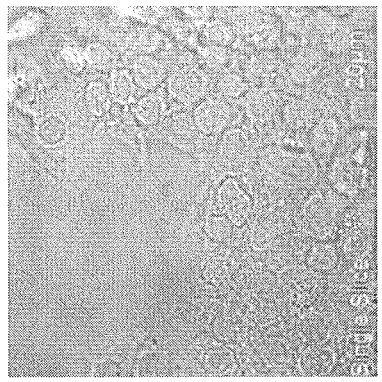
Without Micelle (Collagen Coat Dish)

Fig. 20 (C)
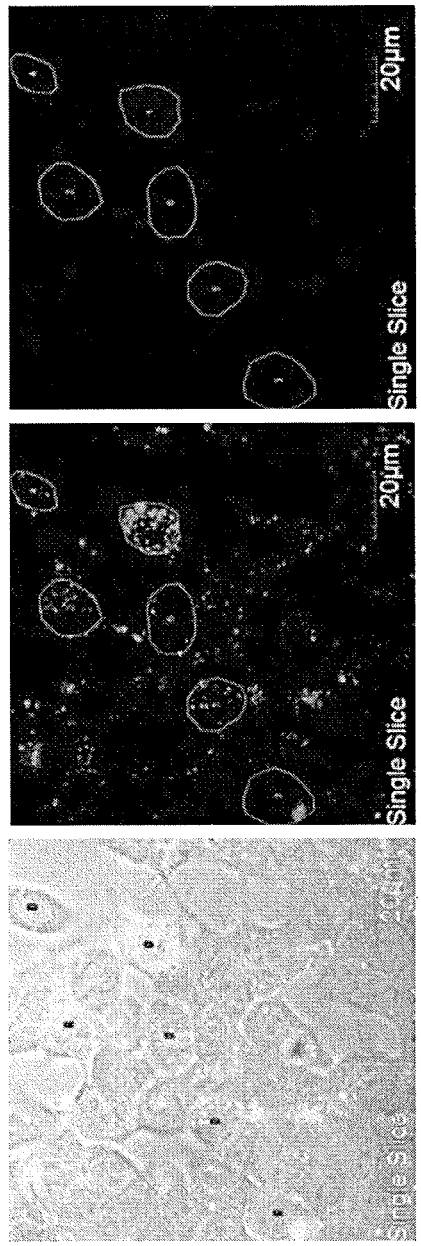
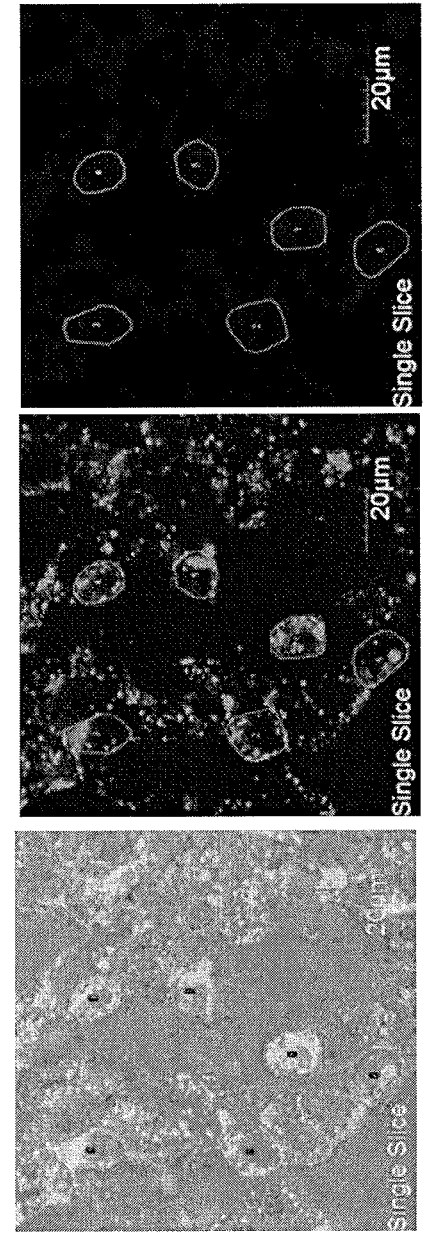

CAPSULE FOR DRUG DELIVERY SYSTEMS OF TARGETED TISSUE-SPECIFIC DELIVERY TYPE USING CARBOSILANE DENDRIMER

TECHNICAL FIELD

The present invention relates to a target tissue-specific delivery type capsule by using carbosilane dendrimer.

BACKGROUND ART

Nowadays, a variety of disease treatment drug have been developed; especially, biopolymers such as antibody, peptide aptamer and nucleic acid have attracted attention as next-generation drugs. The biopolymer should be handled differently from conventional drugs comprising a low molecular weight compound as active ingredient in various points such as quality control in manufacturing processes, storage of pharmaceutical preparations, administration methods, and the like.

In general, amounts of the active ingredients to be delivered to target sites affects to response rate, when a pharmaceutical preparation is administered, depending on both of the disease to be treated and properties of the drug. For example, it is known that the problem that antibody produced depending on a dosage form at the time of administration reduced the efficacy of the administrated drug and therapeutic effect, when the drug comprising the biopolymer as active ingredient is administered.

Therefore, a variety of drug delivery systems (DDS: drug delivery system) have been developed actively as methods for delivering the pharmaceutical preparation to the target site properly. As the carrier for DDS, for example, there are mentioned such as liposome, plastic beads and the like. As the pharmaceutical preparation using such a carrier used for DDS, for example, there are reported those composed of a liposome, to which a ligand specifically binds to a localized molecule in the target site (see patent documents 1 and 2); the liposome or synthetic polymer beads, on which N-acetyl glucosamine or other sugars are exposed (see patent documents 3 and 4), micelles to which antibodies are bound (see patent document 5), and the like.

Also, the carrier utilizing dendrimer having micelle structure is developed (see patent documents 6, 7 and 8). The term, Dendrimer, is a generic word showing dendritic polymer compound has regularly branched structure, of which origin is Greek term "dendra" (trees). Several dendrimer molecules assemble to be spherical form having a nanometer scale space in its inside. Then, since the molecules are incorporated so as to show various functional groups in the space, it has higher flexibility of design. Therefore, currently, various new dendrimers are been developed actively in the field of nanotechnology.

Heretofore, in order to prevent and/or medicate a disease caused by viral or bacterial infections, for example, the carrier utilizing dendrimer has been developed (see patent document 9).

On the other hand, it is known that the dendrimer having silole group shows AIE (aggregation-induced emission) usually to generate fluorescence emission. Here, the term, AIE, which is defined as a phenomenon that the mutually aggregated light-emitting compounds gives high-efficient light emission after they are irradiated by the light with certain wavelength (See, non-patent document 1).

Human body is composed of 60 trillion cells, and these cells incorporate nutrients, extracellular transmitter such as hormones, neurotransmitter and the like to maintain homeostasis in the human body. The endocytosis is referred to as the phenomenon that a variety of extracellular materials is incorporated into the cells.

As the typical endocytosis, there are mentioned such as caveolae endocytosis, lipid raft endocytosis, micropinocytosis, phagocytosis, receptor dependent endocytosis, crathrin-dependent endocytosis, and the like.

It is known that a molecule having large molecular weight is incorporated into the cell through endocytosis. Also, it is known that an aggregable molecule, a conjugate of the dendrimer and a protein, is formed by mixing a silole-containing carbosilane dendrimer, a target protein, for example, green fluorescent protein in an aqueous solution, or mixed solvent of the aqueous solution and an organic solvent.

Then, it is reported that a liposome having the fluorescent protein on outside, which is sometimes referred to as a "vesicle" formation, or micelle formation is formed by supporting the fluorescent protein on the dendrimer; and the vesicle may incorporate a material, for example, a dye, lectin, antibody and the like (see, Patent document 10; it is referred to as the "prior art 1").

PRIOR ART DOCUMENTS

Patent Document

[Patent Document 1] WO 2005/011632
[Patent Document 2] WO 2005/011633
[Patent Document 3] JP 2007-1923 A
[Patent Document 4] JP 2009-46413 A
[Patent Document 5] JP 2014-73975 A
[Patent Document 6] JP 2001-206885 A
[Patent Document 7] JP 2005-120068 A
[Patent Document 8] JP 2007-238860 A
[Patent Document 9] JP 5629888 B
[Patent Document 10] WO2016/084979
[Non-patent Document 1] Chem Commun (Camb). 2009 Aug. 7; (29):4332-53. doi: 101039/b904665h. Epub 2009 May 13

SUMMARY OF THE INVENTION

Problem to be Solved by the Invention

As described above, the study of the carrier for DDS is progressed enthusiastically; however, it is almost impossible to transport the biopolymers effectively without deteriorating their properties.

Also, the biopolymer as an active ingredient is neither delivered to an intestine nor absorbed therefrom, unless the carrier is protected from degradation by gastric acid, strong acid via oral administration. Also, high concentration of the drug may be administrated into blood flow as a bolus injection via intravenous administration (intravenous injection, it is referred to as "i.v."). However, it has other different problems from the decomposition by gastric acid in the oral administration. Therefore, it is difficult to deliver the administered drug to the target site at effective concentration, because of the following reasons: the drug in blood is rapidly and time dependently decreased or excreted into urine, metabolized in a liver, or accumulation in a variety of tissues; and sometimes it stays in the blood without any targeting.

Also, it causes serious side effects when the drug amount delivered to the target site is increased. For example, levodopa, a treatment agent for Parkinson's disease, may pass through blood-brain barrier with very small amount, thereby this gives low response rate. The increased dose of levodopa causes serious side effects, because levodopa, of which targeted site is brain, is decomposed by the enzyme located at the other sites except the brain. By this, actually the treatment with levodopa is stopped. On the other hand, there is another problem that frequent administrations of the drug with small amounts are burden both for patients and healthcare professionals.

Moreover, such carrier requires higher biocompatibility by itself, in addition to have the capability for to incorporating higher molecular weight drug, the biopolymer. If it has lower biocompatibility, it causes a variety of reaction in a living body so that the administration of the carrier itself adversely affects to the living body. Furthermore, it requires another property to maintain the stable structure while it is delivered to the target site to save the incorporated molecules (the active ingredients) and then it releases them quickly from the carrier.

The prior art 1 is an excellent invention from the view point that it may incorporate an active ingredient having large molecular weight, and it has higher biocompatibility by itself. However, it has the problem that it cannot effectively deliver the incorporated model agent to the targeting tissue.

Until now, there is no practical carrier for biopolymers with highly safety, which enables to conduct the target tissue-specific delivery of the incorporated model agent. Therefore, there are strong social needs for such carrier having these characters and properties.

Means for Solving the Problem

The present invention has been completed under such circumstances. The object of the present invention is to provide an endocytosis enhancing agent by using carbosilane dendrimer for drug delivery system; which is stable in living body and enables to specifically deliver the active ingredient to the target tissue, and it further enhances the incorporation of a compound having a variety of molecular weight or biopolymers into the cells.

The present invention has the following aspects. In one aspect of the present invention is an endocytosis enhancing agent: being composed of an aggregable molecule shown in formula (I) comprising a target sequence presented part, it comprises a space for containing an aqueous solvent or organic solvent inside of an aggregates being composed of aggregatable molecule; it is incorporated into a cell through an intracellular transfer pathway selected from the group consisting of caveolae endocytosis, lipid raft endocytosis, micropinocytosis and phagocytosis; wherein said target sequence presented part (TSPP) is composed of a fluorescent protein and a protein or peptide to be used to a target tissue specific delivery; and said space encapsulates a protein having molecular weight of 200,000 or less or peptide dissolved in said aqueous solvent, or a hydrophobic molecule dissolved in said organic solvent.

[Chemical formula 1]

(I)

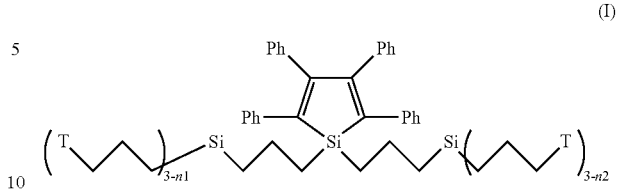

(In the formula, T shows a bromine atom or a target presenting part represented by the following formula (II). Also, both of n1 and n2 represent a number of the target presenting part, and both of (3-n1) and (3-n2) represent the number of bromine atoms. Both of n1 and n2 are an integer from 0 to 3, and all of them do not become 0 simultaneously.).

[Chemical formula 2]

(II)

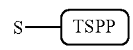

It is preferable that the aggregates has the diameter from 50 to 500 nm size; because it has the most optimal size for giving Enhanced Permeability and Retention Effect into neovascular around the cancer cells in the drug delivery of the anticancer agent.

Herein, the aqueous solution is any one of the buffer selected from the group consisting of saline, phosphate buffered saline, which is sometimes referred to as "PBS"), Tris-HCl buffer, which is sometimes referred to as "Tris-HCl buffer", HEPES buffer, which is sometimes referred to as "HEPES buffer", sodium citrate buffer, which is sometimes referred to as "citrate buffer, and carbonate-bicarbonate buffer, which is sometimes referred to as "carbonate buffer"; because it is preferable that the buffer gives uniform and stable capsule, and it may incorporate a biopolymer such as protein without any denaturation of the protein.

Also, the peptide has both functions to deliver the aggregates to the tissue specifically, and to improve the incorporation the delivered aggregates into the cell of the tissue. The peptide is preferably forms specific biding to the target protein selected from the group consisting of a surface antigen, receptor, gate, transporter and channel, all of them are expressed on the target tissue.

Concretely, the peptide preferably has any one of peptide having the sequence selected from the group consisting of the sequence selected from the group consisting of Seq. Nos. 1 to 3 in the sequence listing.

DMPGTVLPGG (Seq. No. 1 in the sequence listing)

VPTDTDYSGG (Seq. No. 2 in the sequence listing)

DMPGTVLPGG GGGSEGEWQ QQQHQWAKQE (Seq. No. 3 in the sequence listing)

The peptide having a sequence selected from the group consisting of those of Seq. No. 4 to 6 in the sequence listing is preferably used.

MASMTGGQQMGR DMPGTVLPGG MSKGEELFTG VVPILVELDG

DVNGHKFSVS GEGEGDATYG KLTLKFISTT GKLPVPWPTL

-continued

VTTLTYGVQC FSRYPDHMKR HDFFKSAMPE GYVQERTISF

KDDGNYKTRA EVKFEGDTLV NRIELKGIDF KEDGNILGHK

LEYNYNSHNV YITADKQRNG IKANFKTRHN IEDGSVQLAD

HYQQNTPIGD GPVLLPDNHY LSTQSALLKD PNEKRDHMVL

LEFVTAAGSGIT DEVDGT ELYK GG HHHHHH (Seq. No. 4 in the sequence listing)

MASMTGGQQMGR VPTDTDYSGG MSKGEELFTG VVPILVELDG

DVNGHKFSVS GEGEGDATYG KLTLKFISTT GKLPVPWPTL

VTTLTYGVQC FSRYPDHMKR HDFFKSAMPE GYVQERTISF

NDDGNYKTRA EVKFEGDTLV NRIELKGIDF KEDGNILGHK

LEYNYNSHNV YITADKQRNG IKANFKTRHN IEDGSVQLAD

HYQQNTPIGD GPVLLPDNHY LSTQSALLKD PNDKRDHMVL

LEFVTAAGSGIT DEVDGT ELYK GG HHHHHH (Seq. No. 5 in the sequence listing)

MASMTGGQQMGR DMPGTVLPGG GGGSEGEWQQQQHQWAKQE

MSKGEELFTG VVPILVELDG DVNGHKFSVS GEGEGDATYG

KLTLKFISTT GKLPVPWPTL VTTLTYGVQC FSRYPDHMKR

HDFFKSAMPE GYVQERTISF KDDGNYKTRA EVKFEGDTLV

NRIELKGIDF KEDGNILGHK LEYNYNSHNV YITADKQRNG

IKANFKTRHN IEDGSVQLAD HYQQNTPIGD GPVLLPDNHY

LSTQSALLKD PNEKRDHMVL LEFVTAAGSGIT DEVDGTC ELYK GG

HHHHHH (Seq. No. 6 in the sequence listing)

Here, the target tissue is any one of tissue selected from the group consisting of the normal tissue having inflammation, the tissue including the cells having undesirable gene expressions, the tissue composed of the cells having undesirable gene expressions, and the tissue composed of tumor cells.

Here, as the example of the normal tissue having inflammation, the tissue having distinctive feature for autoimmune disease and the like may be mentioned. Also, the example such as the tissue having undesirable gene expressions, the tissue having clear relationship between the disease and single base substitution by SNP analysis and the like are mentioned. As the example for the cells having undesirable gene expressions, the cell derived from the tissue on which undesirable genes are expressed as described above may be mentioned. Furthermore, as the example of the tissues composed of the cancer cells, breast cancer tissue, lung cancer tissue, liver cancer tissue, uterine cervical cancer tissue and the like may be mentioned. As the target recognition site, amino acid sequences shown in Seq. Nos. 1 to 3 in the sequence listing may be mentioned; and as the target presenting part, these shown in Seq. Nos. 7 to 11 in the sequence listing may be mentioned.

Also, the aggregatable molecule shown in the above-mentioned formula (I) is preferably represented any one of the molecule having the structure selected from the group consisting of these shown in the following formulae (III) to (VI). In the following formulae, TSPP means the fluorescent protein having the target sequence presenting part.

[Chemical formula 3]

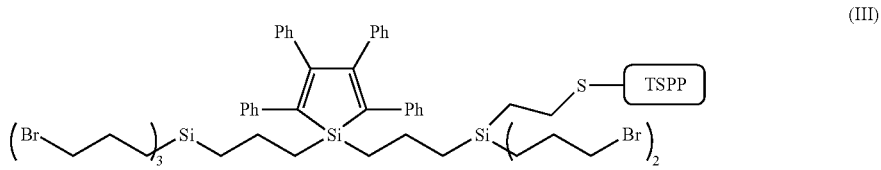

(III)

[Chemical formula 4]

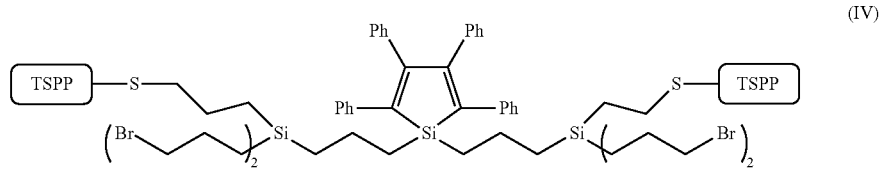

(IV)

[Chemical formula 5]

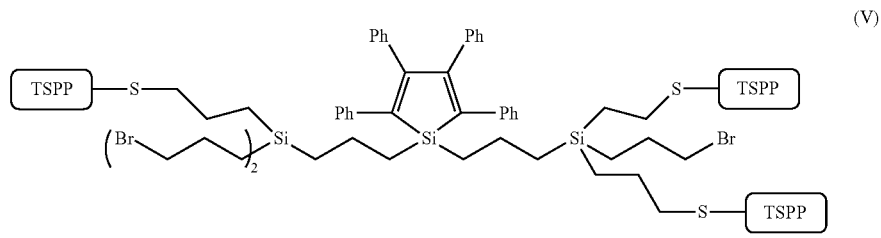

(V)

[Chemical formula 6]

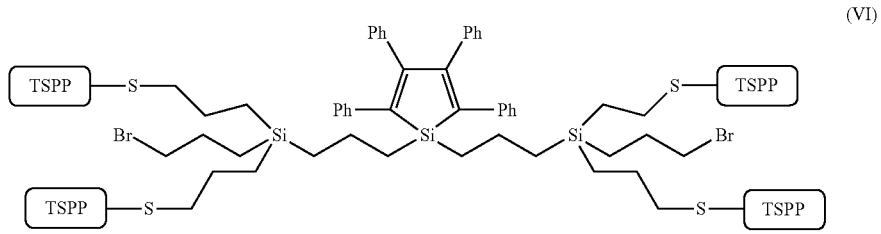

(VI)

Here, the fluorescent protein is preferable that any one of selected from the group consisting of red fluorescent protein, yellow fluorescent protein, blue fluorescent protein, and green fluorescent protein.

Also, the incorporation into the cell is preferably conducted through an intracellular transfer pathway selected from the group consisting of caveolae endocytosis, lipid raft endocytosis, micropinocytosis and phagocytosis.

Advantageous Effect of the Invention

According to the present invention, the endocytosis enhancing agent, which specifically delivers the drugs and the like to the target tissues, and it enhances the incorporation of them into the cells through the particular route, is provided. It enhances the incorporation of the drugs such as biopolymers encapsulated in the agent into the cells in the targeted tissues.

BRIEF DESCRIPTION OF DRAWINGS

FIG. 1(A), FIG. 1(B) and FIG. 1(C) are schematic diagrams showing basic formula of general carbosilane dendrimers.

FIG. 14(A), FIG. 14(B), FIG. 14(C), FIG. 14(D) and FIG. 14(E) are analyzing results by using FACS showing the difference of the incorporation among the micelles, after 24 hours from the contact of A549 cells and the micelle of the present invention.

FIG. 15(A), FIG. 15(B), FIG. 15(C), FIG. 15(D) and FIG. 15(E) are analyzing results by using FACS showing the difference of the incorporation among the micelles, after 24 hours from the contact of MCF7 cells and the micelle of the present invention.

FIG. 20(A) shows fluorescence microscopy images showing the incorporation of the non-targeted type micelle onto the target cells cultured in a collagen coat dish.

FIG. 20(B) shows optical microscopic images showing the status when the cells were cultured without micelles either in a poly-d-lysine coat dish or the collagen coat dish.

FIG. 20(C) shows the fluorescence microscopy images showing the incorporation of the targeted type 1 micelle onto the target cells cultured in a collagen coat dish.

MODE FOR CARRYING OUT THE INVENTION

Hereinbelow, the present invention is explained in detail. The present invention is the endocytosis enhancing agent.

The endocytosis enhancing agent of the present invention is composed of an aggregable molecule shown in formula (I) comprising a target sequence presented part, and it encapsulates biopolymers. Said endocytosis enhancing agent comprises—a1) a space for containing an aqueous solvent or organic solvent inside of an aggregates being composed of aggregatable molecule, and a2) it is incorporated into a cell through an intracellular transfer pathway selected from the group consisting of caveolae endocytosis, lipid raft endocytosis, micropinocytosis and phagocytosis.

[Chemical formula 7]

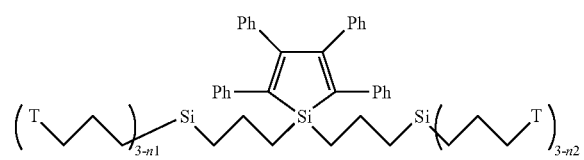

(I)

In the formula, T represents the bromine atom or the target sequence presenting part shown in the following chemical formula (II). Also, both n1 and n2 represent the number of the target sequence presenting part, and both (3-n1) and (3-n2) represent the number of the bromine atom. Both n1 and n2 are integers from 0 to 3, and they do not become simultaneously 0.

[Chemical formula 8]

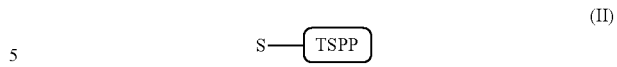

(II)

The target sequence presented part (TSPP) is composed of the fluorescent protein and the protein or peptide for the target tissue specific delivery; the space encapsulates the protein having molecular weight of 200,000 or less or peptide dissolved in said aqueous solvent, or a hydrophobic molecule dissolved in said organic solvent. A plurality of the molecule may be simultaneously encapsulated, or the protein and the nucleic acid and/or the hydrophobic molecule may be simultaneously encapsulated.

As described above, the carbosilane dendrimer used in the present invention, hereinafter, it is sometimes referred to as "silole dendrimer", is preferable the compound shown in the chemical formula (I) by the following reasons: it allows to comprise both of the aggregatable property and the targeted sequence presenting part described later; and it comprises the target sequence presenting part (TSPP) which is schematically shown in the chemical formula (II) and necessary for enhancing the incorporation of the encapsulated drugs through the endocytosis.

Figure 2:
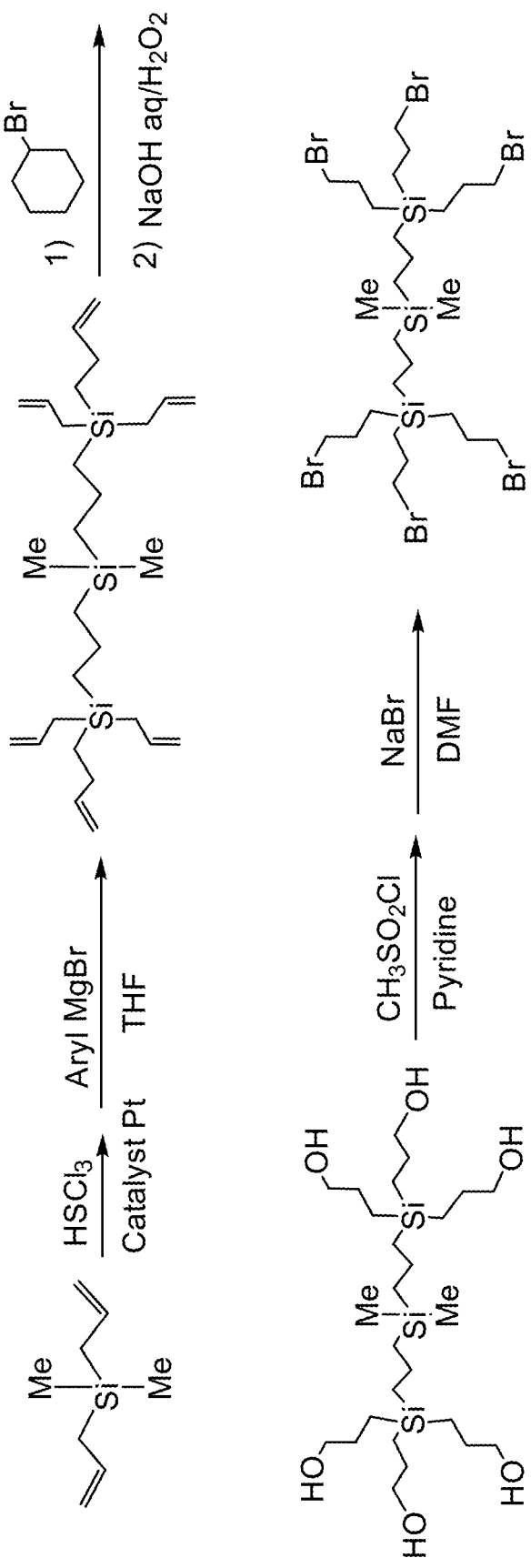
FIG. 2 is the figure showing synthesis scheme of dimethyl dumbbell (1) 6-Br from dimethylsilane.

FIGS. 1A to 1C show a general structure of carbosilane dendrimer. A compound shown in FIG. 1A is referred to as fun (0)3, which has a benzene ring as a core marked with a circle. The compound shown in FIG. 1B is referred to as dumbbell (1)6, which has two fun (0)3 molecules connected with silane having 2 methyl substitute (Me-Si-Me) instead of the core. The compound shown in FIG. 1C is referred to as ball (1)6, wherein the molecule, fun (0)3 without the core forms the ball shape by being replaced methyl in Me—Si—Me of the dumbbell to $(Si)_5$ (See, FIG. 2).

In contrast, the structure of carbosilane dendrimer of the present invention has completely different structure shown in both of the formula (I) and (II) compared with those of the conventional carbosilane dendrimers, and one of bromine atom binding to the end of the molecule pertains to form the bond with targeted sequence presenting part. Here, the targeted sequence presenting part is shown in schematically shown in the formula (II); and is a component of the target presenting part for tissue specific delivery, and it is composed of the fluorescent protein, and peptide or protein for enhancing the incorporation of the encapsulated drug into the cells of the targeted tissue to which the it is delivered.

Also, the protein or the peptide has the target sequence shown in the Seq. Nos. 1 to 3 in the sequence listing from the view point that it enables to conduct specific delivery of the drug for DDS composed of the dendrimer.

Also, the protein as the target sequence has solely the reactive thiol group, and it is preferable that the thiol group locates outside of folded protein, namely, the surface of the protein.

Since the thiol groups react with the halogen atoms contained in the dendrimers to play a role to bind the protein and the dendrimer, the thiol groups located in side of the folded protein may not be involved in forming the bond. Here, the "protein having thiol groups" comprises the protein originally having thiol groups, that having newly introduced thiol groups by using the genetic engineering technique and the like, and that having the thiol groups resulting from the reduction of cysteine in the cysteine including protein.

The positions of the thiol group in the protein are not particularly limited. However, it is sometimes preferable that the thiol groups are positioned in the specific region on the protein. Furthermore, it sometimes enables to control emission properties of the shell. Note that cysteine "included in in the protein" may be that inserted into the predetermined position by using the gene-engineering technique such as for replacing the existing arbitrary amino acid with cysteine, that for inserting it at the predetermined position and the like. It is easily conducted for the person skilled in the art to introduce cysteine residue at the desirable position in the protein by using the known gene engineering method such as the site-directed mutagenesis and the like.

The protein having the targeted recognition site which composes the targeted sequence presented part is not limited as long as it has mutually association properties, hereinbelow; it is sometimes referred to as "association properties". However, the fluorescent protein emitting colors other than green described in below is preferably used. Those fluorescent proteins emitting fluorescence other than green are sometimes collectively referred to as "GFP". Association of such fluorescent proteins to the carbosilane dendrimer emits strong fluorescence, and it leads to easy detection of the association state.

As GFPs used in the present invention, there are mentioned, for example, GFP shown as Seq. No. 7 in the sequence listing, GFP shown as Seq. No. 8, BFP shown as Seq. No. 9 in the sequence listing which is blue fluorescent protein, YFP shown as Seq. No. 10 in the sequence listing and the like, and also CFP, RFP and other variant GFPs provided from Clontech Laboratories, Inc., and the like. Besides these, the fluorescent protein derived from Discosoma shown as Seq. No. 5 in the sequence listing and the like may be used. However, GFP shown as Seq. No. 7 in the sequence listing is preferably used, because it has strong fluorescence intensity, and also it is easy handled. Furthermore, it is assumed that commercially available Azami-Green and other color variants, provided by Medical & Biological laboratories Co. Ltd., are also preferably used, because of their structural properties.

Also, such GFPs may be prepared by using known methods, for example, referring to Biochem. Biophys. Acta 1679 (2004) 222-229; Biochem. Biophys. Res. Commun. 330 (2005) 454-460, and the like. Also, GFPs may be used those produced by outsourcing to the protein manufacturing company.

The aggregatable carrier of the present invention is formed by using the molecules containing functional groups causing AIE effect such as silole and the like as a framework and associative proteins such as fluorescent protein as the targeted sequence presented part. In the micelle formed by using them, aggregated siloles also emit fluorescence. As a result, fluorescence resonance energy transfer (FRET: Fluorescence resonance energy transfer) is occurred between the associated fluorescence proteins and gathered siloles, and it makes the fluorescence strong. When the micelle is collapsed, FRET disappears.

Therefore, when the micelle manufactured by using the present invention is used as the carrier for the drug delivery, of which status in vivo may be monitored by using the change of FRET as an index. Moreover, such monitoring enables to trace the location of the carrier and its status possible.

In order to cause FRET between the fluorescent protein and the silole dendrimer, fixed position of the fluorescent protein on the silole dendrimer is important. The person skilled in the art may easily determine the position on the protein onto which binds the dendrimer by a preliminary experiment and the like. When GFP is used as the fluorescent protein, it is preferable to bind a loop region which is contiguous to one region among N-terminal region, C-terminal region, N-terminal region and C-terminal region. It is preferable that the amino acid such as cysteine having thiol group exists in the region.

Here, the binding in the "N-terminal region" means that the protruding moiety from the core site, such as being composed of about 10 amino acids positioned close to the end of N-terminal, is binding to the silole dendrimer. As the same as that described above, in C-terminal, the protruding moiety from the core site, such as being composed of 10 amino acids positioned close to the end of N-terminal, is binding to the silole dendrimer.

A position of halogen group carried on the silole dendrimer of the present invention is not limited particularly. However, it is preferable to located on the side chain of the silole dendrimer. More preferably, it is located at the side chain terminal, which is the most distant position from the silole group, as the formula (I) shows.

As described above, the silole dendrimer used in the method of the present invention is preferable the compound shown in formula (I). The silole core 2 (1, 1-diaryl-2, 3, 4, 5-tetra phenyl silole) may be synthesized, for example, from 1, 2-diphenyl acetylene via the known intermediate 18 as shown in the scheme 2 via the known intermediate 18.

Next, the silole core dendrimer 3 is obtained through hydrosilation of 2 with trichlorosilane using $H_2PtCl_6 \cdot 6H_2O$ as a catalyst, and subsequent Grignard reaction by using aryl magnesium bromide. The silole core dendrimer 3 obtained is treated with dichlorohexyl borane and then subjected to hydrolyzation with hydrogen peroxide in alkaline aqueous solution to obtain hexahydroxy derivative 4. Subsequently, the hexahydroxy derivative is subjected to O-mesylation to replace with bromine anion to obtain the compound 5 (Tetrahedron Lett., 2007 48:4365-4368).

[Chemical formula 9]

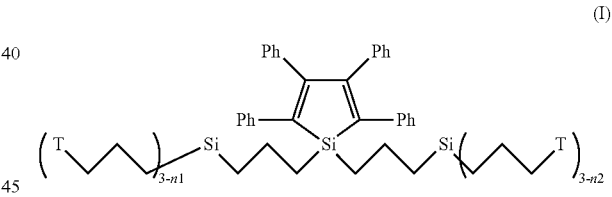

In the formula, T shows the bromine atom or the target presenting part shown in the formula (II). Both of n1 and n2 show the number of the target presenting part, and both of (3-n1) and (3-n2) show that of bromine number. Both of n1 and n2 are 0 to 3, and they are not become simultaneously 0.

The protein having the targeted recognition site which composes the targeted sequence presented part is not limited as long as it has association properties. However, the protein is preferably any one of the fluorescent protein selected from the group consisting of the white fluorescent protein, the red fluorescent protein, the yellow fluorescent protein, the blue fluorescent protein and the green fluorescent protein.

It is because that they are easily purchased, and have high intensity fluorescence so that they generate FRET to give strong fluorescence. Here, the blue fluorescent protein includes any of those emits blue or cyan fluorescence.

The aggregatable molecule of the invention is prepared by mixing the protein having thiol group, which is targeted sequence presented part, and the dendrimer compound having halogen group in the side chain shown in formula (I), and then the mixture is incubated to react the thiol group of the protein and the halogen group of the dendrimer compound thereby binding the protein to the dendrimer compound. At this time, it is desirable to previously treat the protein with a reducing agent such as DTT to keep —SH group in non-oxidized condition. Scheme 1 shows the reaction for incorporating one GFP molecule by using the reaction.

Scheme 1

[Chemical formula 10]

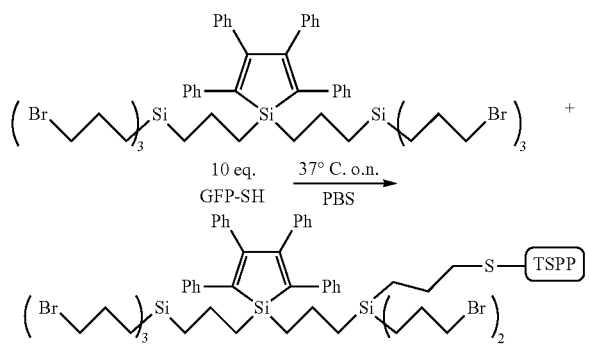

For example, the reaction shown in the scheme 1 may be conducted in a proper solvent, for example, an aqueous solvent such as PBS, saline, and the like. The reaction condition in this case is depending on the proteins used. The reaction temperature may be under the denaturation temperature of the protein used, for example, between 0° C. and 50° C., preferably between 30° C. and 45° C., and more preferably about 37° C. When GFP is used, the reactivity may be temperature-dependently improved up to 42° C. Therefore, it is preferable to use GFP for preparing the aggregatable carrier material for DDS.

Also, the reaction time varies depending on the reaction temperature. However, for example, it is from 1 to 24 hours, preferably from 10 to 19 hours, and more preferably about from 15 to 18 hours. It is because that the protein having thiol group used is bound to the silole dendrimer to form the micelle during such reaction time, and the liposome or the micelle is formed.

That is, as protein-dendrimer complex is formed, the micelle of which outside is composed of the protein, which is the hydrophilic moiety, and of which inside is composed of the core part of dendrimer, which is the hydrophobic moiety. That is, it is considered that the liposome or the micelle is formed by the driving force generated from the association of the protein in the binding of the associative protein to the side chain of the dendrimer.

Here, at least one or more proteins are replaced with the halogen atom at the end of side chain to bind to the silole dendrimer described above. Therefore, the aggregatable carrier material for the drug delivery system obtained through the reaction is a mixture of the conjugates shown in the chemical formulae (III) to (VI).

When the protein having thiol group is the fluorescent protein, the mixing ratio of such protein and dendrimer (molar ratio) may be, for example, that the dendrimer is from 1 to 20, when the protein is 1; preferably from 15 to 1:15, and more preferably about from 1:10. Note that the maximal ratio is varied depending on the concentration.

Also, when the reaction is conducted, it is preferable to incorporate an amino acid sequence, which becomes the targeted recognition site, into the protein as the targeted sequence presented part, because it enables to realize the effective delivery in the DDS described later. Such incorporations of the targeted recognition site may be conveniently conducted by using Inverse PCR. The plasmid coding thus prepared variant is incorporated into *E. coli* to express thereof, and then, it enables to obtain the variant protein easily for the aggregatable molecule for DDS.

The incorporation of the targeted recognition site enables specific delivery of the micelle being composed of the aggregatable molecule for drug delivery system of the present invention to the normal tissue having inflammation, the tissue having undesirable gene expressions, the tissue composed of tumor cells and the like.

The endocytosis agent having the structure is produced and it encapsulates desirable agents. Thereby, these agents are specifically delivered to the targeted tissues and enhance the incorporation amount thereof into the cell, maintaining their efficiency.

EXAMPLES

The following examples are merely illustrative and do not limit the scope of the invention.

(Example 1) Preparation of the Aggregatable Molecules and Micelles for DDS

In the example, the following GFP was used as the protein for preparing the target presenting part and the silole dendrimer was used as a dendrimer.
(1) Preparation of the Aggregatable Molecule for DDS In the example, the compound having the following chemical formula (X) (hereinafter, it is sometimes referred to as "dimethyl dumbbell (1) 6-Br") as the dendrimer having halogen group, and GFP (green fluorescent protein) (Seq. No. 7) was used as the protein having thiol group.

[Chemical formula 11]

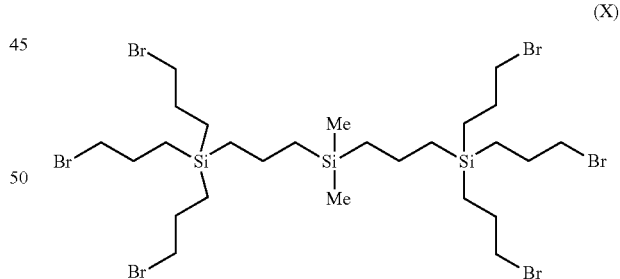

(X)

The GFP (sequence No. 7 in the sequence listing) used here was prepared according to the method that had already been reported by the inventor et al. (see Biochim. Biophys. Acta 1679 (2004) 222-229; Biochem. Biophys. Res. Commun. 330 (2005) 454-460). The amino acid sequence of GFP shown in the sequence No. 7 has replaced the amino acid at the position 251 in the C terminal region with cysteine, and originally presented cysteines at the positions 48 and 70 were replaced with serine and valine respectively.

At first, DTT was added to GFP solution of 20 µM concentration (in PBS) at 1 mM as a final concentration, and the GFP solution was treated for 10 minutes at room temperature to reduce cysteines on the surface of GFP. Ten μL of 200 μM of silole dendrimer shown the formula (VI) solution (in DMSO solution) was added to 400 to 450 μL of 20 μM GFP solution (in PBS) to have the final concentration of 10-fold molar equivalent, and then mixed with vortex mixer.

After vortex, the solution was stood at 37° C. for overnight incubation to bind GFP and the silole dendrimer, and subsequently to form the micelles. The incubation time for this experiment was about 16 to 18 hours. The properties of the micelle particles in the solution were measured by using dynamic light scattering method (DLS; Dynamic light scattering). The result was shown in Table 1.

After vortex, the solution was stood at 37° C. for overnight incubation to bind GFP and the silole dendrimer, and subsequently to form the micelles. The incubation time for this experiment was about 16 to 18 hours. The properties of the micelle particles in the solution were measured by using dynamic light scattering method (DLS; Dynamic light scattering). The result was shown in Table 1.

TABLE 1

Average particle diameters of raw materials and products in PBS measured 5 times at 25° C. [nm]

| | Zeta Average | Particle diameter peak by scattering intensity | Particle diameter peak by number |
|---|---|---|---|
| 20 μM GFP only | 860.7 | 838.8 | 4.682 |
| 50 μM Silole only | 894.5 | 664.6 | 649.3 |
| 20 μM GFP-Silole only | 210.3 | 256.8 | 147.7 |

Figure 3:
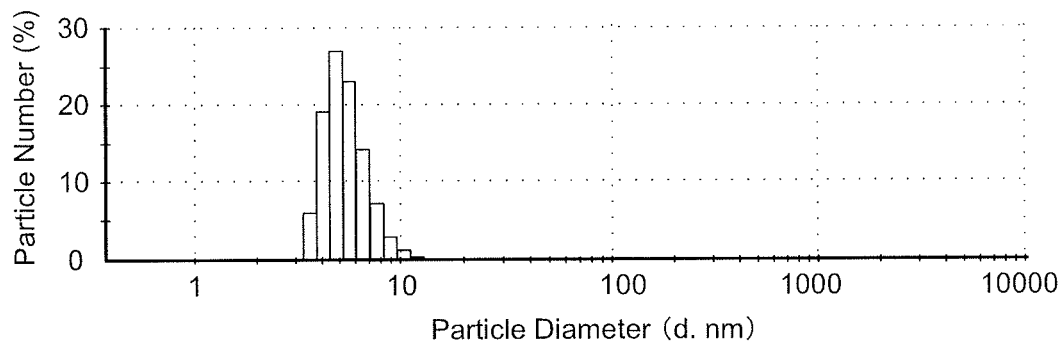
FIG. 3(A), FIG. 3(B) and FIG. 3(C) are graphs showing particle size distribution of prepared micelles.
Figure 3:
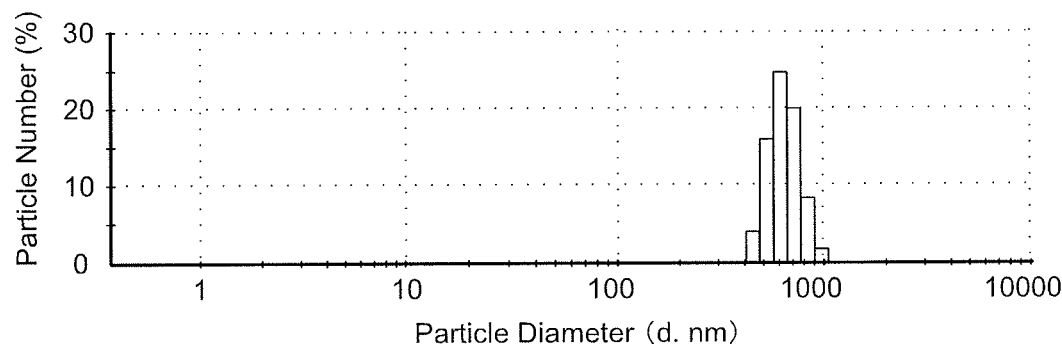
Figure 3:
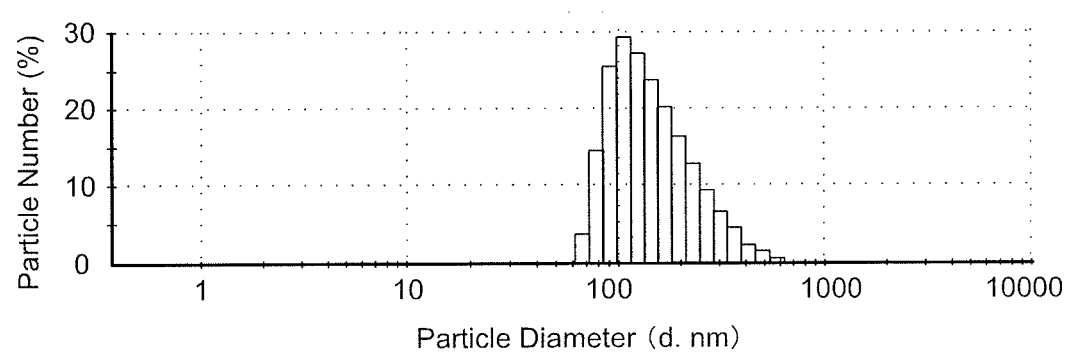

Also, the particle size in the reaction mixture was measured at 25° C. by using ZETASIZER NANO-S (manufactured by Malvern Instrument Ltd.) with a laser beam wavelength of 532 nm. The result was shown in FIG. 3. FIG. 3(A) shows the result that GFP only was incubated and the particle sizes of the obtained products were measured. FIG. 3(B) shows the result that only the silole dendrimer was incubated and the particle size of the obtained product was measured. FIG. 3(C) shows the result that GFP and the silole dendrimer shown in formula (VI) were mixed and incubated, and the particle sizes of the obtained products were measured. The horizontal axis shows the particle sizes of the obtained products, and the vertical axis shows the percentage of the whole products with the sizes shown on the horizontal axis.

When GFP and the silole dendrimer were incubated (in Table 1, it is shown as "GFP-Silole only"), the particle size of the micelle obtained was about 150 nm. In contrast, the particle size observed when GFP only was incubated was about 4 nm, and the particle size observed when silole dendrimer only was incubated was about 650 nm. It was considered that the reason why the large size particles were observed is caused by the aggregation among the silole dendrimers in the incubation of silole dendrimer only to form large aggregates.

Figure 4:
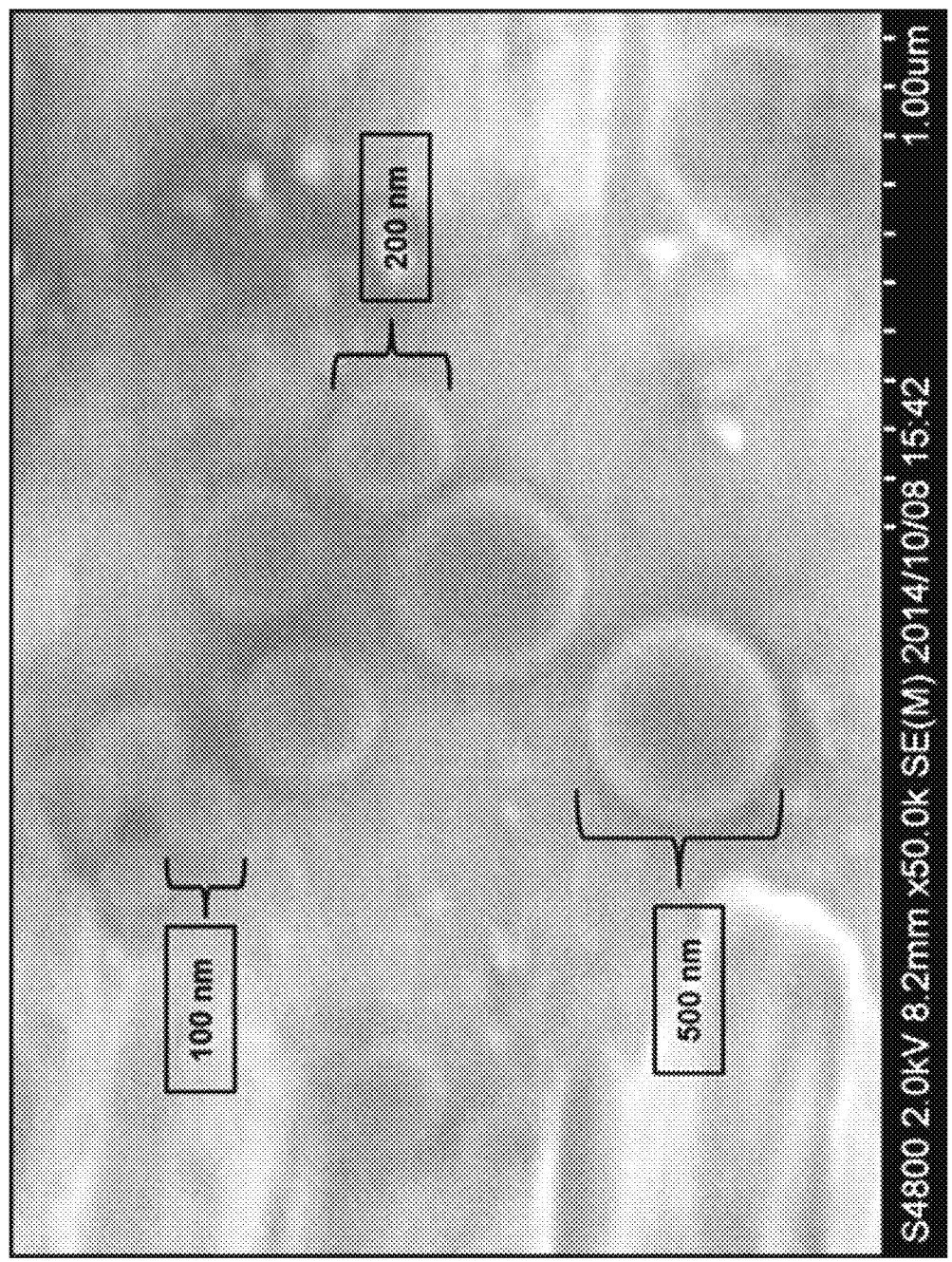
FIG. 4 is a typical electron micrograph of the prepared micelle observed by using a scanning electron microscope (SEM).

Next, according to the observation of the obtained micelle particles by using scanning electron microscope (SEM; Scanning Electron Microscope), a large number of particles having the particle size of about from 100 to 500 nm and a small number of those of about 500 nm were confirmed (see FIG. 4).

From these results, it was clearly demonstrated that the micelle formed by using the aggregatable carrier for DDS of the present invention has the particle size distribution range between about 100 and 500 nm, and there were many particles having the particle size range between about 100 and 200 nm. Also, the electron micrograph by using SEM demonstrated that these particles have spherical micelle structures.

(2) Confirmation of Fluorescence Resonance Energy Transfer

The silole dendrimers used in the example have the emission property that aggregated hydrophobic core parts of the silole gave AIE effects. Therefore, it was confirmed that the dendrimers emit, when they form the micelle structures. Therefore, we examined whether fluorescence resonance energy transfer (FRET: Fluorescence resonance energy transfer) between the silole and GFP occurs or not in the micelles composed of GFP-silole dendrimers to which GFP binds to the silole dendrimer.

Figure 5:
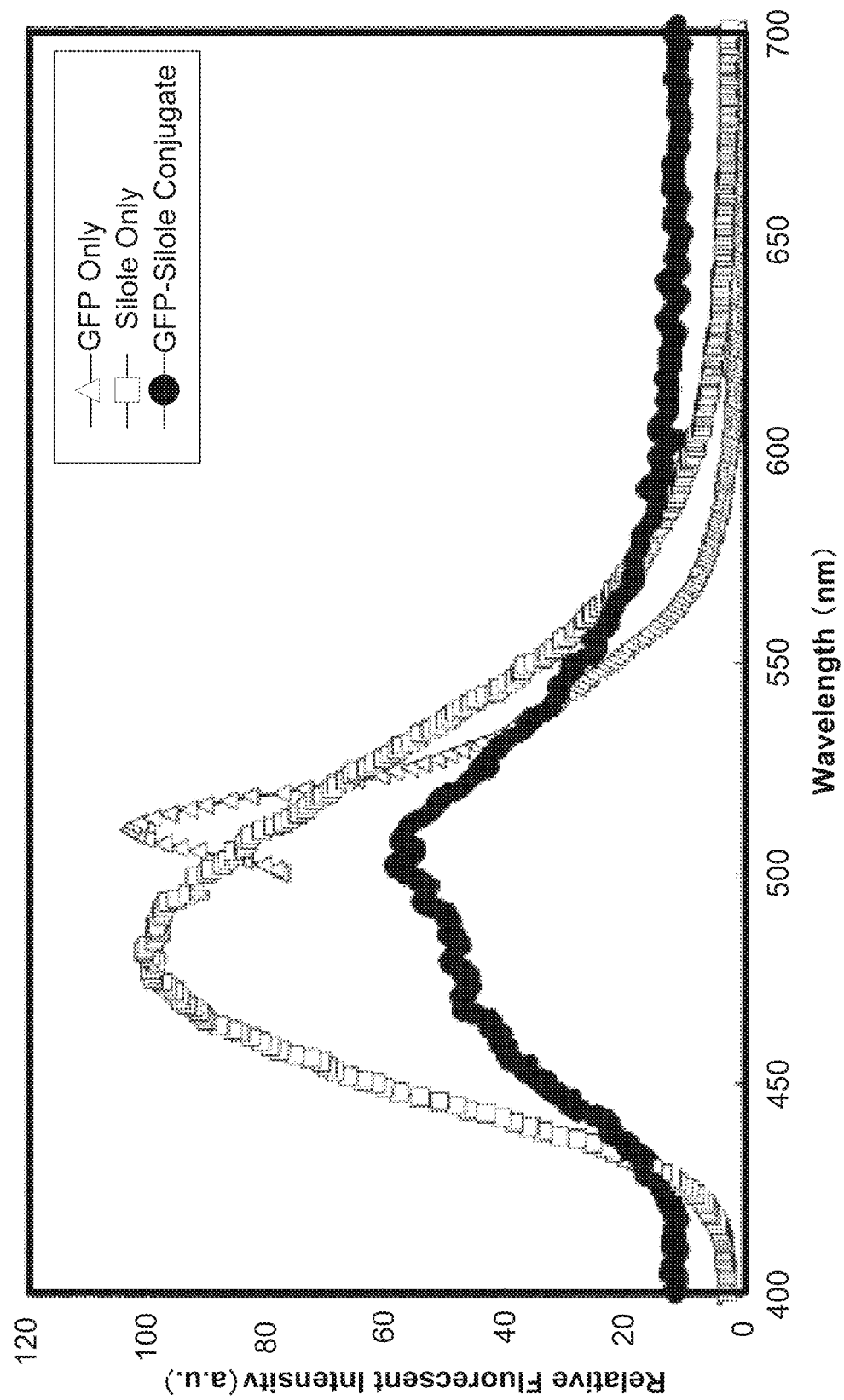
FIG. 5 is the graph showing the emission property of the products obtained by incubating the complex of GFP and silole dendrimer shown in formula (X) (hereinafter, it is referred to as "GFP-silole dendrimer conjugate"), GFP only, or silole dendrimer only shown in formula (X).

Unreacted fluorescent proteins and dendrimers, free molecules, were removed from the reaction mixture; we conducted the emission property experiment (see FIG. 5). In order to examine the emission properties, the incubated products containing the silole dendrimer only was excited at a wavelength of 360 nm (white square), these containing GFP only was excited at the wavelength of 488 nm (white triangle), these containing both of GFP and the silole dendrimer (the micelle of the present invention) was excited at the wavelength of 370 nm (black circle). The micelle being composed of silole-GFP conjugates, which is the products obtained by incubating GFP and silole dendrimer in formula (X), showed the emission caused by FRET to GFP around 510 nm.

As shown in FIG. 5, the silole dendrimer showed the emission peak around 480 nm. Also, the conjugate of GFP and silole dendrimer did not show a sharp emission peak, but it has the highest value around 510 nm. In contrast, GFP showed the sharp emission peak around 510 nm, and it was considered to be due to FRET from the silole dendrimer to GFP. When the micelles were collapsed, the emission from GFP considered to be caused by FRET, was also disappeared.

That is, when the micelles were prepared by using the molecules, which are composed of the dendrimer having AIE effect and the associative protein such as fluorescent protein, the GFP-silole conjugates, they give FRET between the dendrimers and GFP, and collapsed micelle lost FRET.

From the above, it was shown that the use of the micelle of the present invention as the aggregatable carrier for DDS enables to confirm the tissues or organs, to which the micelle was delivered. Also, the fluorescence from the fluorescent protein may be traced even after the micelle delivered to the targeted tissue or organ collapses. Thereby, the intracellular environment and the like may be detected by using the delivered fluorescent protein into the cell.

(3) Experiment for Inclusion of Drugs and the Like into the Micelle Composed of GFP-Silole Dendrimer Complex Next, it was confirmed whether the micelle of the present invention is used for drug inclusion. In the experiment, DiI (1,1'-dioctadecyl-3,3,3',3'-tetramethyl indocarbocyanine perchlorate, Promokine PK-CA707-60010, manufactured by PromoCell GmbH), Oil orange SS (manufactured by Tokyo Chemical Industry, product No: T0553), goat anti mouse IgG (manufactured by Abcam plc, product No. ab6708)-Alexa 610 (manufactured by Molecular Probes, product No.: A30050) and WGA (Wheat Germ Agglutinin: wheat germ agglutinin, manufactured by Molecular Probes) (WGA-Alexa Fluoro (registered trade mark) 594 conjugate, product No.: W11262) were used as model drugs.

Ten μL of 200 μM of the silole dendrimer (in DMSO solvent) shown in the formula (X) was added to 20 μM of GFP, of which cysteine was reduced, to have final concentration of 10-fold molar equivalent, and any one of followings was added and mixed with vortex mixer, and incubated overnight at 37° C. (about 16 to 18 hours): DiI (final concentration; 1 µM, fluorescent dye), Oil orange SS (final concentration; 20 µM, fluorescent dye), goat anti mouse IgG-Alexa 610 (final concentration; 0.1 µM) and WGA (final concentration; 2 µM).

It was measured whether the micelles including each drug are formed in the sample to which each model drug is added; and if the micelles including the drug are formed, their particle size were measured by using the dynamic light scattering method. The results were shown in Table 2. Here, DiI, Oil orange SS, and goat anti mouse IgG-Alexa 610 were used as drug models.

Figure 6:
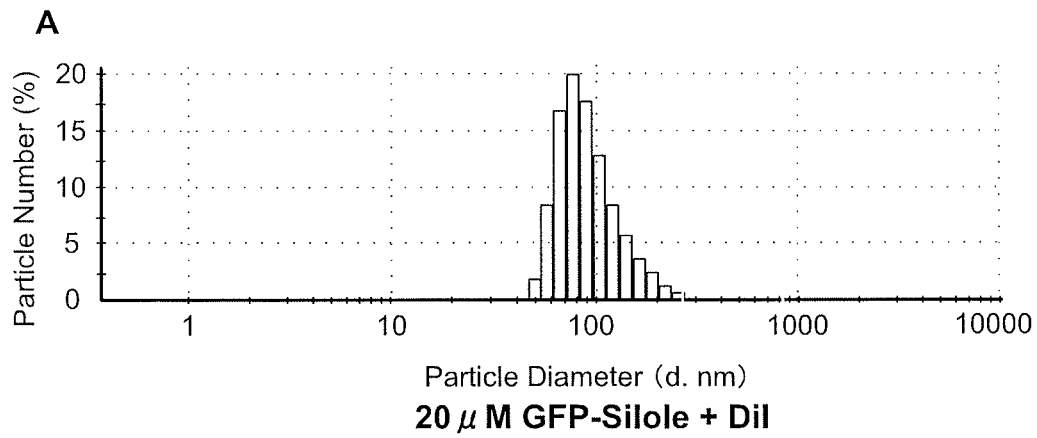
FIG. 6(A), FIG. 6(B) and FIG. 6(C) are graphs showing the particle size distribution of the micelle prepared in the presence of the model drug.
Figure 6:
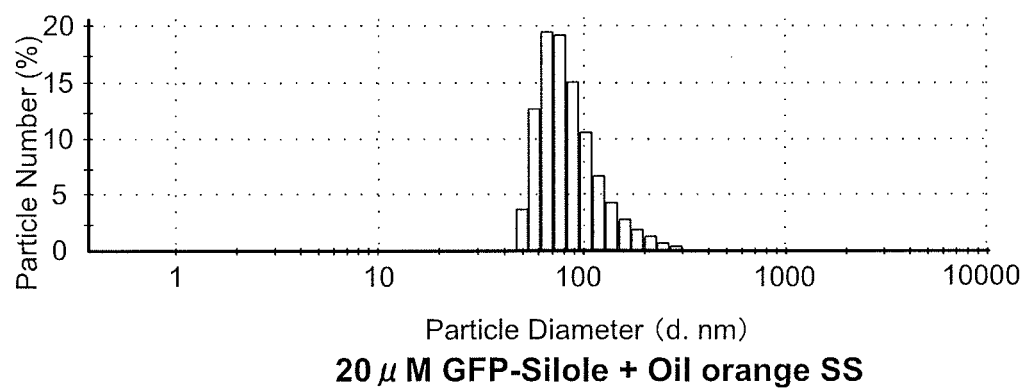
Figure 6:
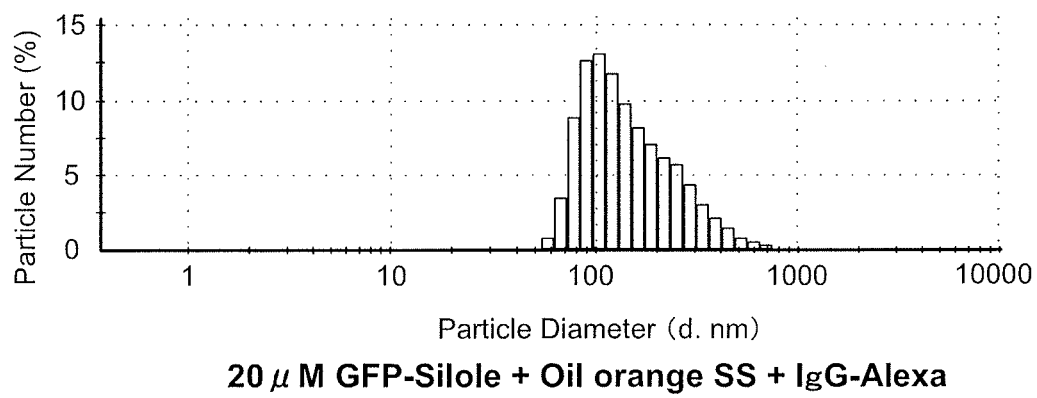

FIG. 6(A), FIG. 6(B) and FIG. 6(C) show the particle size distributions, when the model drugs were used. FIG. 6(A) shows the distributions in the presence of DiI; FIG. 6(B) shows these in the presence of Oil orange SS; and FIG. 6(C) shows these in the presence of goat anti mouse IgG-Alexa 610 respectively, when the micelles were prepared with these model drugs. The horizontal axis shows the particle size of the micelle, and the vertical axis shows the percentage of the micelles having each size shown on the horizontal axis against the whole micelle numbers. When DiI was added, the micelle size was about 95 nm; when Oil orange SS was added, it is also about 95 nm; and when IgG-Alexa 610 was added, it was about 180 nm.

TABLE 2

Average particle diameter of raw material and product in PBS measured 5 times at 25° C. (nm)

| | Zeta Average | Particle diameter peak by scattering intensity | Particle diameter peak by number |
|---|---|---|---|
| 20 µM GFP-Silole only | 210.3 | 256.8 | 147.7 |
| 20 µM GFP-Silole + DiI | 137.3 | 159.6 | 95.27 |
| 20 µM GFP-Silole + Oil orange SS | 147.6 | 177.2 | 94.77 |
| 20 µM GFP-Silole + Antibody-Alexa 610 | 277.7 | 324.3 | 179.7 |

Figure 7:
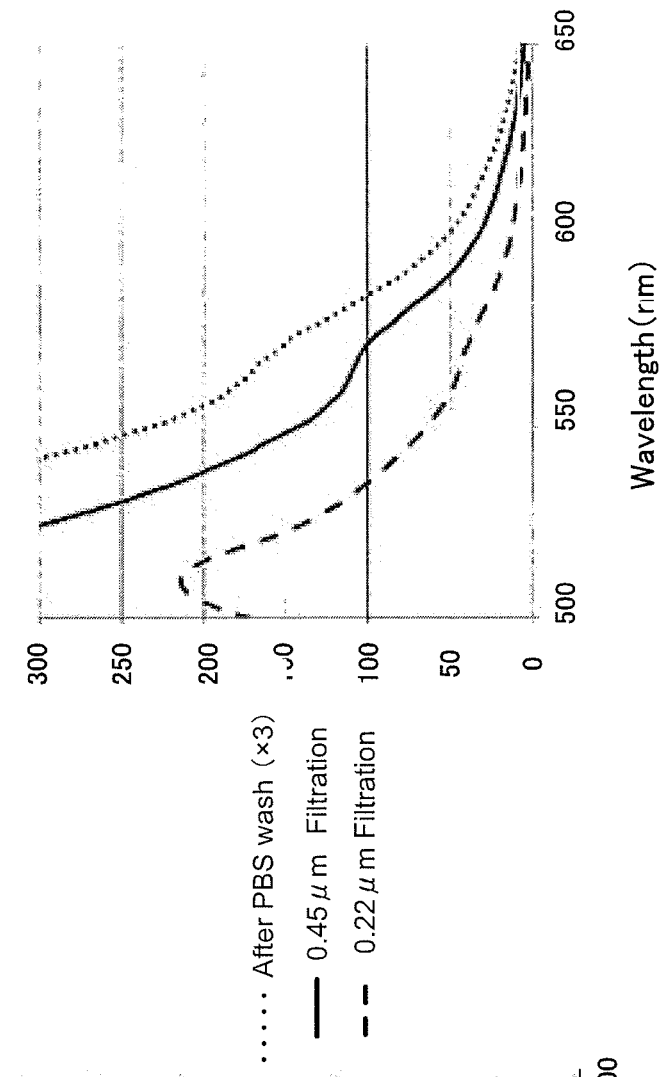
FIG. 7(A) and FIG. 7(B) are graphs showing the emission property, when the micelle consisting of GFP-silole dendrimer complex and it includes DiI. The micelle was excited at 370 nm.

FIG. 7 shows the examination result for the emission properties of the micelles including DiI, the fluorescent dye. FIG. 7(B) shows enlarged drawing of the spectrum in FIG. 7(A), around 500 nm. The horizontal axis shows wavelength (nm), and the vertical axis shows relative fluorescent intensity (a.u.). At first, the micelles including DiI were prepared, and following test samples were prepared for measuring their fluorescence: the micelles washed 3 times with PBS; the filtered reaction mixture through a filter having a pore size of 0.45 µm to remove free dye; and the filtered reaction mixture through the filter having the pore size of 0.22 µm instead of the filter having the pore size of 0.45 to remove free dye.

As shown in both FIG. 7(A) and FIG. 7(B), shoulder peaks were observed around the wavelength of 480 nm, when the samples were excited at the wavelength of 370 nm. It was considered that these peaks appeared the emission from the silole. It was considered that the peak around 510 nm appeared FRET from the silole to GFP; and the peak around 570 nm appeared FRET from the silole to DiI. From these results, it was confirmed that DiI was included in the micelle.

Figure 8:
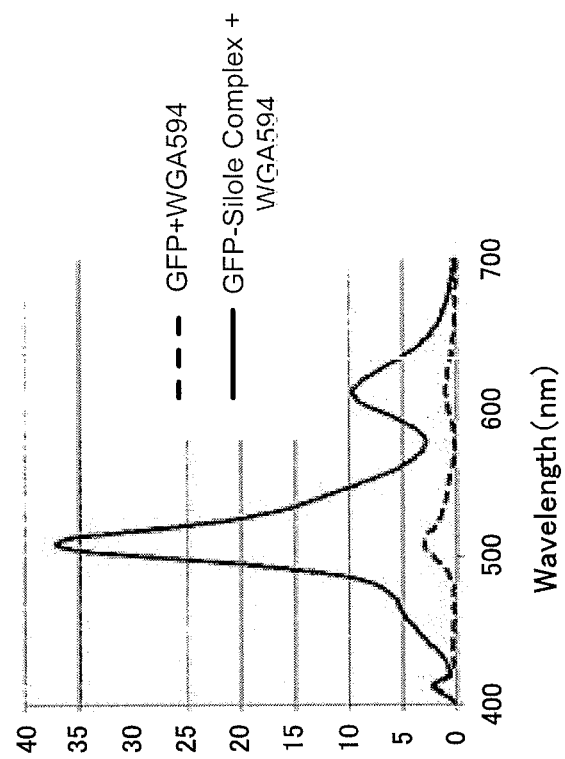
FIG. 8(A) and FIG. 8(B) are graphs showing the emission property, when the micelle consisting of GFP-SD, silole dendrimer complex, and it includes WGA labeled with Alexa 594. The micelle was excited at 370 nm.
Figure 8:
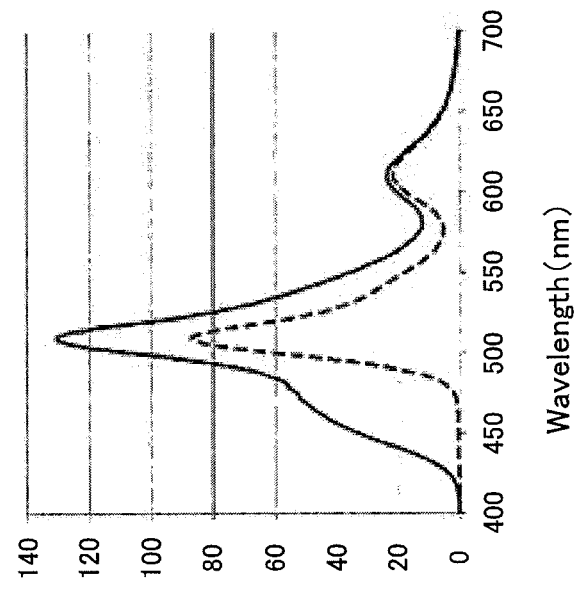

Next, the emission properties of the micelles including WGA labeled with Alexa 584 was examined (see FIGS. 8 A and B). FIG. 8 A shows the measurement results of the reaction mixture in situ, when Alexa 594 labeled WGA was added. Also, FIG. 8(B) shows the measurement results after removal of the unincorporated stuffs into the micelles such as the unreacted proteins, Alexa labeled WGA, the silole dendrimer, or GFP by using the ultrafiltration spin column (manufactured by Millipore). In FIG. 8, the solid line shows the emission property of the products obtained by mixing treatment of GFP-silole dendrimer complex and WGA; and the broken line shows that of the products obtained by mixing treatment of GFP and WGA.

In the figure, the solid line shows the measurement result for the micelle composed of GFP-silole dendrimer complex including Alexa 594 labeled WGA; and the broken line show the measurement result for that including the mixture of GFP and Alexa 594 labeled WGA respectively (Excitation wavelength is 370 nm in each case).

FIG. 8A shows the measurement result for the reaction mixture without the ultrafiltration spin column treatment in situ. In FIG. 8 A, the emission from the silole dendrimer, GFP and WGA were detected around 480 nm, 510 nm and 610 nm respectively. In contrast, as shown in FIG. 8 B, the sample with the ultrafiltration spin column treatment did not show the emission from the free silole dendrimer, GFP and WGA, because they were removed (the broken line). From the above, it was confirmed that Alexa 594 labeled WGA was included the prepared micelle.

(Example 2) Preparation of the Fluorescent Protein which Binds the Target Peptide Sequence The target peptide sequence binding fluorescent protein was prepared as follows. The protein bound to the micelle of the present invention at the C terminal, and it bound to the target peptide, which binds the receptor expressed on the surface of a cancer cell, at N terminal.

(1) Inverse PCR (1-1) Selection of the Peptide Sequence

The peptide sequence of the selected target peptide was shown in the following Table 3. MCF-7 is a human breast adenocarcinoma-derived cell, having the sequence listed in the following Table 3, and it is sometimes referred to as "target type 1". MCF-2 is the variant of MCF7-1 having the sequence listed in the following Table 3, and it is sometimes referred to as "target type 2". Also, MCF7-1+α stand is another variant having the structure that the short peptide with α-helix, which is sometimes referred to as "α-stand", was connected to MCF7-1 as shown in the following Table 3, and it is sometimes referred to as "type 1 enhanced".

TABLE 3

| Cell Species | Peptide Sequence | Seq. No. |
|---|---|---|
| MCF7-1 | DMPGTVLP | 1 |
| MCF7-2 | VPTDTDYSGG | 2 |
| MCF7-1 + α stand | DMPGTVLPGG GGGSEGEWQQQQHQWAKQE | 3 |

(1-2) Preparation of Primers

Primers for conducting inverse PCR of the peptide sequence shown in Table 3 were written in the following Table 4. Among these primers, Seq. No. 1 and 3 in the sequence listing were designed so as that elongation reaction initiates between DM and PGTVLP of the peptide sequence. Seq. No. 2 was designed so as that the reaction initiates between VP and DTDYSGG of the peptide sequence. They were designed for conducting optimal inverse PCR.

TABLE 4

| Introduced Peptide Sequence | primer | Seq. No. |
|---|---|---|
| DMPGTVLP (Seq. No. 1) | F: CCTGGTACTGTTCTTCCTGGTGGTATGAGT AAAGGAGAAGAACTT | 12 |
| | R: CATATCGCGACCCATTTGCTGTCCACC | 13 |
| VPTDTDYSGG (Seq. No. 2) | F: ACTGATACTGATTATAGTGGAGGAATGAGT AAAGGAGAAGAACTT | 14 |
| | R: AGGAACGCGACCCATTTGCTGTCCACC | 15 |
| DMPGTVLPGG GGGSEGEWQQ QQHQWAKQE (Seq. No. 3) | F: CAACAACAACAACATCAATGGGCAAAACAA GAAATGAGTAAAGGAGAAGAA | 16 |
| | R: CCATTCACCTTCACTACCACCACC ACCACCAGGAAGAACAGT | 17 |

(1-3) Preparation of the Template Plasmid for Inverse PCR

A template plasmid for inverse PCR was prepared by the method described in the following paper. "Protease-sensitive signaling by chemically engineered intramolecular fluorescent resonance energy transfer mutants of green fluorescent protein (Miho Suzuki, et al. Biochimica et Biophysica Acta (BBA)—Gene Structure and Expression Volume 1679, Issue 3, 17 Sep. 2004, Pages 222-229).

(1-3-1) Plasmid Construction for GFPuv5 Mutant

GFPuv5 was prepared from the pGFPgcn4 as follows. Firstly, the inverse PCR products, which has a synonymous mutation for gene manipulation was generated by using inverse PCR with I167T mutation and forward primer, 5'CATTGAAGATGGCTCCGTTCAA (Sequence No. 18) and reverse primer, 5'CATTGAAGATGGCTCCGTTCAA (Sequence No. 19), were obtained. Subsequently, cyclization treatment of the products was conducted for obtaining GFPuv5. The construct obtained in this way was named pGFPgcn5.

After that, cDNA of GFPuv5 was cloned into pET21a (manufactured by Novaben Inc.) to express the protein, and then the protein was purified and named GFPuv5tag. The code region was amplified by using the primers 5'CTCGAC-CAT[ATGGCTAGCATGACTGGTGGACAGCAAATG-GGT]CGCATGA GTAAAGGAGAAGAACTTTTCA (Sequence No. 20) and 5' TGACGTGAATTCATTA[GT-GATGGTGATGGTGATG]TTTGTAGAGCTCATCC ATGC (sequence No. 21) in Sequence No. 20, an adhesive tag adhering to the epitope tag composed of 11 amino acids from the terminal for 10 proteins of T7 gene toward N terminal of GFPuv5 series was marked as [ ]. The Sequence No. 21 provides His tag to C terminal of GFPuv5 series, and His tag in the sequence was shown as [ ].

The DNAs having the nucleotide sequences shown in the Seq. Nos. 1 to 3 were inserted into pET21a, and then it was digested with both of NdeI and EcoRI. The pGFPgcn plasmid was used for gene manipulation and the pET21a plasmid was used for protein expression under the control of the T7 promoter. The nucleotide sequences of the gene of GFPuv5 and the mutants thereof were confirmed by DNA sequencing (ABI PRISM 3100, manufactured by Genetic Analyzer). Three more synonymous mutations were found during the experiment. Those have the following mutations: agt to agc at Ser at 30, cat to cac at His 78, and caa to cag at Gln 183.

The experiment was continued including these mutations, because these mutations were not harmful for the fluorescent proteins. The fluorescent intensity of the purified GFPuv5tag was about 1.9 times higher than that of GFPuv4tag. After that, either of the cysteine residues at position 48 or position 70 was replaced with randomized amino acid by inverse PCR using pGFPgcn5.

Both oligonucleotides 5' CTTAAATTTATTNNKACTG-GAAAAC (Seq. No. 22) and 5' GGTAAGTTTTCCGTATGTTG (Seq. No. 23) were used for mutation of cysteine 48. Both of 5' GTGTT-CAANNKTTTTCCCGTTATCCG (Seq. No. 24) and 5' CATACGTCAGAGTAGTGACAAG (Se. No. 25) were used for the mutation of cysteine 70. Culture of E. coli BL21 (DE3) was transformed with the obtained plasmids and screened by using daylight excitation for those having strong fluorescence, and selected on an agar medium. Several mutants emitting strong florescence were obtained at position 48 (replaced with one of Ala, Asp, Glu, Gly, Ile, Leu, Asn, Pro, Ser, Thr, Val, and Tyr). However, the C70V cysteine mutant, which has the mutation at position 70, gave only proper fluorescence.

In order to produce double cysteine mutations GFPuv5 having strong fluorescent intensity, the plasmid having the single mutation was digested with both of NcoI and EcoRI and ligated to each region again. Selection was conducted by using the single mutants. The UV5CO tag (C48S/C70V) showed the highest fluorescence intensity among all the recombinants.

Next, cysteines were introduced at both positions 6 and 229 by inverse PCR, respectively. The plasmid having C48S mutation and a set of the following primers were used for introducing respective mutation.

For Glu replacement: 5'TGTCTTTTCACTG-GAGTTGTCCC (Seq. No. 26) and 5' TTCTCCTTTACT-CATTTTTTC (Seq. No. 27)

For Ile replacement: 5'TGCACACATGGCATGGAT-GAGCTC (Seq. No. 28) and 5'CCCAGCAGCAGTTA-CAAACTC (Seq. No. 29)

Three protease tags having trypsin target sequence (Glu-Gly-Arg) have various spacer sequence, which were no spacer, Thr spacer or Gly-Thy spacer, and necessary cysteine was replaced between His-231 and Asp-231. These constructs were obtained by using puvC48Stag, the obtained plasmid (a template), and the primers shown in the following Table 5.

TABLE 5

| Plasmid Name | Primers | Seq. No. |
|---|---|---|
| pUV5trypS0tag (without spacer) | F: 5'CAGCGCCGTTGTGAGCTCTAC AAATAATGAATT | 30 |
| | R: 5'TGTAATCCCAGCAGCAGTTAC | 31 |
| pUV5 - trypS1tag (with Thr spacer) | F: 5'ACATGTGAGCTCTACAAATAA | 32 |
| | R: 5'ACGGCCCTGTGTAATCCC | 33 |
| pUV5trypS2tag (with Gly-Thr spacer) | F: 5'GGAACATGTGAGCTCTACAAA | 34 |
| | R: 5'ACGGCCCTGTGTAATCCC | 33 |

(1-3-2) Purification of GFPuv5tag Mutant

E. coli BL 21 (DE3) was transfected by using all of the plasmids. 12 mL of E. coli at the stationary phase after overnight culture was seeded in 38 ml of LB medium supplemented with 50 µg/ml ampicillin and 0.5 mM IPTG, and incubated at 37° C. for 8 hours. The cells were collected by centrifugation at 2,500×g for 20 minutes and resuspended in 10 mL of PBS. The pellet of the cells was lysed in 10 ml of lysis buffer (pH 8.0) containing 50 mM Tris and 8 M urea at room temperature for 15 minutes, and then vortexed. The lysed cells were centrifuged at 1,200×g for 15 minutes, and the supernatant was taken to mix with $Ni^{2+}$-NTA resins (manufactured by Qiagen Co. Ltd.) which were suspended in PBS. After sequentially washing the resins with PBS and 20 mM imidazole, the bound GFPuv5tag mutant was eluted with 250 mM imidazole solution.

In order to exchange the buffer, the eluate was applied to PD-10 gel electrophoresis filtration column (manufactured by Amersham Bioscience Co. Ltd.), which was equilibrated with 10-fold diluted PBS. The eluted GFPuv5tag mutant protein was collected, and the concentrations thereof were determined by using Coomassie protein assay reagent (manufactured by Pierce Co.). Purified GFPuv tag mutants were analyzed by 15% SDS-PAGE.

Nucleic acid sequence of the template plasmid for inverse PCR was shown as Sequence No. 26.

(1-4) Conditions for PCR

A reaction mixture shown in the following Table 6 was prepared, and the inverse PCR was conducted under the condition shown in the following Table 7.

TABLE 6

| Components | Amount (µL) |
|---|---|
| Template(plasmid->pET21a (+) NSS25 | 5 |
| KOD Dash Buffer (Toyobo Co. Ltd.) | 5 |
| 2 mM dNTP (Toyobo Co. Ltd.) | 5 |
| F primer (2.5 pmol) | 10 |
| R primer (2.5 pmol) | 10 |
| KOD Dash (2.5 U/µL) (Toyobo Co. Ltd.) | 0.5 |
| Sterile distilled water | 14.5 |
| Total | 50 |

TABLE 7

| Temp. (°C) | Reaction period (min.) | Cycles |
|---|---|---|
| 95 | 3 | — |
| 98 | 0.1 | 5 |
| 65 | 2 | |
| 70 | 4 | |
| 98 | 0.1 | — |
| 74 | 2 | 25 |
| 70 | 4 | |
| 70 | 7 | |
| 4 | — | — |
| 4 | — | — |

(1-5) Confirmation by Gel Electrophoresis

Figure 9:
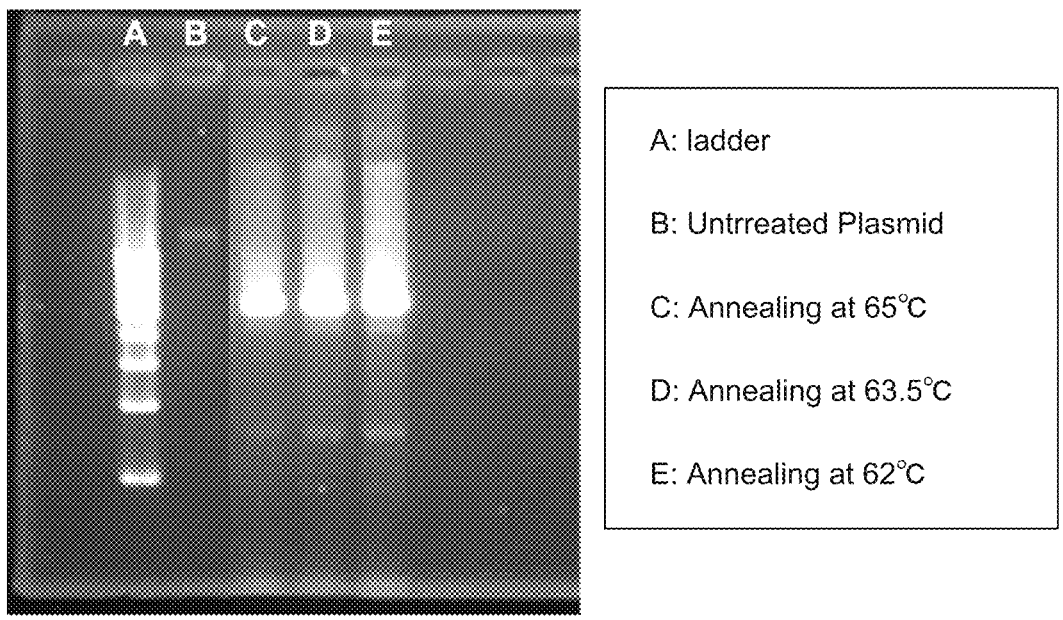
FIG. 9 is an electrophoresis gel image of inverse PCR product after inverse PCR at different annealing temperatures.

A portion of the PCR solution was taken, and subjected to gel electrophoresis with 0.8% PAGE at voltage 100 V for 30 minutes of applied voltage time to confirm the amplified peptides in each sample. The result of the electrophoresis was shown in FIG. 9.

(2) Removal of Independent a Sequence and Purification of PCR Products

The reaction mixture shown in the following Table 8 was prepared and reacted at 120° C. for 30 minutes to remove the independent A sequence which was produced by the PCR. After that, the PCR products were purified by using QIAquick (a registered trademark), PCR Purification Kit (manufactured by QIAGEN) according to the instruction attached to the kit.

TABLE 8

| Composition | Amount (µL) |
|---|---|
| inverse PCR product | 50 |
| 10 × NE Buffer 2.1 (New England Biolabs Inc. (NEB)) | 1 |
| 10 mg/ml BSA (NEB) | 2 |
| 2 mM dNTP | 8.3 |
| T4 DNA polymerase (3,000 unit/µL) (NEB) | 0.5 |
| Total | 60 |

(3) Ligation Reaction

Subsequently, the reaction mixture shown in the following Table 9 was prepared and reacted at 16° C. for more than 3 hours to prepare a circular plasmid for transformation of E. coli DH5α described later. Depending on the variants, the temperature, 25° C., 37° C., and the like were used.

TABLE 9

| Composition | Amount (µL) |
|---|---|
| PCR product | 8 |
| 10 × T4ligase B (NEB) | 1 |
| T4 DNA polynucleotide kinase (40,0000 unit/µL) (NEB) | 0.5 |
| T4 DNA ligase (10,000 unit/µL) (NEB) | 0.5 |
| Total | 10 |

(4) Transformation of E. coli DH5α

10 µL of competent cells of E. coli DH5α (manufactured by BioDynamics Laboratory) was thawed on ice immediately before use, and prepared a competent cell solution. One µL of the ligation reaction solution was added to the competent cell solution, and left on ice for 30 minutes. After that, the solution was incubated at 42° C. for 30 seconds and then cooled on ice for 2 minutes. 90 µL of SOC medium (manufactured by TOYOBO Co., LTD.) was added to the solution, and reacted on a shaker at 37° C. for 1 hour. Thereafter, it was seeded on LB selection medium supplemented with ampicillin (manufactured by TOYOBO Co., LTD.), and incubated for overnight at 37° C.

(5) Colony PCR

Colonies obtained from the transformation were subjected to Colony PCR to confirm the predicted inserts.

(5-1) Preparation of the Reaction Mixture for PCR

The reaction mixture for colony PCR shown in the following Table 10 was prepared.

TABLE 10

| Composition | Amount added (µL) |
|---|---|
| KOD Dash Buffer (Toyobo Co. Ltd.) | 2 |
| 2 mM dNTP | 2 |
| Double His primer (2.5 pmol) | 4 |
| pET primer | 4 |

TABLE 10-continued

| Composition | Amount added (μL) |
|---|---|
| KOD Dash (2.5 U/μL) (Toyobo Co. Ltd.) | 0.2 |
| Sterilized distilled water | 7.8 |
| Total | 20 |

The reaction mixture for colony PCR was poured into a PCR tube. E. coli grown on the LB medium supplemented with ampicillin was collected and added to the tube. PCR was conducted according to the program shown in the following Table 11.

TABLE 11

| Temp. (°C) | Reaction time (min.) | Cycles |
|---|---|---|
| 95 | 3 | — |
| 98 | 0.5 | 5 |
| 50 | 0.5 | |
| 70 | 0.5 | |
| 98 | 0.1 | — |
| 72 | 0.5 | 25 |
| 70 | 0.5 | |
| 70 | 7 | |
| 4 | — | — |

(5-2) Electrophoresis

Electrophoresis of the PCR reaction mixture was conducted with 1.2% PAGE at applied voltage of 100 V for 30 minutes. The colonies of which amplification were confirmed were inoculated into the culture bottle containing LB liquid medium (manufactured by TOYOBO Co., LTD.) and incubated at 37° C.

(6) Purification of Plasmid

The plasmid in E. coli cultured in the LB liquid medium was purified by using Wizard Plus SV Minipreps. DNA Purification System (manufactured by Promega Co.) according the instruction attached thereto. After that, the sequences of the purified plasmid were sent to Eurofin Genomics Co., Ltd. for their analysis.

(7) Transformation of E. coli BL21 (DE3)

Ten μL of E. coli BL21 (DE3) competent cells (manufactured by BioDynamics Laboratory) were thawed on ice immediately before use, and prepared the competent cell solution. One μL of the plasmid solution, which was confirmed to contain the target sequence by the sequencing, was added to the competent cell solution, and left to stand on ice for 30 minutes.

After that, the solution was incubated at 42° C. for 30 seconds and then cooled on ice for 2 minutes. 90 μL of SOC medium (manufactured by TOYOBO Co., LTD.) was added to the solution, and reacted on a shaker at 37° C. for 1 hour. Thereafter, it was seeded on LB selection medium supplemented with ampicillin, and left to stand overnight at 37° C. Next day, transformed colonies emitting green fluorescence were collected, and inoculated into culture bottles containing 1 ml of LB liquid medium supplemented with ampicillin. Then, they were left to stand overnight at 37° C. for pre-culture.

(8) Purification of the Fluorescent Protein Binding to the Target Peptide Sequence (8-1) Colony Cultivation For samples, 4 tubes in 50 mL size to which both of 4 ml of the LB liquid medium supplemented with ampicillin and 290 μL of the pre-cultured solutions were added were prepared, and cultured on the shaker at 28° C. for 4 hours. After that, 43 μL of 100 mM IPTG (isopropyl-1-thiogalactopyranoside) was added to them, and they were cultured overnight at 28° C. on the shaker.

(8-2) Recovery of the Protein

Next day, the cultures in the four tubes were collected into one tube. Three tubes of which contents were transferred were washed with 1 ml PBS (−) buffer (manufactured by Wako Pure Chemical Industry, Ltd.), and the washed solutions were also added to the collected tube to which the cultures were collected. The tube containing the collected cultures was centrifuged at room temperature for 5 minutes at 5,000 rpm (the name of centrifuge: KUBOTA3740, the rotor number: KUBOTA AF2018, manufactured by KUBOTA Co.)

After that, (i) the supernatant was removed and 3 ml of PBS (−) buffer was added to the precipitation pellet (ii) to vortex well, and then the tube was centrifuged at 5,000 rpm for 5 minutes. The steps (i) and (ii) were repeated twice. Four ml of B-PER Lysis Buffer (manufactured by Reagent) was added to the precipitation pellet, and it was capped and stirred overnight at room temperature on the shaker.

(8-3) Purification by His-Tag

Two ml of Ni-NTA Agarose (manufactured by QIAGEN) was put in 15 ml tube, (i) the tube was centrifuged at 1,000 rpm for 1 minute, (ii) the supernatant was discarded, and 1×PBS buffer was added to the tube and vortexed well. The steps (i) and (ii) were repeated three times for preparing Ni-NTA resin.

The tube containing B-PER Lysis buffer solution was centrifuged at 12,000 rpm for 10 minutes at room temperature, and then the supernatant was transferred to a 15 ml Falcon tube. 400 μL of well stirred Ni-NTA resin was added to the tube, and then the tube was placed on the rotary shaker and shook at room temperature for 10 minutes. After that, the tube was centrifuged at 1,000 rpm for 1 minute at room temperature, and the supernatant was discarded. (iii) 4 mL of 1×PBS buffer was added to the tube and vortexed well, (iv) the tube was centrifuged at 1,000 rpm for 1 minute at room temperature, and the supernatant was discarded. The steps (iii) and (iv) were repeated twice.

After that, (v) 4 ml of 20 mM imidazole (manufactured by Wako Pure Chemical Industry, Ltd.) was added to the tube and vortexed well, (vi) the tube was centrifuged at 1,000 rpm for 1 minute at room temperature, and the supernatant was removed. The steps (v) and (vi) were repeated twice. 500 μL of 250 mM imidazole was added to the tube, and was stirred at room temperature for 10 minutes with the rotary shaker. Thereafter, the tube was centrifuged at 1,000 rpm for 1 minute, and the supernatant emitting green fluorescence was transferred to a new 15 ml Falcon tube to prepare the protein purified solution for the gel filtration in next stage.

(8-4) Purification by Gel Filtration

Imidazole in the protein purified solution was exchanged with PBS and the solution was purified to obtain the target peptide sequence binding fluorescent protein of interest. In the procedures described above, Nap 5 column manufactured by GE Heath Care Japan KK. was used to conduct the purification according to the instruction attached thereto.

(9) Selection of the Target Peptide Sequence Binding Fluorescent Protein

The concentration of the target peptide sequence binding fluorescent protein obtained from the purification procedure was measures by using absorbance, 280 nm, and the chromophore concentration (chromophore forming ability) was measured by using absorbance, 488 nm, according to the conventional method. The proteins of which ratio of A488/A280 exceeded 1.5 were selected as the target peptide sequence binding fluorescent protein of the interest. The result was shown in Table 12.

TABLE 12

| Type | Absorbance | Wave length (nm) 280 | Wave length (nm) 488 | Ratio 488/280 |
|---|---|---|---|---|
| Target type 1 | sample 1 | 0.2459 | 0.5246 | 2.1335 |
| | sample 2 | 0.2487 | 0.5295 | 2.1289 |
| | sample 3 | 0.2494 | 0.5307 | 2.1280 |
| Target type 2 | sample 1 | 0.4280 | 0.8236 | 1.9241 |
| | sample 2 | — | — | — |
| | sample 3 | — | — | — |
| Target type 1 enhanced | sample 1 | 0.6300 | 0.9039 | 14348 |
| | sample 2 | 0.7695 | 1.1427 | 14850 |
| | sample 3 | — | — | — |
| Non-target type | sample 1 | 0.6689 | 13 189 | 1.9717 |
| | sample 2 | 0.4544 | 0.9915 | 2.1821 |
| | sample 3 | 1.0079 | 20110 | 1.9952 |

(Example 3) Preparation of the Target Peptide Sequence-Binding Aggregates (Associated Fluorescent Protein Driving Type Micelle)

Instead of GFP, the target peptide sequence binding fluorescent protein prepared in the example 2 was used to form the micelles to which target peptide sequences were bound, an associated fluorescent protein driving micelle, as the same as those employed in the example 1.

(1) Emission Properties

Figure 10:
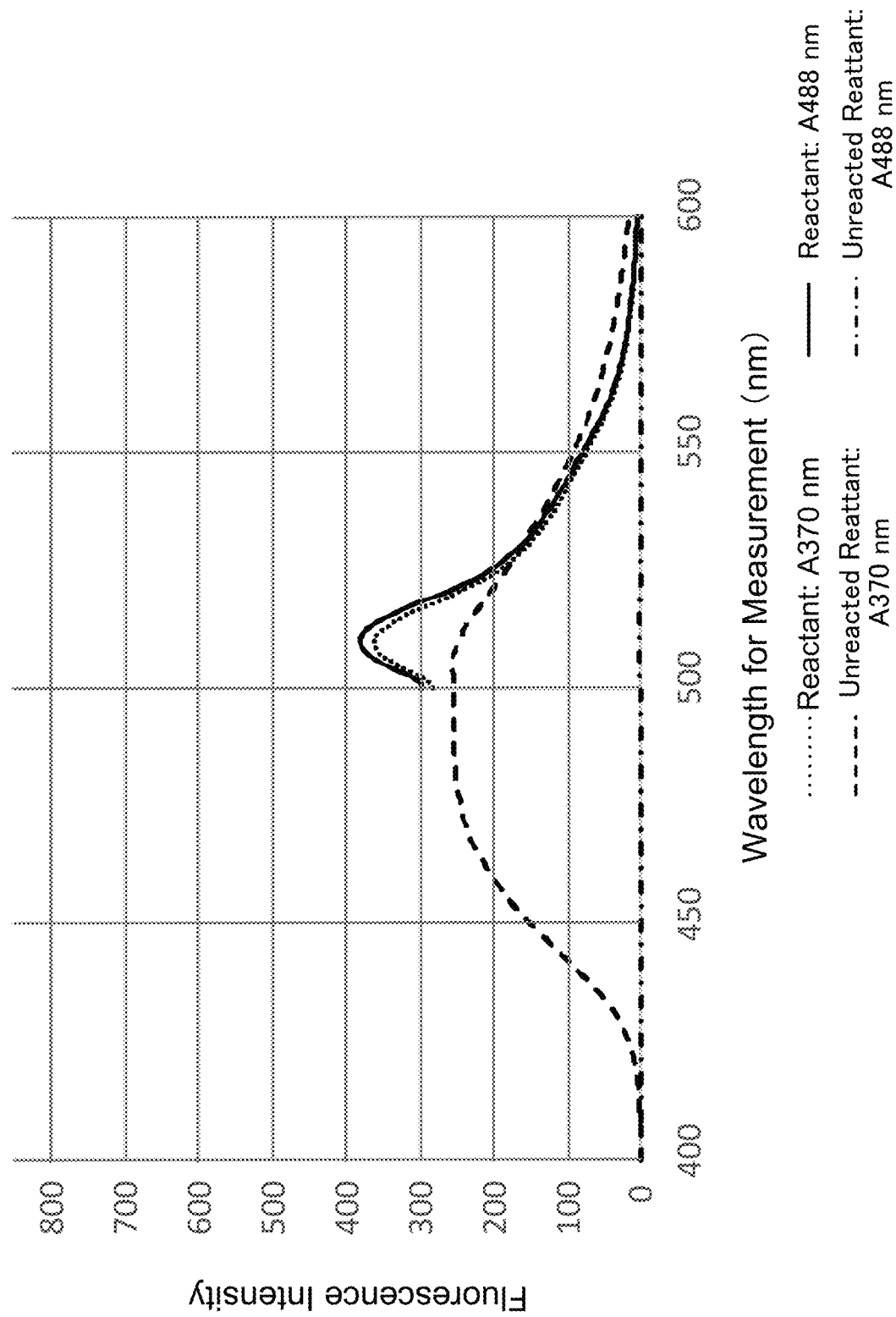
FIG. 10 is the graph showing the measuring result of the fluorescent spectrum of aggregated fluorescent protein driven micelle to which the target peptide sequence is bound.

The emission properties of the associated fluorescent protein driving micelle with target peptide sequence binding fluorescent protein prepared as described above were measured in the same way as in the example 1 (see FIG. 10). In the legend of FIG. 10, the reactant shows the conjugate of the silole dendrimer and the target peptide sequence binding fluorescent protein, the unreacted material shows those without them, and each number shows the wavelength of excitation light (nm). An emission peak was also observed around 510 nm in the target peptide sequence-binding micelle as the same as that in the example 1.

(2) Particle Properties

Figure 11:
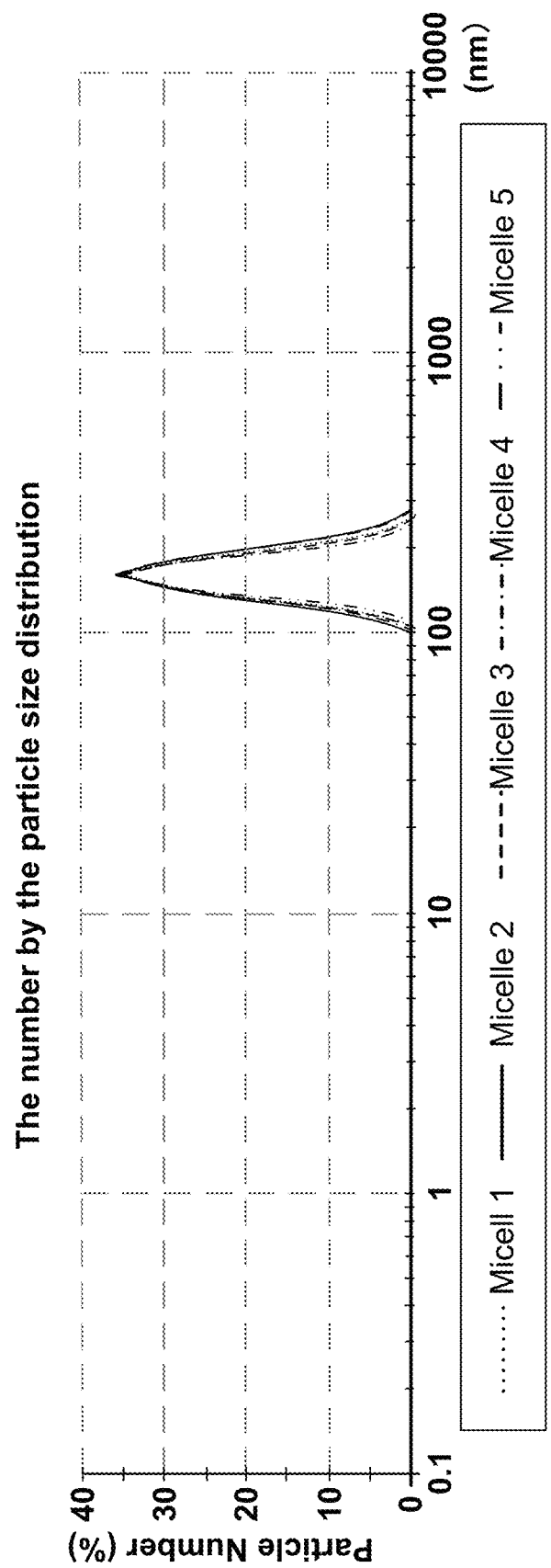
FIG. 11 is the graph showing the particle size distribution of aggregated fluorescent protein driven micelle to which the target peptide sequence of MCF-7 is bound.

The particle properties of the target peptide sequence-binding micelle were measured by a dynamic light scattering method as the same as used in the example 1 (see FIG. 11). In FIG. 11, the horizontal axis shows the particle size of the obtained micelle, and the vertical axis shows the percentage of in the micelle size in whole micelle size shown in horizontal axis. As a result, the particles having the particle size of about 100 nm to 200 nm were confirmed as the same as those in the example 1.

From the above, it was demonstrated that the fluorescent protein-binding micelles having the target peptide sequence formed the equivalent size micelle to those without the target sequence. Furthermore, it was estimated that both of the micelles obtained in the example 1 and the present example were associated fluorescent protein driving type micelle.

(Example 4) DDS Micelle/Liposome, Vesicle, Form Discrimination Experiment (1) Preparation of Basic Liposome or Micelle The liposome or micelle was prepared as described below. Firstly, GFP containing solution was concentrated by using 10 K Amicon filter (Amicon) at 14,000×g for 15 minutes, and then it was messed up to 99 μL with 1×PBS. In order to prepare 50 μM/50 μL of the micelle by using 20 μM GFP containing solution, 137.5 μL of GFP was concentrated.

Next, 1 μL of 100 mM DTT was added to the solution, and then incubated at room temperature for 10 minutes. Entire amount of the incubated solution was applied onto NICK column (GE Healthcare Japan), and 365 μL of 1×PBS was added. Further, 380 μL of 1×PBS was added, and then almost all of amount of the solution was recovered.

Next, 3.53 μL of 7.78 mM TPS (2, 3, 4, 5-tetra phenyl-1, 1-dimethyl silole) was added at 1:10 of molar ratio against GFP contained in the recovered solution. Then, the molecules in the solution was aggregated overnight at 37° C.

Next, entire amount of the solution, about 380 μL, which was aggregated overnight into 100 K Amicon filter, and then centrifuged at 14,000×g for 10 minutes to concentrate it. Then, about 30 μL was taken as a column upper fluid. 100 μL of 1×PBS was added to here, and then, it was centrifuged at 14,000×g for 10 minutes to wash the column. Washing operation was repeated 3 times and about 300 μL was collected.

After the centrifugation by using the desktop centrifuge at 14,000×g for 10 minutes, the column was inverted, and then the upper fluid on the column was collected. Proper quantity of 1×PBS was added to the emptied column, and diluted to 1.2 volume of the amount of interest with 1×PBS. The solution was equilibrated at 4° C. for 1 day, and diluted 20-fold to measure the particle size. Also, 80-fold dilution of the sample was measured by using Simadzu RF5300-PC at excitation wavelength of 370 nm, and measurement wavelength 488 nm (the range 3×5).

About 350 μL of the solution was taken from the solution, which was placed in 100 K Amicon filter and then centrifuged at 14,000×g for 10 minutes, as the lower fluid of the column. It was added to the washed solution as described above so as to the total amount, 650 μL. Then, it was diluted 20-fold for measuring the particle size. Also, 25-fold dilution of the sample was measured at excitation wavelength of 370 nm, and measurement wavelength 488 nm (the range 3×5). Obtained non-targeted type liposome or micelle was named as NSS25 or NSS26 respectively.

(2) Decided Results by Using the Electron Microscope

The particles were decided by using Low temperature and low vacuum scanning electron microscope (Hitachi High-technologies, Cat. No. S-3400N) whether it is the liposome or micelle. Observed particles are generally liposomes (vesicles). Segments are observed under the liquid nitrogen atmosphere.

Figure 12:
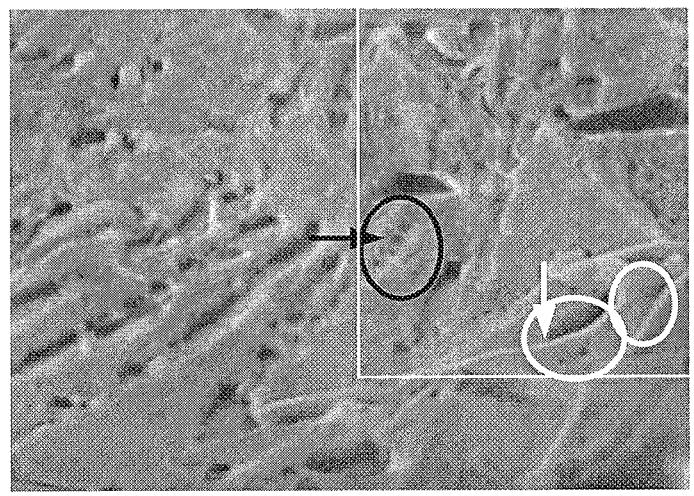
FIG. 12(A), FIG. 12(B) and FIG. 12(C) are electron microscope images to decide whether the formed particle were micelle or vesicles by using a low temperature and low vacuum scanning electron microscope.
Figure 12:
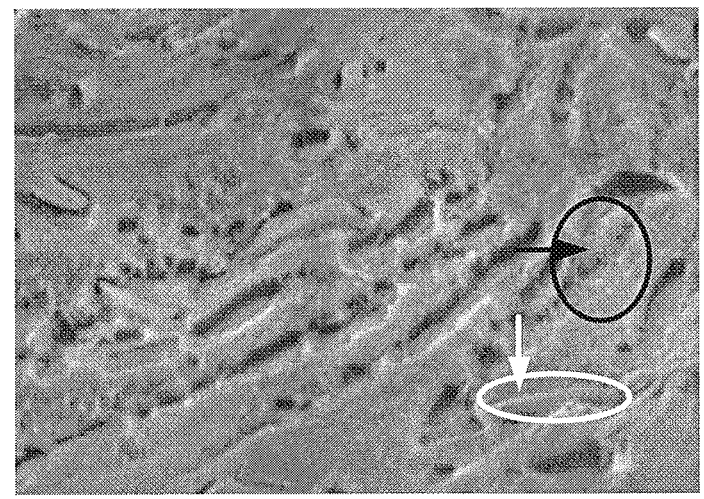
Figure 12:
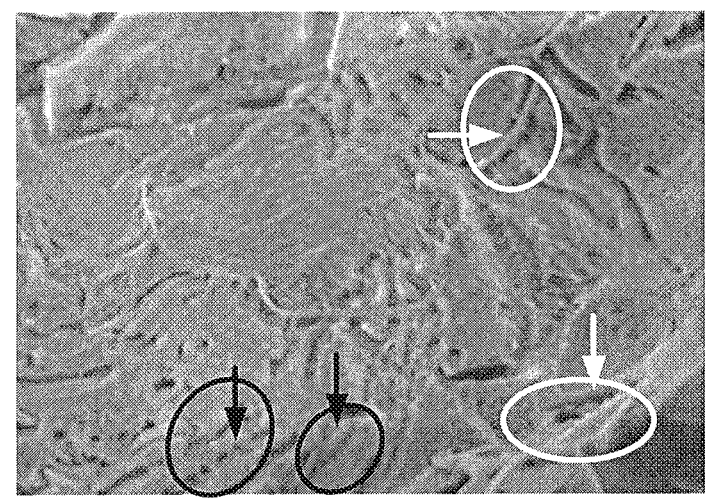

In the electron microscope, backscattered electron image of the incident electron beam was obtained as a BSE image, and secondary electron image is obtained as a SE image. Also, elemental analysis with X-ray is simultaneously conducted. BSE images are shown in FIGS. 12 (A) to (C). In low resolution images of SEM, the vesicle-like molecules were mainly observed. When the elemental analysis is conducted by using a portion of the sample, Si is detected in some particles (See, FIG. 12(A), FIG. 12(B) and FIG. 12(C)).

(Example 5) Dose-Dependent Stability Test of the Liposome, Vesicle, or the Micelle (1) Preparation of the Sample Micelle (the Micelle Having the Target Binding Site)

50 μM×50 μL of the sample micelle was prepared as described below. As the basic micelle, non-targeted type micelles (NSS25 and NSS26) prepared in Example 4 are respectively used at 16.1 μM and 3 16 μM. As the recognition site, 11.3 μM of the targeted type of the micelle (Seq. Nos. 12 and 13 of the sequence listing) including the sequence of the MCF7 is used.

The micelle solutions including respective liposomes or micelles are respectively placed in Amicon 10 K filters, and centrifuged at 14,000×g for 15 minutes to separately collect the supernatants. Each of the micelle solution is diluted to 99 μL of 1×PBS, 1 μM of 1 mM DTT is added and then stood at ambient for 10 minutes.

Next, each of the liposome or micelle solution is treated with NICK column, and 3.21 μL of TPS was added to the obtained treated solutions. Then, they are stood at 37° C. for overnight.

(2) Confirmation of the Dose Dependency of the Liposome (Vesicle) or Micelle

380 μL of the each solution obtained as described in (1) is placed in Amicon 100 K filter, and centrifuged at 14,000×g for 10 minutes. Since about 350 μL is dropped through the filter, it is used as the lower fluid, and about 30 μL of the solution remained on the filter was used as the upper fluid.

The upper fluid is kept as is, and then 100 μL of 1×PBS is added and then centrifuged at 14,000×g for 10 minutes to recover about 100 μL of the solution pass-through the filter. The operation is repeated for 3 times, and obtained solution is combined with the lower fluid. The combined solution is diluted 20-fold for measuring DLS (particle size distribution) as the same as that of the basic micelle.

The filter containing the upper fluid was centrifuged by using the desk top centrifuge (Kubota corporation) for a couple of minutes to recover the upper fluid. Then, proper amount of 1×PBS was added to the emptied filter and stood for 10 minutes. After that, the filter is inverted and centrifuged for a couple of minutes to recover the solution inside the filter. Then, the recovered solution is diluted with 1×PBS to 60 μL to set as a stock (1×) of 50 μM/50 μL.

The stock is diluted with 1×PBS to 5-fold, 10-fold, and 50-fold, and stood 1 day at ambient for equilibration. After that, as the same as that of the basic micelle, both of the particle size and fluorescence are measured. It was shown that there is the possibility for stable existence of the micelle prepared not less than critical micelle concentration 1 month later.

(Example 6) Physical Property Evaluation of Structural Protein for the DDS Micelle (1) Purification of the Peptide In order to evaluate structural protein for the DDS micelle, the structural protein is purified according to the following procedures by using Ni NTA Super flow (Qiagen).

(1-1) Elution of the Peptide from the Aggregatable Molecules

Firstly, 50 μL of the basic micelle (50 μM/50 μL) is taken and placed in a 50 mL Falcon tube (Falcon). The basic micelle is washed with 20 mM imidazole, and then 250 mM imidazole is added. They are reacted overnight in the rotary shaker for the elution of the peptide. The Falcon tube is set in the centrifuge (Kubota corporation), and centrifuges at 12,000 rpm for 10 minutes. The obtained supernatant is transferred to 15 mL Falcon tube.

(1-2) Preparation of Ni NTA Resin Slurry

During the centrifugation of the Falcon tube described above, Ni NTA resin (contained in Ni NTA Super flow) is prepared. Firstly, 2.5 mL of Ni NTA agarose is taken, and an antiseptic is removed. Next, the solution containing Ni NTA agarose gel is shaken well to mix homogenously, and then moved into a 15 mL Falcon tube.

After that, the solution is centrifuged at 1,000 rpm by using the desktop centrifuge to precipitate the gel, and the supernatant is removed by using a pipette. Then, 1 mL of 1×PBS is added, and then the tube is shaken and vortexed. The procedure is repeated 3 times, and after the third centrifugation, the supernatant is removed by using the pipette to prepare the slurry. It is stored except an amount to be used at 4° C.

(1-3) Purification of Each Peptide

400 μL of the slurry is dropped to the structure protein solution in the 15 mL Falcon tube, paying attention not so as to touch inside wall thereof. After that, the tube is set to the rotary shaker of which dial is set to maximal and shaken for 10 minutes for reacting.

Next, the tube is taken out from the shaker, and centrifuged at 1,000 rpm for 1 minute by using a centrifuge for animal cells (Taitec) to discard the supernatant. 4 mL of 1×PBS is added to the pellet in the tube bottom, and then vortexed. The tube is centrifuged at 1,000 rpm for 1 minute. The procedure is repeated twice.

4 mL of 20 mM imidazole is added to the obtained pellet, and centrifuged at 1,000 rpm for 1 minute by using the centrifuge. The procedure is repeated twice. Next, 500 μL of 250 mM imidazole is added to the obtained pellet, the tube was set to the rotary shaker of which dial is set to maximal and shaken for 10 minutes for reacting. Next, the tube is taken out from the shaker, and centrifuged at 1,000 rpm for 1 minute by using a centrifuge for animal cells. Then, the supernatant is transferred to a fresh 15 mL Falcon tube.

250 mM of imidazole is again added to the pellet in the old tube, which is set to the rotary shaker of which dial is set to maximal and shaken for 5 minutes for reacting. Next, the tube is taken out from the shaker, and centrifuged at 1,000 rpm for 1 minute by using a centrifuge for the animal cells. The supernatant is combined that already taken. The procedure is repeated 5 times.

(1-4) Gel Electrophoresis

Each peptide thus purified described above (GFP) is subjected to gel electrophoresis as follows.

Firstly, about 10 μL of the solutions containing 5 μM of each peptide are prepared and placed in each tube with a lid. As the molecular weight marker, ladder, 10 μL of Precision Protein Standards Prestained Broad Range (BioRad) is also added in to the 15 mL tube. Running gel (12%) having the composition shown in the following Table 13 and stacking gel (4%) having the composition shown in the following Table 14 are prepared.

TABLE 13

| Composition | Amount |
| --- | --- |
| ×4 Running buffer | 2.5 mL |
| 40% acrylamide gel solution containing 19:1 bis-acrylamide-acrylamide gel) | 3.12 mL |
| 10% APS | 50 μL |
| TEMED (Tetra methyl ethylen diamine) | 50 μL |
| Distilled water | balance |
| Total | 10 mL |

TABLE 14

| Compositions | Amount |
|---|---|
| ×4 Stacking buffer | 1.25 mL |
| 40% acrylamide gel solution containing 19:1 bis-acrylamide-acrylamide gel) | 0.5 mL |
| 10% APS | 25 μL |
| TEMED (Tetra methyl ethylen diamine) | 6 μL |
| Distilled water | Remains |
| Total amount | 5 mL |

Each purified protein solution and the molecular weight marker are applied to the gel, and electrophoresed for 60 minutes at 200 V and 20 mA, and then further electrophoresed for 75 minutes. The phoresis buffer having the composition shown in the following Table 15 is used.

TABLE 15

| Compositions | Amount |
|---|---|
| 2.5 mM tris (2-amino-3-hydroxymethyl-1, 3 propane diol) | 3.03 g |
| 192 mM glycine | 14.4 g |
| 01% SDS | 1 g |
| Distilled water | balance |
| Total Amount | 1,000 mL |

Figure 19:
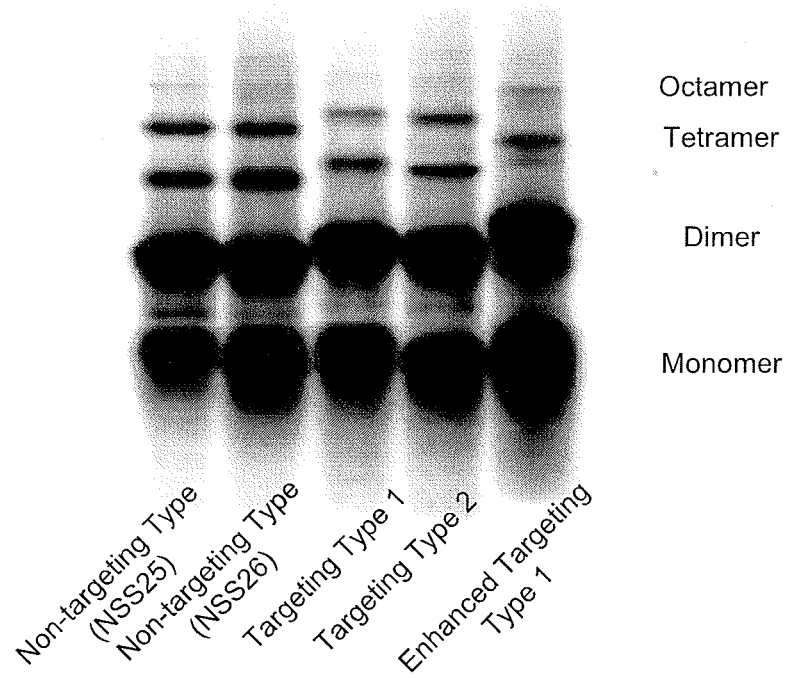
FIG. 19(A) and FIG. 19(B) are gel-electrophoresis images showing gel-electrophoresed protein which is composed of the shell.
Figure 19:
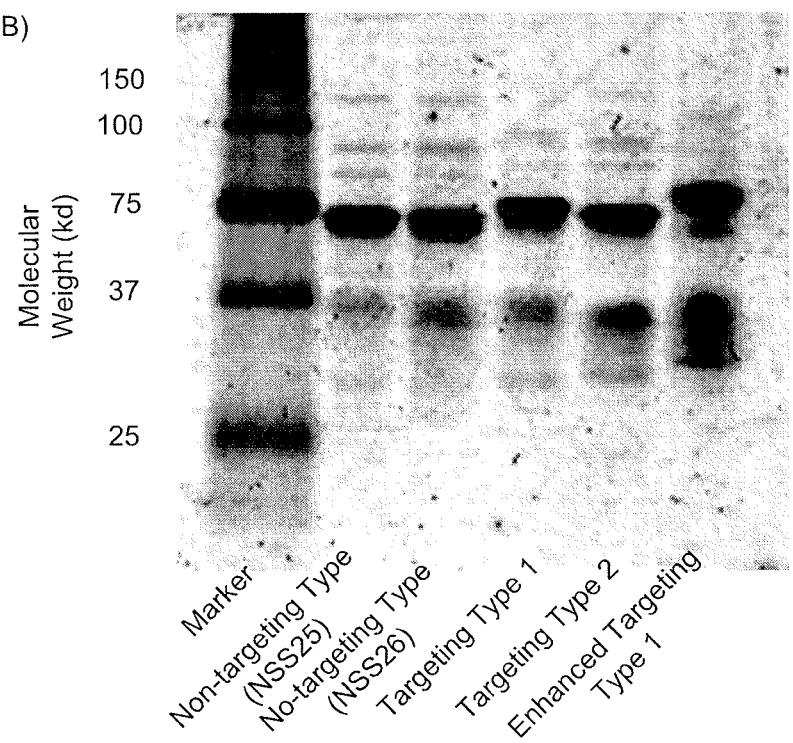

Results were shown in the FIG. 19(A) and FIG. 19(B). FIG. 19 (A). is the result before staining, and FIG. (B) is that after staining by using Coomassie Brilliant Blue (CBB). From the results of the gel electrophoresis, it was shown that the targeted type 2 (MCF7-2) has a tight cage-like structure composed of the dendrimer so that it has high fluorescent intensity but low targeted property. It was also shown that the type 1 enhanced (MCF7-1+α stand) has loose cage-like structure so that it has high targeted property but low fluorescent intensity.

As described above, it was shown that both of the tightness of the cage-like structure and the structure of the recognition site are important.

(Example 7) Inclusion Experiment of the Drug into the Liposome or Micelle for DDS As the drug included, Orange OT was employed. The solution containing 80 μM GFP is used, and the micelle solution is prepared as the same procedure for the basic micelle preparation except 10.28 μL of 7.78 mM TPS is added. Then, one μL of Orange OT (8 mM Orange OT stock solution) is added so as to become 1:1 at molar ratio (final conc.) against GFP. Next, DiI 282 (400 μM DiI 282 stock solution) is added so as to become 20:1 at molar ratio (final conc.) against GFP for overnight incorporation thereof at 37° C.

Next, the upper fluid of the column is diluted with 1×PBS to 1.2-fold of the volume interested, and then it is passed through PVDF filter (pore size was 0.45 μm or 0.22 μm). Other that these, the upper fluid is recovered by using the same procedure as those employed for the preparation of the basic micelle, and then it is subjected to the measurements for the particle size and fluorescent intensity. The upper fluid was treated as the same procedure employed for the preparation of the basic liposome or micelle, and then it was subjected to the measurements for the particle size and fluorescent intensity. It was considered that either of the drug, hydrophobic or hydrophilic, but optimization for the micelle formation conditions for respective cases was necessary.

(Example 8) Evaluation for Incorporating the Liposome or Micelle for DDS (1) Experimental Procedure Confluent MCF7 cells are peeled off by using 0.25% trypsin solution to prepare cell suspension ($1 \times 10^9$ cells/mL). Three mL of the cell suspension is plated into 5 collagen coat dishes (MatTek) or poly-d-lysine dish (MatTek).

After the cells are attached onto the bottom surface of the well, the medium is removed by using the pipet. Proper amount of DMEM (+) is added to the wells, and washed 3 times not so as to release the attached cells.

450 μL of DMEM (+) is added into each well of the collagen coat dishes for observation at 3 hours or 24 hours. Next, 50 μL of 1×PBS is added into the negative control wells. 50 of the sample 1 composed of 7.3 μL of enhanced type 1 of the stock solution and 42.7 μL of 1×PBS is added into each well of 2 dishes. The sample 2 composed of 8.4 μL of non-targeted type stock solution and 41.6 μL of 1×PBS is added into each wells of other 2 dishes.

In the negative control wells of the poly-d-lysine dish, 50 μL of 1×PBS is added. Also, the sample 2 composed of 8.1 μL of the non-targeted type (NSS26) stock solution and 41.9 μL of 1×PBS is added into one dish for the observation at 24 hours. Immediately after that, the plate is photographed, and then incubated at 37° C. in the presence of 5% $CO_2$ for 3 hours or 24 hours. After terminating the incubation, 1 mL of DMEM (+) is added into the wells to wash the cells. The washing was repeated 3 times.

(2) Observation Results by Using Confocal Microscope FV-100 (Olympus, FV 1000 D)

DAPI is excited with a laser beam having 405 nm and observed the emission light of 460 nm to observe the dendrimer parts. Also, GFP parts are observed by using the emission light having 515 to 520 nm. Observation results are shown in FIGS. 20A to 20C. Compared to the results at 3 hours (FIG. 20(C) upper column) and these of 24 hours (FIG. 20(C) lower column), it seemed that the targeted micelles were properly incorporated into the targeted cells even in 24 hours (see, FIGS. 16 to 18).

Figure 16:
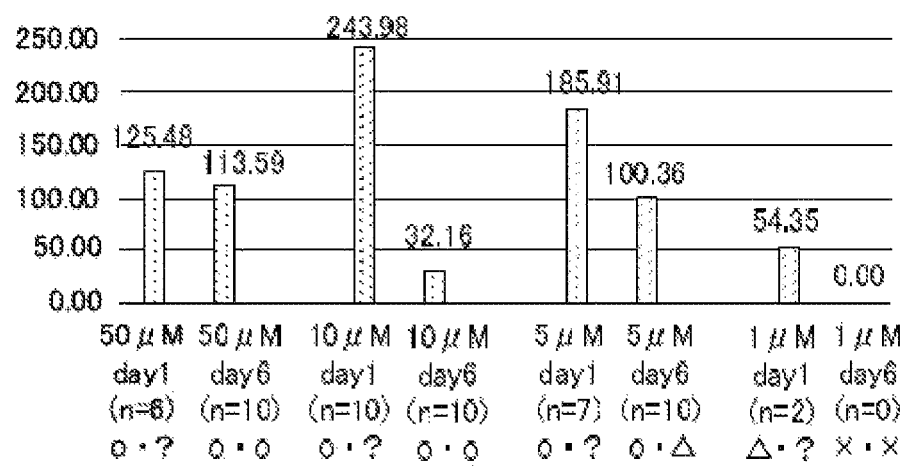
FIG. 16(A) and FIG. 16(B) show the graphs for time-dependent change or time-dependent change of the non-targeted micelle.
Figure 16:
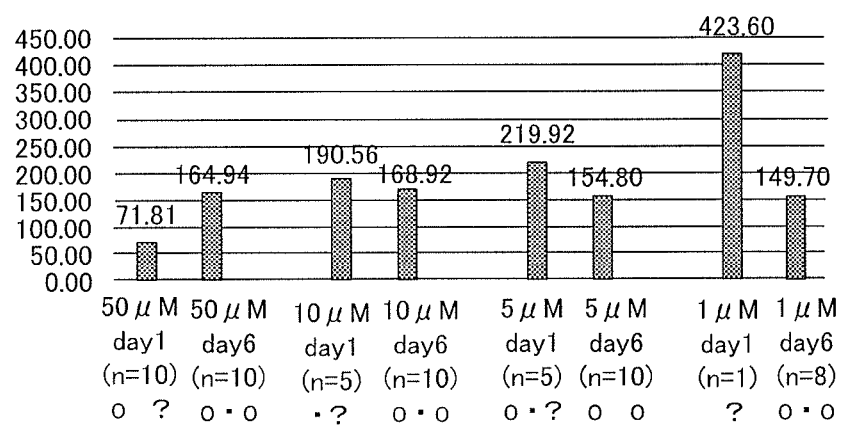
Figure 17:
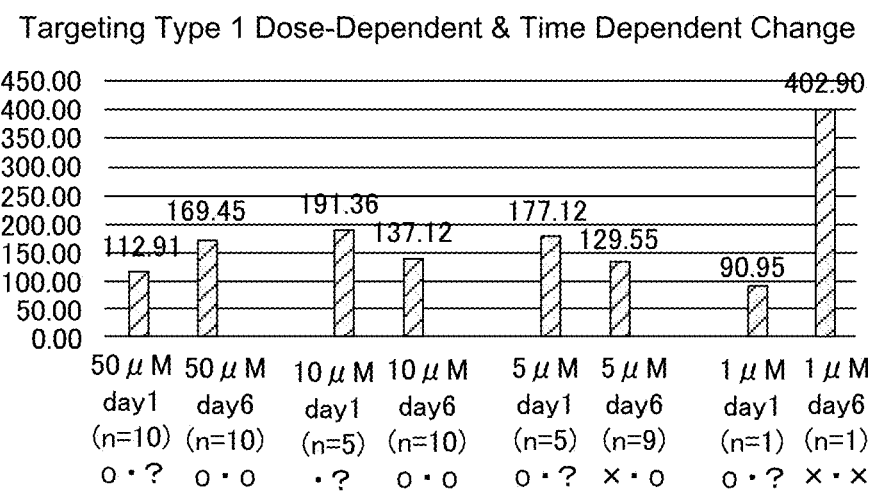
FIG. 17 shows the graphs for time-dependent change or time-dependent change of the targeted type 1 micelle.
Figure 18:
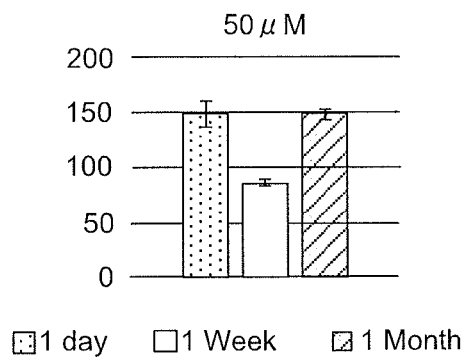
FIG. 18(A), FIG. 18(B) and FIG. 18(C) show the graphs for time-dependent change of the non-targeted micelle or targeted micelle.
Figure 18:
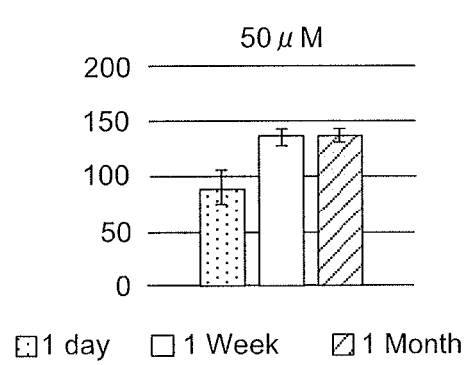
Figure 18:
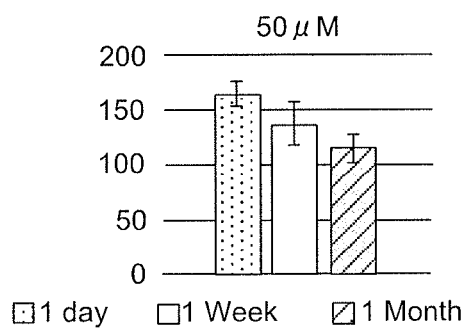

Both of FIGS. 16 (A) and 18 (A show results, when the non-targeting type (NSS25) were used, and both of FIGS. 16 (B) and 18 (B) show these, when the targeting type (NSS26) were used respectively. FIG. 18 (C) shows the result, when the targeting type 1 micelle was used.

(3) Analysis Method

As the analysis software, Image J is used. Fluorescent intensities in each area are expressed in numerical forms, and the fluorescent intensity ratio of the micelle and the protein was obtained. On the basis of the ratio, degradation of the micelle and remained fluorescent protein were confirmed.

For the analysis software for FACS measurement, FlowJo was used. For the analysis, sole cell data was used and cell population having auto fluorescence was chosen. Also, the cell population having auto fluorescence was subtracted from all of the data. Results were shown in FIGS. 13 to 15.

Figure 13:
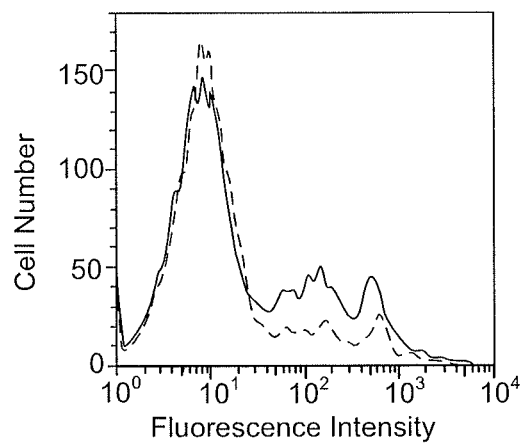
FIG. 13(A), FIG. 13(B), FIG. 13(C) and FIG. 13(D) are graphs showing the incorporation of a targeted protein and a micelle including the targeted protein into MCF7 cells.
Figure 13:
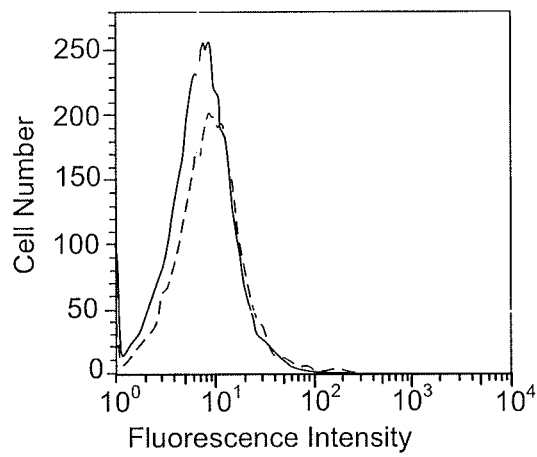
Figure 13:
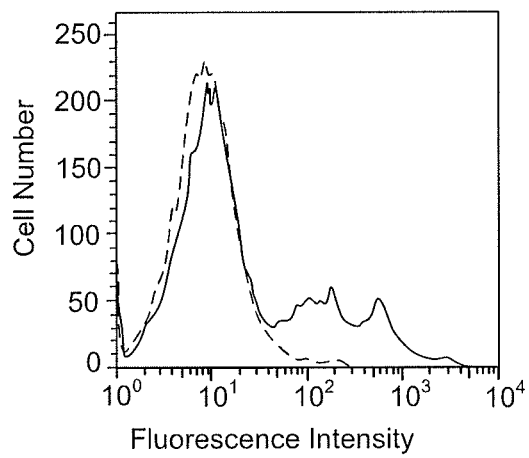
Figure 13:
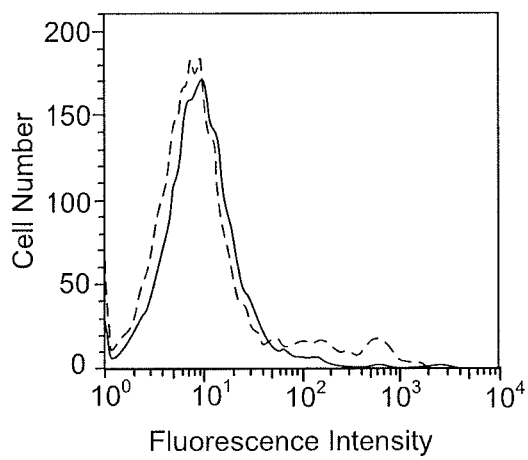

FIG. 13 (A) shows the incorporation both of the HepG2 targeting type 1 protein (−)(−) and MCF7 targeting type 1 protein (−)(−). FIG. 13 (B) shows that of HepG2 targeting type 1 protein (+)(+) and MCF7 targeting type 1 protein (+)(+). FIG. 13 (C) shows that of HepG2 targeting type 1 micelle (−)(−) and MCF7 targeting type 1 micelle (−)(−).

FIG. 13 (D) shows that of HepG2 targeting type 1 protein (+)(+) and MCF7 targeting type 1 protein (+)(+).

FIG. 14 (A) shows the result without use of the micelle; both of FIGS. 14 (B) and (C) show these by using the non-targeting type micelle; both of FIGS. 14 (D) and (E) show these by using the targeting micelle. The micelles used in FIGS. 15 (A) to (E) were the same as those used in FIG. 14(A) to (E). In the Figure, the numerical is the cell number after subtraction of that having auto fluorescence from that of the all of the cells measured/total cell number measured. The following Table 16 shows the determination results of five cell population having the auto fluorescence, and means thereof.

TABLE 16

| Incorporation into 151224 MCF7 Cell | % | FACS data Mean of 5 times background | 19.58 % |
|---|---|---|---|
| Hep G2 target type I Protein (−)(−) | 14.62 | MCF7 target type I Protein (−)(−) | 15.21 |
| Hep G2 target type I Protein (+)(+) | 12.69 | MCF7 target type I Protein (+)(+) | 8.88 |
| Hep G2 target type I micelle (−)(−) | 1132 | MCF7 target type I micelle (−)(−) | 15.13 |
| Hep G2 target type I micelle (+)(+) | 12.85 | MCF7 target type I micelle (+)(+) | 13.41 |

As described above, it was shown that the targeted was occurred under the good cell condition, and long term contact of the micelle to the cell makes general endocytosis even for the non-targeted micelle and they were incorporated large amount. However, there is the possibility that the incorporation of the targeted micelle is rapidly incorporated in to the cells than the non-targeted ones. Also, the incorporated micelle may be destructed in the cells.

(Example 9) Aggregated Fluorescent Protein Driven Micelle Formation in Tris HCl Buffer Tris HCl buffer is used instead of PBS, which was used for the micelle formation in Example 1, for producing a fluorescent protein driven micelle. Firstly, the targeting peptide sequence binding fluorescent protein solution containing 50 µM of the peptide sequence shown as Sequence No. 1 prepared in Example 2 is prepared, the peptide is sometimes referred to as "MCF7-1 fluorescent protein". 219.2 µL of the solution is concentrated by using 10K Amicon filter column (Amicon), and then it is centrifuged at 14,000×g for 15 minutes to concentrate, and then 50 mM Tris HCl buffer (pH 8.0) is added thereto so as to become the volume the volume of 99 µL.

Next, 1 µL of 100 mM DTT is added into the solution, and then the mixture is incubated for 10 minutes at ambient. Entire volume of the incubated solution (100 µL) is applied onto NICK column (GE Healthcare Japan), which is previously washed with 0.05 M Tris HCl buffer (pH 8.0) for 5 times, and then eluted with 365 µL of 0.05 µM Tris HCl buffer (pH 8.0). Further, 380 µL of 0.05 M Tris HCl buffer (pH 8.0) is added to the column, and almost all of the eluted solution is collected.

10.28 µL of 7.78 mM TPS (Yoyulabo Co., Ltd.) is added to the collected solution and stirs for 10 minutes. Then, the molecules in the solution are associated at 37° C. for overnight to prepare the reacted micelle solution. Thus obtained the micelle reacted solution is added to 100K Amicon filter column (Merck), and then it is centrifuged at 14,000×g for 10 minutes to concentrate. After that, 1×PBS is added to the upper solution of the column with the filter and centrifuged at 14,000×g for 10 minutes to wash it. The washing procedure is repeated for 3 times to exchange the buffer. About 300 µL of the washed solution is collected to obtain the unreacted micelle solution.

100K Amicon filter column is inversed and then it is subjected to centrifugation by using the small size centrifuge to recover the upper solution of the column, purified micelle containing solution. Proper volume of 1×PBS is added to the emptied column and it is stood for 10 minutes. Amicon filter column is again inversed to be subjected to the centrifugation for collecting the solution. After that, 1×PBS is added to adjust the volume of the solution to 160 µL to obtain the purified micelle. In order to confirm the particle size of the obtained micelle and stability thereof in the solution, the following experiments were conducted.

The sample 1 for determination is prepared by diluting the obtained purified micelle solution for 20 times with 1×PBS; and the sample 2 for the determination is prepared by diluting that for 50 times with 1×PBS, respectively. The sample 3 for the determination is prepared by diluting the obtained unreacted micelle solution for 25 times with 1×PBS. These diluted solutions are stood for 4 days at ambient to study their stabilities in the solution.

Figure 21:
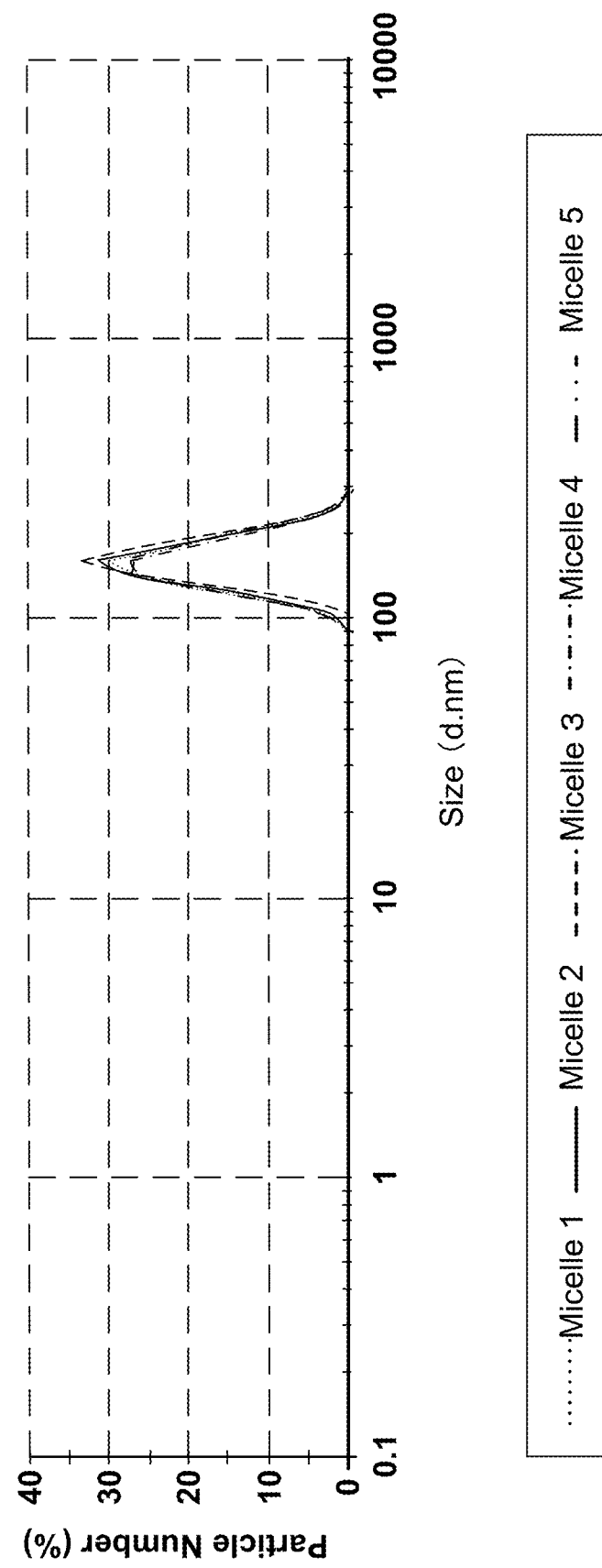
FIG. 21 is a particle size distribution chart of the micelle prepared by using Tris-HCl buffer, which is referred to as "the buffer" hereinbelow.

Particle size of the particle in the sample 1 is determined by using ZETASIZER NANO-S (Malvern Panalytical Ltd.). The result showed that uniform micelle having the particle size between about 100 to 200 nm (See, FIG. 21). Fluorescent spectrum of the particles in the sample 2 is measured by using RF5300-PC (Shimadzu Corporation) as the excitation wavelength at 370 nm and measurement wavelength at 488 nm. The spectrum of the particle in the sample 3 is measured by using the same conditions as those of the sample 2.

Figure 22:
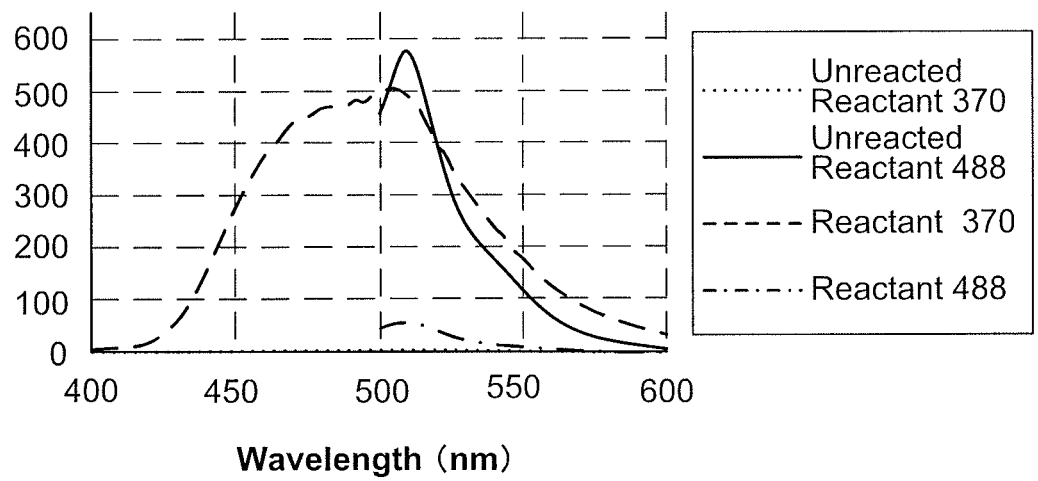
FIG. 22(A) and FIG. 22(B) are graphs showing the fluorescent spectrum of the micelle prepared by using the Tris-HCl buffer.
Figure 22:
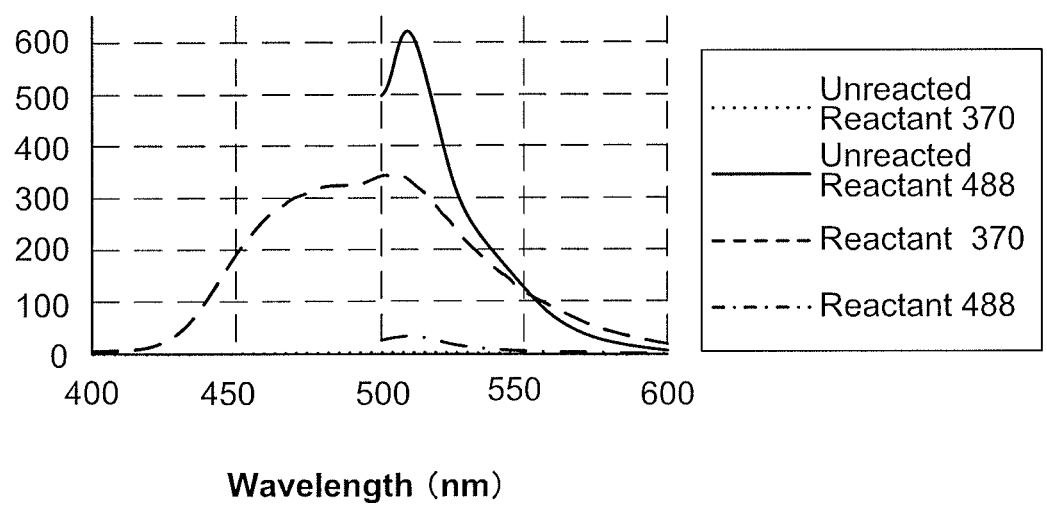

FIG. 22(A) shows the measurement results of the samples 1 to 3 when they are prepared. FIG. 22(B) shows them after 4 days from their preparation. In the figure, the unreacted reactant represents both of unbound MCF7-1 fluorescent protein and SD, and reacted one represents both of the bound MCF7-1 fluorescent protein and SD. Each numerical shows the wavelength of the excitation wavelength (nm). In FIGS. 22A and 22B, it was confirmed that the micelles, in which MCF7-1 fluorescent protein and SD are bound, were formed and the formed micelles were stably existing 4 days from their formation.

From the above, it was demonstrated that SD of the present invention formed the uniform and stable micelles by binding to GFP having the target presenting sequence even in Tris HCl buffer.

(Example 10) Aggregated Fluorescent Protein Driven Micelle Formation in HEPES Buffer The micelle formation, the particle size of the micelle formed and the stability thereof were confirmed under the same conditions as Example 9 other than 50 mM HEPES buffer (pH 7.6) was used instead of Tris HCl buffer (pH 8.0).

Figure 23:
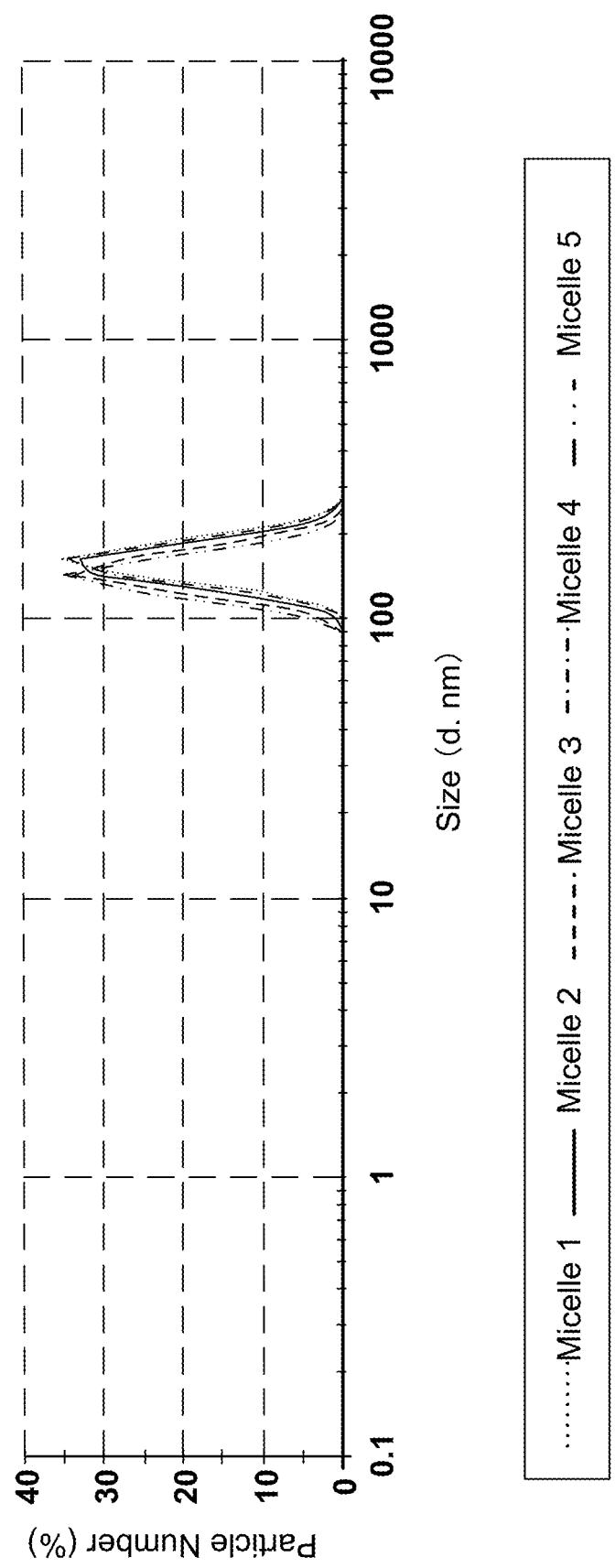
FIG. 23 is the particle size distribution chart of the micelle prepared by using HEPES buffer.
Figure 24:
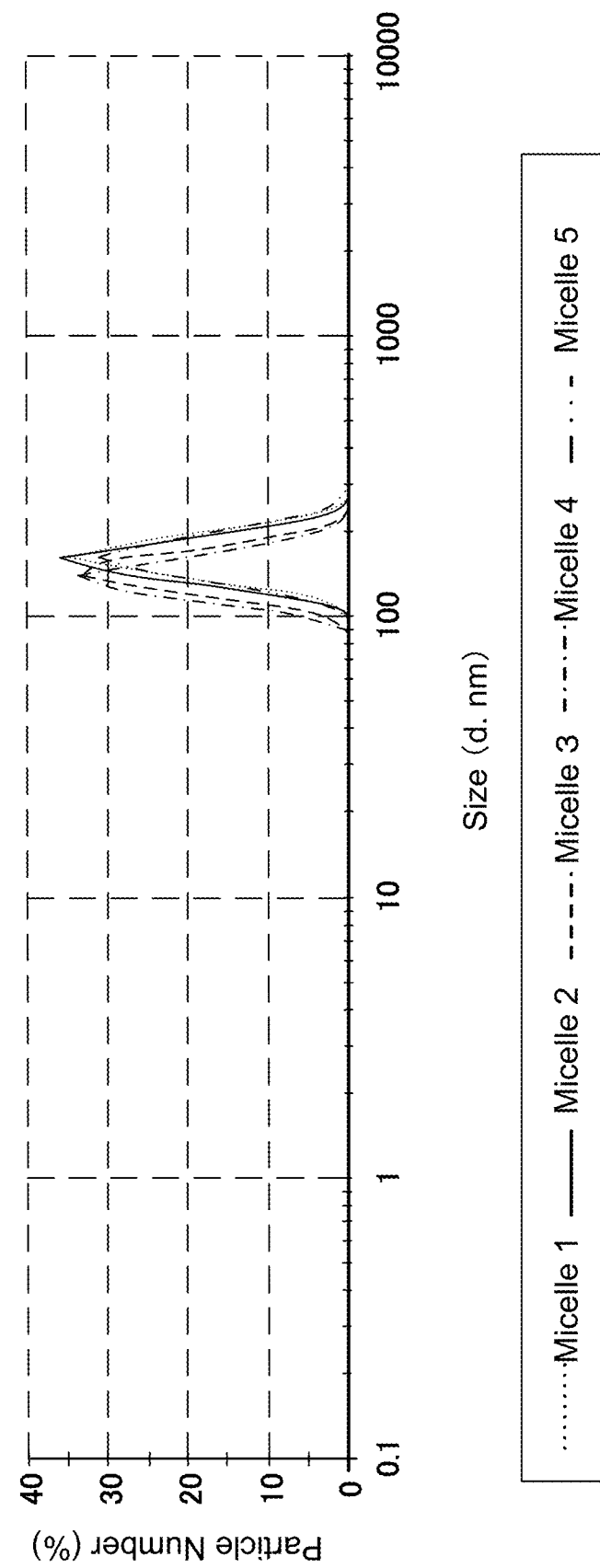
FIG. 24 is the particle size distribution chart of the micelle prepared by using HEPES buffer 1 day after the preparation.
Figure 25:
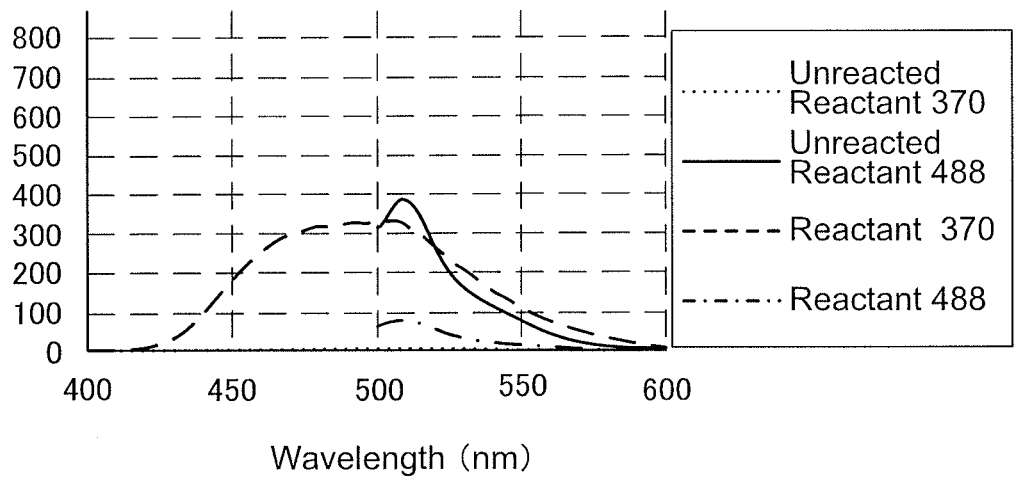
FIG. 25(A) and FIG. 25(B) are graphs showing the fluorescent spectrum of the micelle prepared by using the HEPES buffer.
Figure 25:
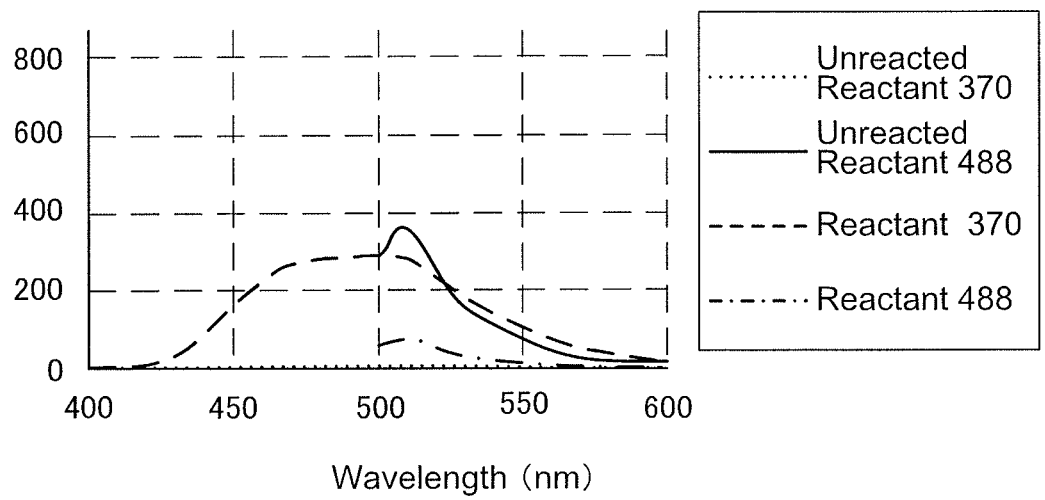

As shown in FIG. 23, the uniform micelle having the particle size from about 100 to 200 nm were formed. As shown in FIG. 24, the micelles formed were also stably existed 1 day after from the formation thereof. FIG. 25 (A) shows the measurement result at the formation of the micelle, and (B) shows that measured after 1 day from the formation.

As shown in FIGS. 25A and 25B, it was demonstrated that the micelles, in which MCF7-1 fluorescent protein and SD are bound, were formed and the formed micelles were stably existing 1 day from their formation.

From the above, it was confirmed that the uniform and stable micelles are formed in HEPES buffer instead of Tris HCl buffer.

(Example 11) Aggregated Fluorescent Protein Driven Micelle Formation in Sodium Citrate Buffer The micelle formation, the particle size of the micelle formed and the stability thereof were confirmed under the same conditions as Example 9 other than 50 mM sodium citrate buffer (pH 7.6) was used instead of Tris HCl buffer (pH 8.0).

Figure 26:
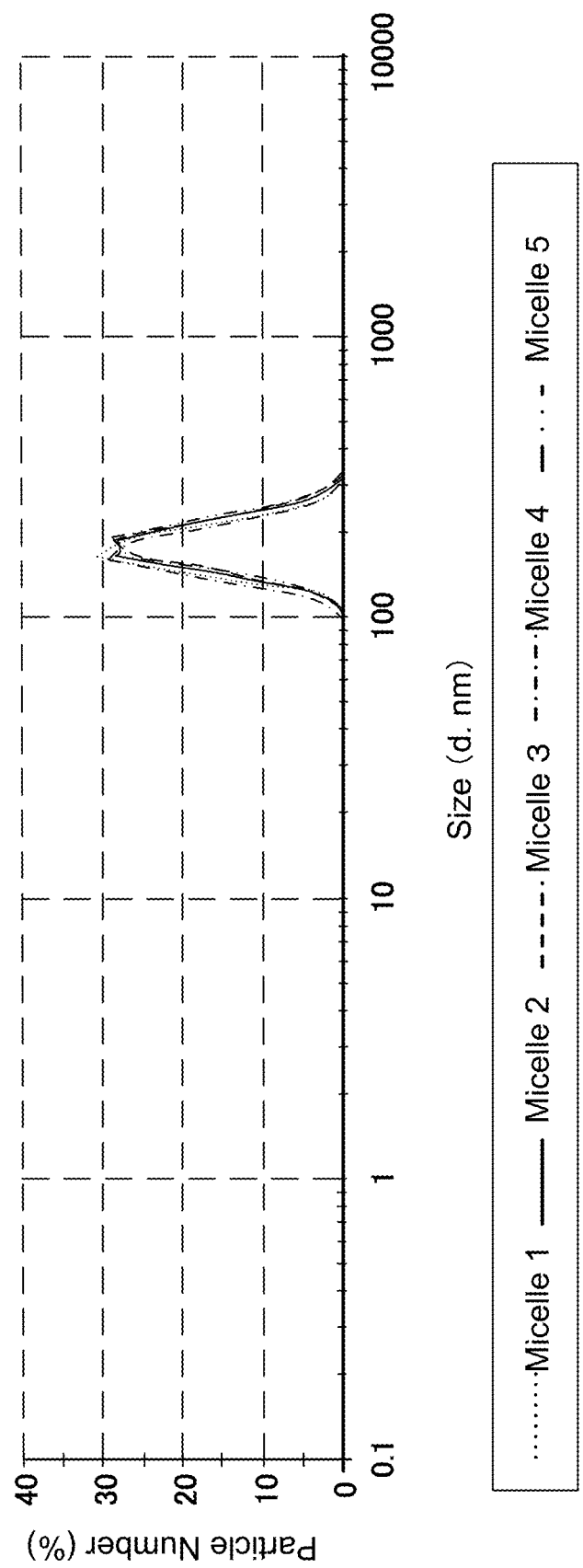
FIG. 26 is the particle size distribution chart of the micelle prepared by using sodium citrate buffer.
Figure 27:
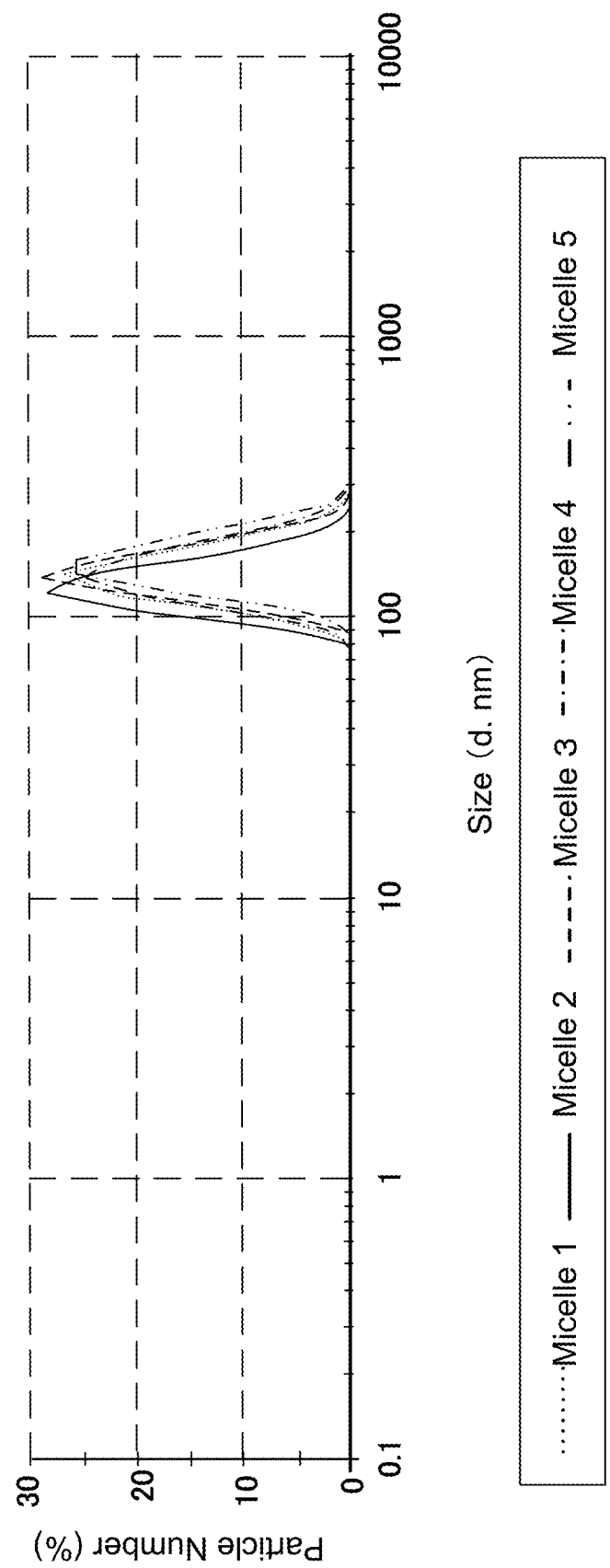
FIG. 27 is the particle size distribution chart of the micelle prepared by using sodium citrate buffer 1 day after the preparation.

As shown in FIG. 26, the uniform micelle having the particle size from about 100 to 200 nm were formed in the sodium citrate buffer. Also as shown in FIG. 27, the micelles formed were stably existed 1 day after from the formation thereof, because their particle sizes were kept almost the same as those at their formation.

Figure 28:
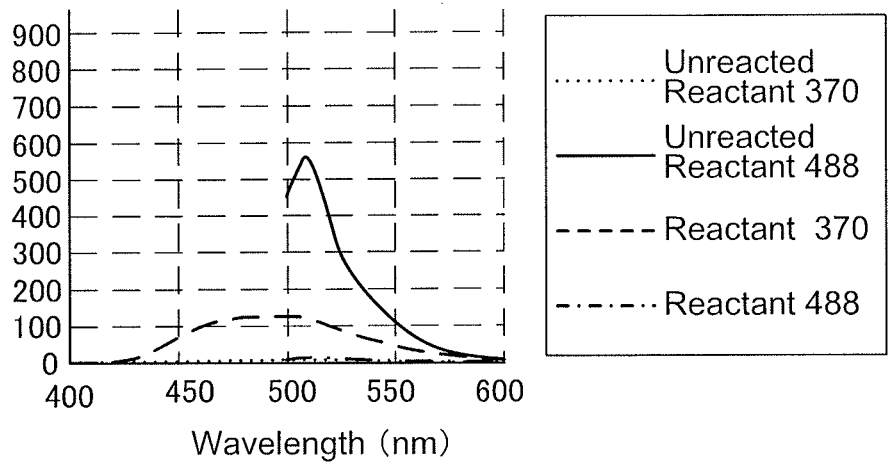
FIG. 28(A), FIG. 28(B) and FIG. 28(C) are graphs showing the fluorescent spectrum of the micelle prepared by using the sodium citrate buffer.
Figure 28:
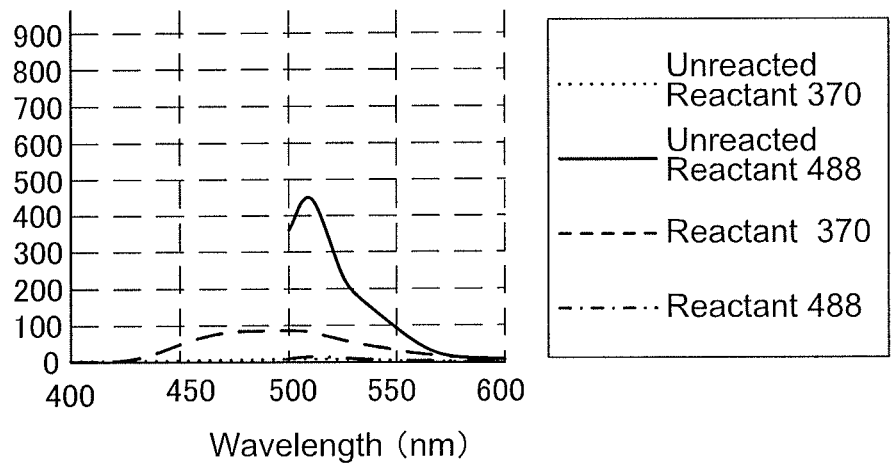
Figure 28:
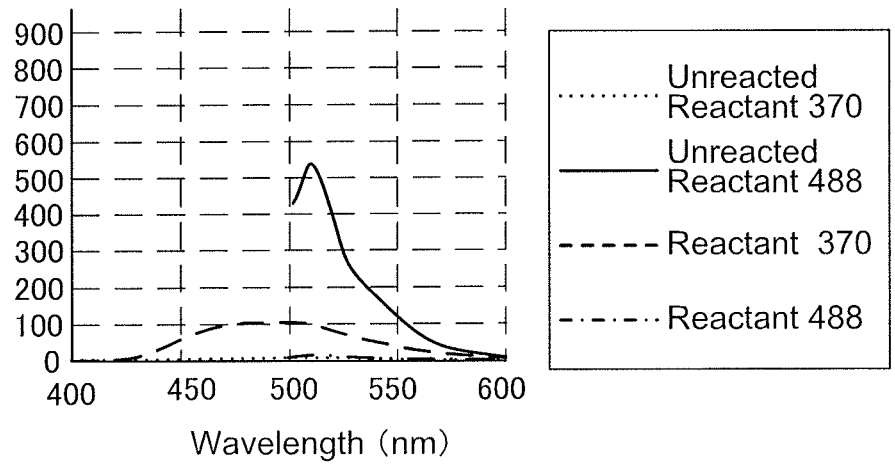

FIG. 28 (A) shows the measurement result at the formation of the micelle, and (B) shows that measured after 2 day from the formation. As shown in FIGS. 28 (A) to (C), it was demonstrated that the micelles, in which MCF7-1 fluorescent protein and SD are bound, were formed and the formed micelles, and were stably existing at least 2 days from their formation.

From the above, it was confirmed that the uniform and stable micelles are formed in sodium citrate buffer instead of Tris HCl buffer.

(Example 12) Aggregated Fluorescent Protein Driven Micelle Formation in Carbonate-Bicarbonate Buffer The micelle formation, the particle size of the micelle formed and the stability thereof were confirmed under the same conditions as Example 9 other than 50 mM carbonate-bicarbonate buffer (pH 8.0) was used instead of Tris HCl buffer (pH 8.0).

Figure 29:
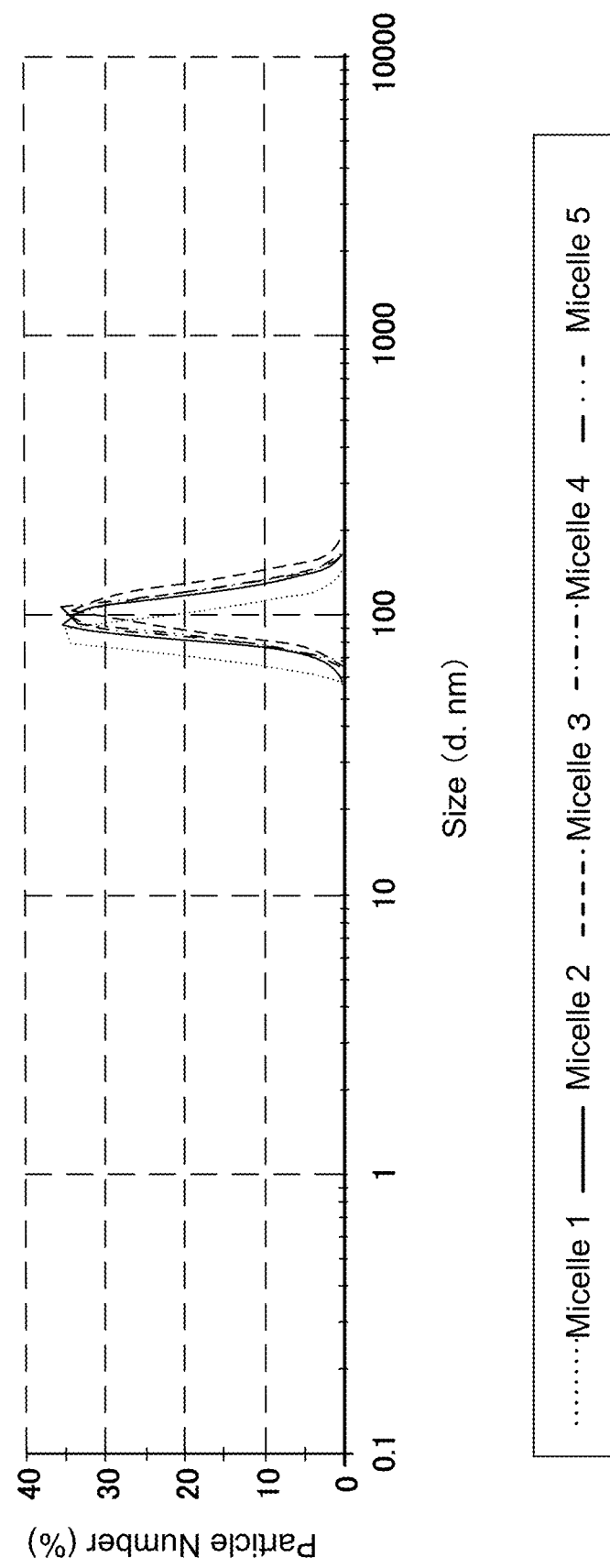
FIG. 29 is the particle size distribution chart of the micelle prepared by using carbonate-sodium carbonate buffer.
Figure 30:
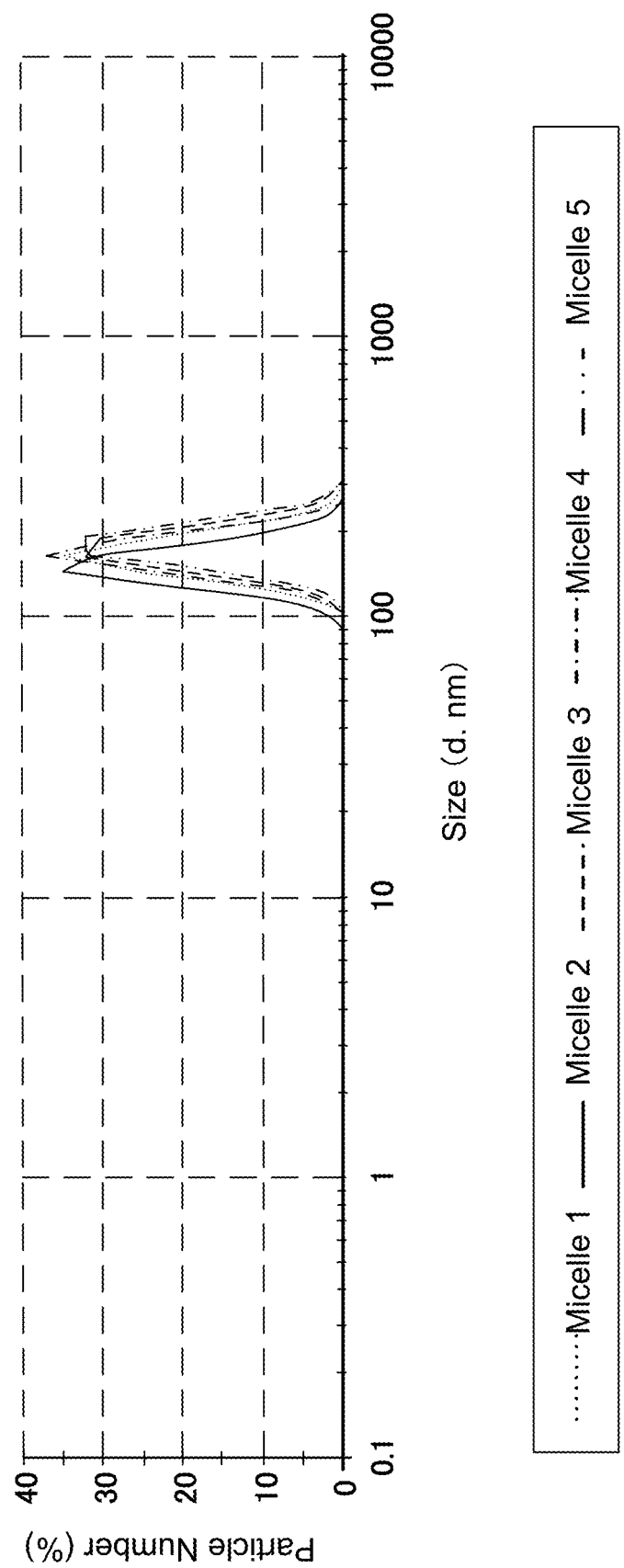
FIG. 30 is the particle size distribution chart of the micelle prepared by using carbonate-sodium carbonate buffer 1 day after the preparation.

As shown in FIGS. 29 to 30, it was confirmed that the uniform and stable micelles having the particle size from 100 to 200 nm are formed in carbonate-bicarbonate buffer instead of Tris HCl buffer. Also, it was confirmed that the particle sizes of the formed micelles were kept almost the same as those at their formation so that they were stably existing 1 day from their formation in the buffer.

Figure 31:
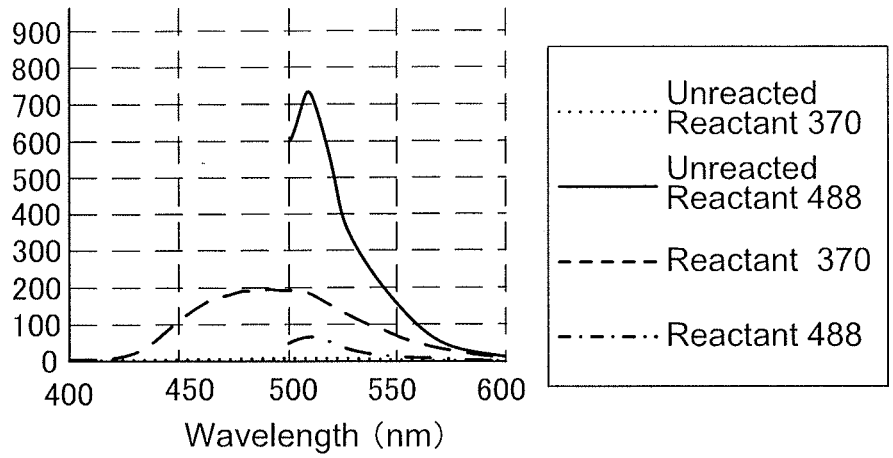
FIG. 31(A), FIG. 31(B) and FIG. 31(C) are graphs showing the fluorescent spectrum of the micelle prepared by using the carbonate-sodium carbonate buffer.
Figure 31:
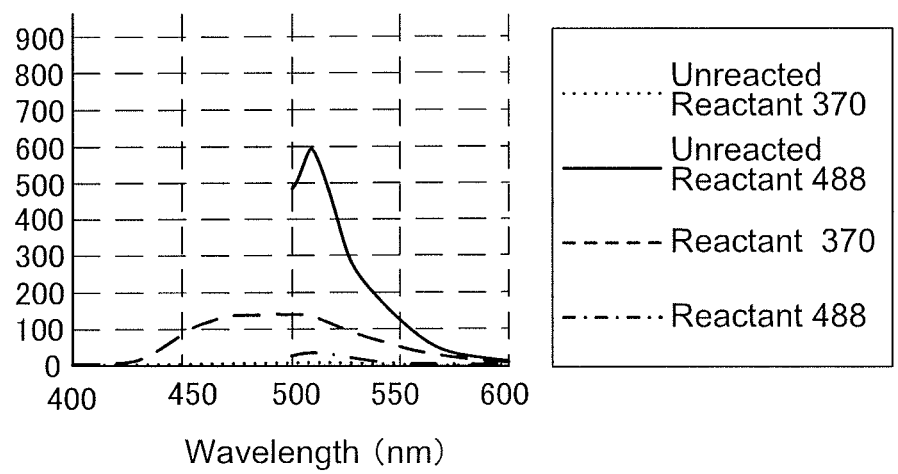
Figure 31:
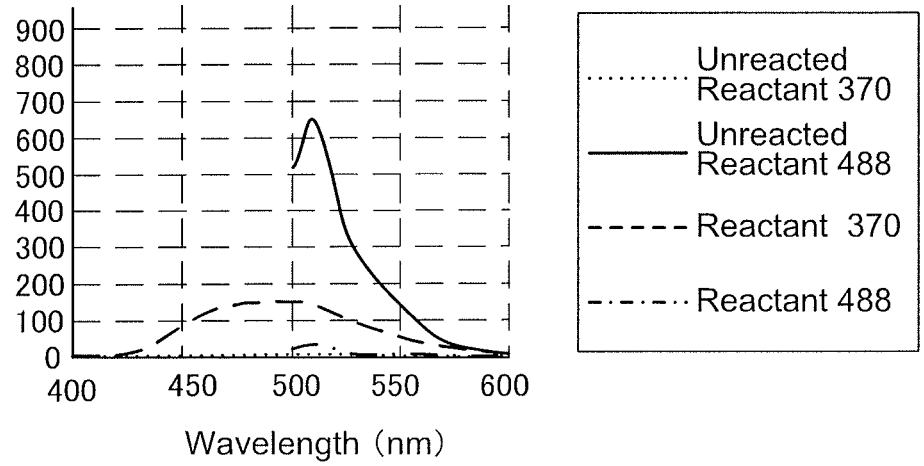
Figure 32:
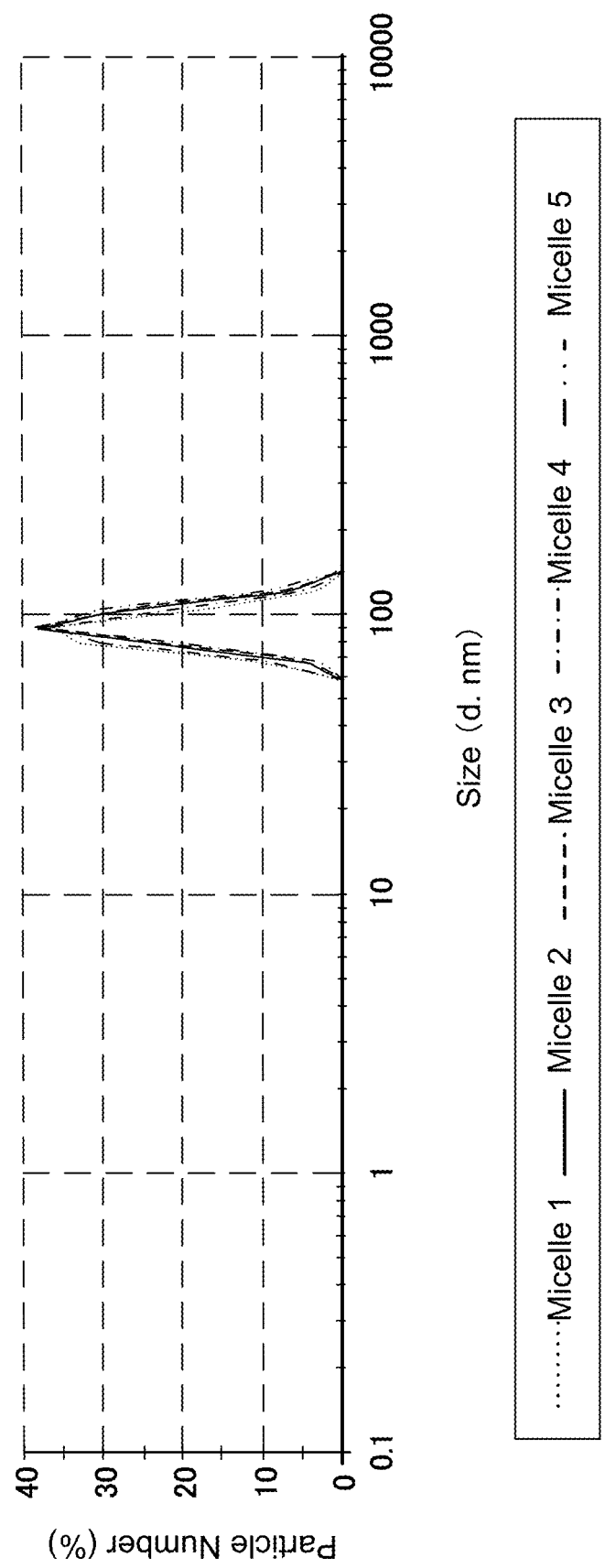
FIG. 32 is the distribution chart of the micelle after mixing in BSA-containing solvent.

FIG. 31 (A) shows the measurement result at the formation of the micelle, and (B) shows that measured after 1 day from the formation, and (C) shows that measured after 2 days form the formation. As shown in FIGS. 31 (A) to (C), it was demonstrated that the micelles, in which MCF7-1 fluorescent protein and SD are bound, were formed and the formed micelles were stably existed at least 2 days from their formation.

(Example 13) Affection of the Protein in a Dispersion Medium Against the Micelle In order to study the affection of a co-existing protein in vivo delivery against the formed micelle, in vitro experiment was conducted. As a model system thereof, the protein contained in the dispersion medium (BSA) against the formed micelle was studies time dependently. BSA was chosen, because it has the almost same molecular weight as that of GFP, is rich in blood, and easy to obtain.

Firstly, 50 μM of the fluorescent protein driven micelle is prepared in Example 3, which contains MCF7-1 as the target presenting sequence, hereinbelow, it is sometimes refers to as "MCF7-1 micelle", was employed. The micelle is concentrated by using 100K Amicon filter column to prepare 100 μM MCF7-1 micelle solution.

Subsequently, 100 μL of 4% BSA (SHIGMA-ALDRICH) is added into 200 μL of 100 μM MCF7-1 micelle solution to prepare BSA-micelle mixture, sample. Also, as a control, 100 μL of PBS instead of the micelle is added to prepare PBS-micelle mixture, reference. They were stored at 4° C. The particle sized and stabilities of these samples and the reference were confirmed under the same conditions as those of Example 9.

Figure 33:
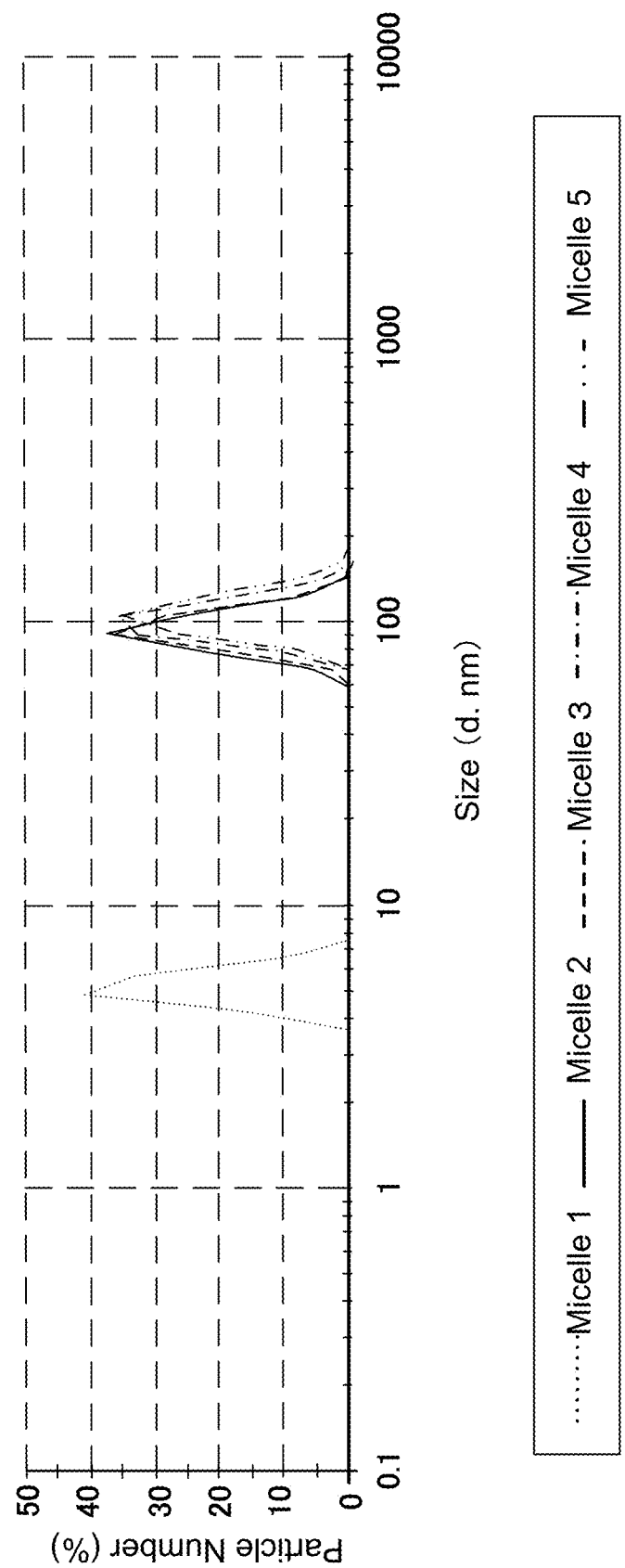
FIG. 33 is the distribution chart of the micelle stored for 6 days in the preparation at 4° C.

As shown in both of FIGS. 31 and 33, it was confirmed that the micelle having about 50 to 200 nm of the particle sizes are formed. Also, when they are stored at 4° C., the particle sizes of the micelle were kept even after 6 days. This shows that the micelles stably exist after 6 days from the preparation.

Figure 34:
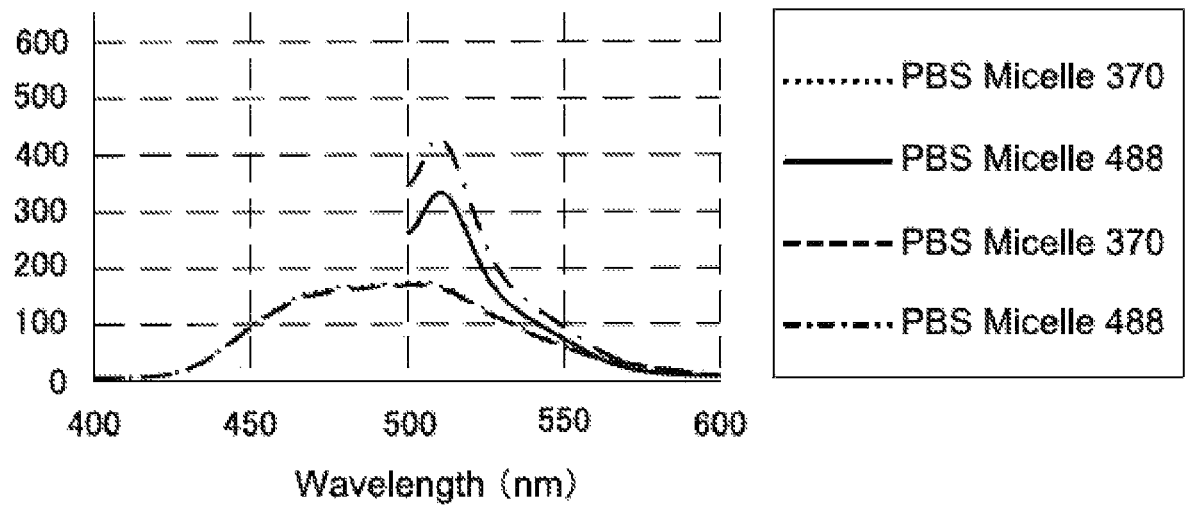
FIG. 34(A) and FIG. 34(B) are graphs showing the determination results of the fluorescent spectrum of the micelle, which is stored at 4° C. in BSA-containing solution.
Figure 34:
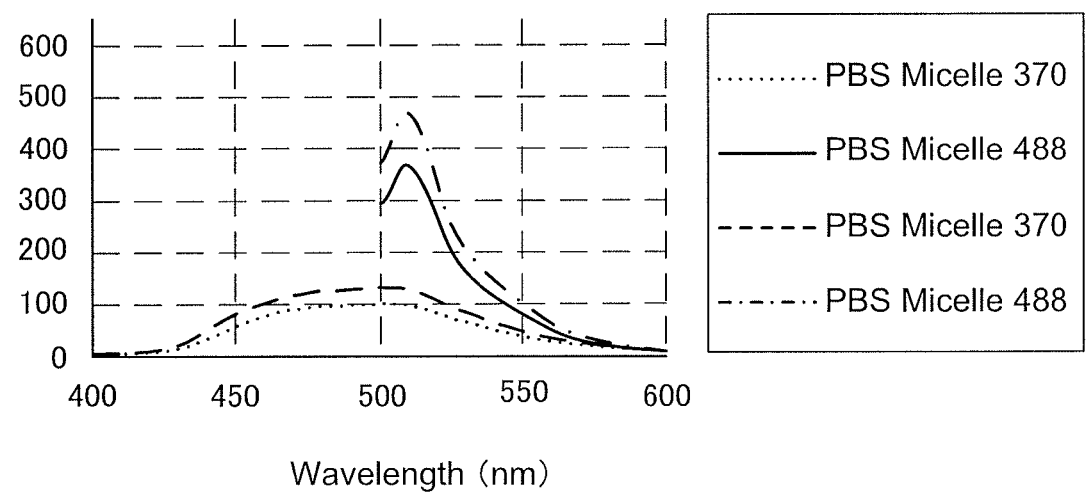

FIG. 34 (A) is a graph showing the measurement result at the starting of the storage, and (B) is the graph showing that of after 6 days storage. As shown in FIG. 34(A), any affection is observed for the conditions of the micelle even in the BSA-micelle mixture. As shown in FIG. 34(B), the fluorescent strength of the BSA-micelle mixture at 370 nm was rather higher than that of the PBS-micelle mixture. It was confirmed that there was no affection to the micelle condition 6 days after from the preparation or BSA was co-existing.

As described above, it was demonstrated that the micelle stably exists at least 6 days even if there are any proteins in the dispersion medium.

(Example 14) Study of an Incorporation Path of the Present Micelle into Cells

The incorporation path of the present micelle into cells was studied by using endocytosis inhibitor. Firstly, confluent MCF-7 cells are peeled off from the dish by using 0.25% trypsin solution to prepare cell suspension ($1 \times 10^9$ cells/mL). 15 mL of the cell suspension is plated into dished having 35 mm diameter, a 12 well connected plate.

After the cells are attached onto the bottom surface of the well, medium in each well are removed by using a pipette, and the attached cells are washed with proper volume of DMEM (+) not so as to peel off them. The washing operation is repeated for 3 times.

440 μL of DMEM (+) is added into each well. 1 mM Chlorpromazine (Wako Pure Chemical Corporation) prepared by using PBS, 500 mM methyl-β-cyclodextrin (Wako Pure Chemical Corporation) prepared by using DMSO or ethanol, and 1 mM cytochalasin B (Wako Pure Chemical Corporation) prepared by using DMSO or ethanol are respectively added into separate wells in 30 μL per each well, and then they are incubated at 37° C. for 30 minutes in the 5% $CO_2$ incubator.

After that, 50 μL of 50 μM MCF7-1 micelle prepared in Example 3 is added into each well, and then they are incubated at 37° C. for 6 to 7.5 hours in the 5% $CO_2$ incubator. After completion of the incubation, the cells are washed by adding 1 mL of DMEM (+). The washing operation is repeated 3 times.

Figure 35:
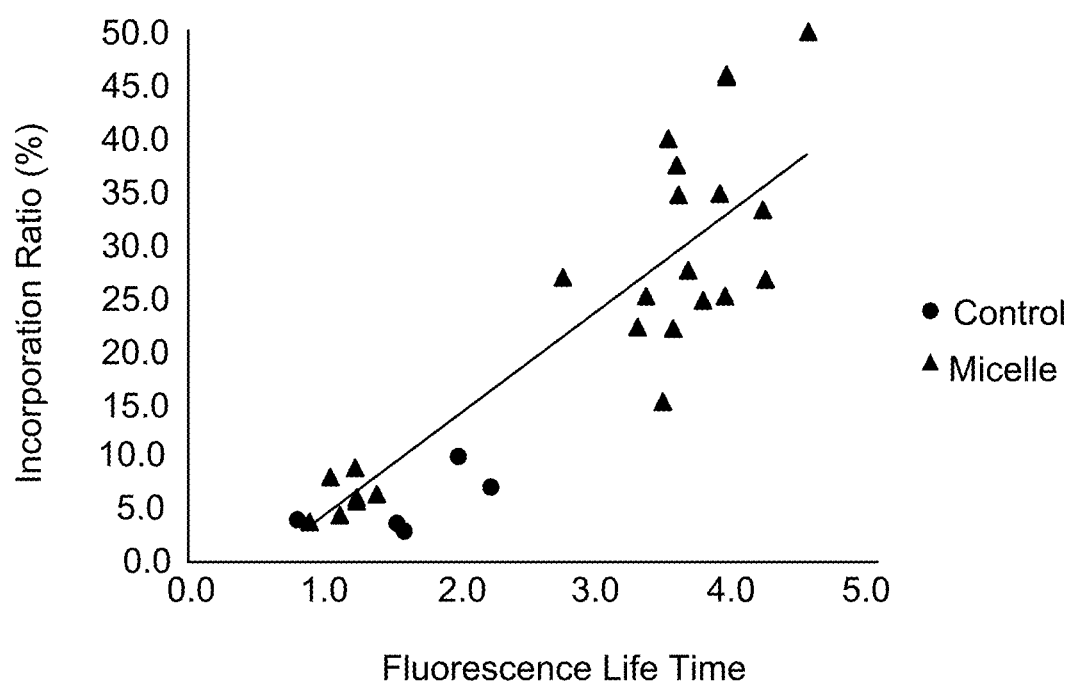
FIG. 35 is the graph showing the investigation results of the correlation between the incorporation ratio of the micelle into the cell and the fluorescence lifetime, when the MCF7 cells treated with an inhibitor and the micelle are incubated.

Correlation between incorporation ratio of the micelle into the cell and fluorescence lifetime was studied by using FACS. As shown in FIG. 35, it was demonstrated that there is a positive correlation between the cell incorporation ratio of the micelle and the fluorescent lifetime.

Also, in order to study of the affection by the solvent for measurement by using FACS, solution sets combined with the solvents used for the preparation of the inhibitor shown in Table 17 and the solvents used for measurements by using FACS are prepared.

TABLE 17

| Label | Solvents for the inhibitor | Solvents for FACS measurements |
| --- | --- | --- |
| I | PBS | PBS |
| II | DMSO | PBS |
| III |  | DMSO |
| IV | EtOH | PBS |
| V |  | DMSO |
| VI |  | EtOH |

Figure 36:
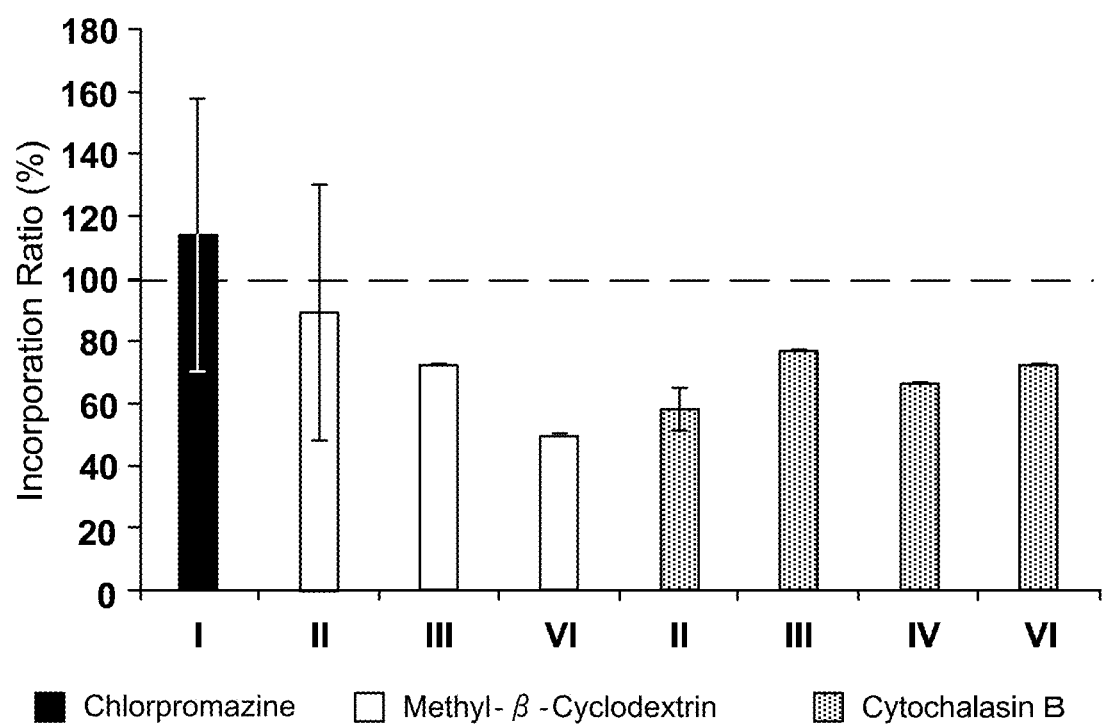
FIG. 36 is the graph showing the incorporation ratio of the micelle into the cell by using MCF7 cells treated with endocytosis inhibitor.

As shown in FIG. 36, the incorporation ratio of the micelle into the cells treated with methyl-β-cyclodextrin or cytochalasin B was under 100%, and it showed that the incorporation into the cell is inhibited. On the other hand, the incorporation ratio of the micelle into the cells treated with Chlorpromazine was over 100%, and it showed that the incorporation of the micelle into the cell was promoted.

From the above, it was demonstrated that the incorporation path of the micelle into the cell is any one of Caveolae endocytosis, Lipid raft endocytosis, phagocytosis or micropinocytosis.

INDUSTRIAL APPLICABILITY

The present invention is useful in the field of the pharmaceutical preparations, particularly in the field of drug delivery.

FREE TEXT FOR SEQUENCE LISTING

Seq. No. 1: Target recognition sequence peptide (MCF7-1) incorporated into GFP
Seq. No. 2: Target recognition sequence peptide (MCF7-2) incorporated into GFP
Seq. No. 3: Target recognition sequence peptide (MCF7-1+α stand) incorporated into GFP
Seq. No. 4: GFP incorporating MCF7-1
Seq. No. 5: GFP incorporating MCF7-2
Seq. No. 6: GFP incorporating MCF7-1+α stand
Seq. No. 7: amino acid sequence of GFP
Seq. No. 8: amino acid sequence of GFP
Seq. No. 9: amino acid sequence of BFP
Seq. No. 10: amino acid sequence of YFP
Seq. No. 11: amino acid sequence of the fluorescent protein derived from Discosoma
Seq. No. 12: forward primer for MCF7-1 amplification
Seq. No. 13: reverse primer for MCF7-1 amplification
Seq. No. 14: forward primer for MCF7-2 amplification
Seq. No. 15: reverse primer for MCF7-2 amplification
Seq. No. 16: forward primer for MCF7-1+α stand amplification
Seq. No. 17: reverse primer for MCF7-1+α stand amplification
Seq. No. 18: forward primer for inverse PCR
Seq. No. 19: reverse primer for inverse PCR
Seq. No. 20: forward primer for inverse PCR 用
Seq. No. 21: reverse primer for inverse PCR 用
Seq. No. 22: oligonucleotide
Seq. No. 23: oligonucleotide
Seq. No. 24: oligonucleotide
Seq. No. 25: oligonucleotide
Seq. No. 26: forward primer for inverse PCR
Seq. No. 27: reverse primer for inverse PCR
Seq. No. 28: forward primer for inverse PCR
Seq. No. 29: reverse primer for inverse PCR
Seq. No. 30: forward primer for inverse PCR
Seq. No. 31: reverse primer for inverse PCR
Seq. No. 32: forward primer for inverse PCR
Seq. No. 33: reverse primer for inverse PCR
Seq. No. 34: forward primer for inverse PCR

The invention claimed is:

1. An endocytosis enhancing agent being composed of an aggregatable molecule shown in formula (IV) comprising a target sequence presenting part, which is referred to as "TSPP" in the chemical formula (IV):

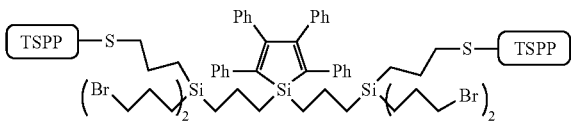

(IV)

wherein said target sequence presented part (TSPP) is composed of a fluorescent protein, and a protein or peptide for a target tissue specific delivery; and wherein said endocytosis enhancing agent comprises a space for containing an aqueous solvent or organic solvent inside of a capsule being composed of said aggregatable molecule, and said space encapsulates a protein having molecular weight of 200,000 daltons or less or peptide dissolved in said aqueous solvent, or a hydrophobic molecule dissolved in said organic solvent.

2. The endocytosis enhancing agent according to the claim 1, wherein the capsule has the diameter from 50 to 500 nm size.

3. The endocytosis enhancing agent according to the claim 1, wherein said aqueous solvent is selected from the group consisting of saline, phosphate buffered saline, Tris-HCl buffer, HEPES buffer, sodium citrate buffer, and carbonate bicarbonate buffer.

4. The endocytosis enhancing agent according to the claim 1, wherein said peptide specifically binds to a target protein selected from the group consisting of a surface antigen, a receptor, gate, a transporter and a channel.

5. The endocytosis enhancing agent according to the claim 1, wherein said peptide has any one of peptide having the sequence selected from the group consisting of: SEQ ID Nos. 1 to 3.

6. The endocytosis enhancing agent according to the claim 1, wherein said peptide has any one of peptide having the sequence selected from the group consisting of: SEQ ID Nos. 4 to 6.

7. The endocytosis enhancing agent according to the claim 1, wherein said target tissue is any one of tissue selected from the group consisting of the normal tissue having inflammation, the tissue including the cells having undesirable gene expressions, the tissue composed of the cells having undesirable gene expressions, and the tissue composed of tumor cells.

8. The endocytosis enhancing agent according to the claim 1, wherein said fluorescent protein is any one of selected from the group consisting of red fluorescent protein, yellow fluorescent protein, blue fluorescent protein, and green fluorescent protein.

* * * * *

SEQUENCE LISTING

```
<160> NUMBER OF SEQ ID NOS: 34

<210> SEQ ID NO 1
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MCF7-1

<400> SEQUENCE: 1

Asp Met Pro Gly Thr Val Leu Pro Gly Gly
1               5                   10

<210> SEQ ID NO 2
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MCF7-2
```

<400> SEQUENCE: 2

Val Pro Thr Asp Thr Asp Tyr Ser Gly Gly
1               5                   10

<210> SEQ ID NO 3
<211> LENGTH: 29
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: MCF7-1+alpha stand peptide

<400> SEQUENCE: 3

Asp Met Pro Gly Thr Val Leu Pro Gly Gly Gly Gly Ser Glu Gly
1               5                   10                  15

Glu Trp Gln Gln Gln Gln His Gln Trp Ala Lys Gln Glu
            20                  25

<210> SEQ ID NO 4
<211> LENGTH: 272
<212> TYPE: PRT
<213> ORGANISM: Aequorea victoria
<220> FEATURE:
<221> NAME/KEY: PEPTIDE
<222> LOCATION: (1)..(272)

<400> SEQUENCE: 4

Met Ala Ser Met Thr Gly Gly Gln Gln Met Gly Arg Asp Met Pro Gly
1               5                   10                  15

Thr Val Leu Pro Gly Gly Met Ser Lys Gly Glu Glu Leu Phe Thr Gly
                20                  25                  30

Val Val Pro Ile Leu Val Glu Leu Asp Gly Asp Val Asn Gly His Lys
            35                  40                  45

Phe Ser Val Ser Gly Glu Gly Glu Gly Asp Ala Thr Tyr Gly Lys Leu
        50                  55                  60

Thr Leu Lys Phe Ile Ser Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Arg His Asp Phe Phe Lys Ser Ala Met Pro Glu
            100                 105                 110

Gly Tyr Val Gln Glu Arg Thr Ile Ser Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Thr Ala
                165                 170                 175

Asp Lys Gln Arg Asn Gly Ile Lys Ala Asn Phe Lys Thr Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Leu Lys Asp Pro Asn Glu Lys Arg Asp His Met
225                 230                 235                 240

Val Leu Leu Glu Phe Val Thr Ala Ala Gly Ser Gly Ile Thr Asp Glu
            245                 250                 255

Val Asp Gly Thr Glu Leu Tyr Lys Gly Gly His His His His His His
            260                 265                 270

<210> SEQ ID NO 5
<211> LENGTH: 272
<212> TYPE: PRT
<213> ORGANISM: Aequorea victoria
<220> FEATURE:
<221> NAME/KEY: PEPTIDE
<222> LOCATION: (1)..(272)

<400> SEQUENCE: 5

Met Ala Ser Met Thr Gly Gly Gln Gln Met Gly Arg Val Pro Thr Asp
1               5                   10                  15

Thr Asp Tyr Ser Gly Gly Met Ser Lys Gly Glu Glu Leu Phe Thr Gly
            20                  25                  30

Val Val Pro Ile Leu Val Glu Leu Asp Gly Asp Val Asn Gly His Lys
            35                  40                  45

Phe Ser Val Ser Gly Glu Gly Glu Gly Asp Ala Thr Tyr Gly Lys Leu
50                  55                  60

Thr Leu Lys Phe Ile Ser Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
            85                  90                  95

Pro Asp His Met Lys Arg His Asp Phe Phe Lys Ser Ala Met Pro Glu
            100                 105                 110

Gly Tyr Val Gln Glu Arg Thr Ile Ser Phe Asn Asp Asp Gly Asn Tyr
            115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Thr Ala
            165                 170                 175

Asp Lys Gln Arg Asn Gly Ile Lys Ala Asn Phe Lys Thr Arg His Asn
            180                 185                 190

Ile Glu Asp Gly Ser Val Gln Leu Ala Asp His Tyr Gln Gln Asn Thr
            195                 200                 205

Pro Ile Gly Asp Gly Pro Val Leu Leu Pro Asp Asn His Tyr Leu Ser
            210                 215                 220

Thr Gln Ser Ala Leu Leu Lys Asp Pro Asn Asp Lys Arg Asp His Met
225                 230                 235                 240

Val Leu Leu Glu Phe Val Thr Ala Ala Gly Ser Gly Ile Thr Asp Glu
            245                 250                 255

Val Asp Gly Thr Glu Leu Tyr Lys Gly Gly His His His His His His
            260                 265                 270

<210> SEQ ID NO 6
<211> LENGTH: 292
<212> TYPE: PRT
<213> ORGANISM: Aequorea victoria
<220> FEATURE:
<221> NAME/KEY: PEPTIDE
<222> LOCATION: (1)..(292)

<400> SEQUENCE: 6

Met Ala Ser Met Thr Gly Gly Gln Gln Met Gly Arg Asp Met Pro Gly
1               5                   10                  15

Thr Val Leu Pro Gly Gly Gly Ser Glu Gly Glu Trp Gln Gln
            20              25                  30

Gln Gln His Gln Trp Ala Lys Gln Glu Met Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Ser Thr Thr Gly Lys Leu Pro Val
                85                  90                  95

Pro Trp Pro Thr Leu Val Thr Thr Leu Thr Tyr Gly Val Gln Cys Phe
            100                 105                 110

Ser Arg Tyr Pro Asp His Met Lys Arg His Asp Phe Phe Lys Ser Ala
        115                 120                 125

Met Pro Glu Gly Tyr Val Gln Glu Arg Thr Ile Ser Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Thr Ala Asp Lys Gln Arg Asn Gly Ile Lys Ala Asn Phe Lys Thr
        195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Thr Gln Ser Ala Leu Leu Lys Asp Pro Asn Glu Lys Arg
                245                 250                 255

Asp His Met Val Leu Leu Glu Phe Val Thr Ala Ala Gly Ser Gly Ile
            260                 265                 270

Thr Asp Glu Val Asp Gly Thr Cys Glu Leu Tyr Lys Gly Gly His His
        275                 280                 285

His His His His
        290

<210> SEQ ID NO 7
<211> LENGTH: 263
<212> TYPE: PRT
<213> ORGANISM: Aequorea victoria
<220> FEATURE:
<221> NAME/KEY: PEPTIDE
<222> LOCATION: (1)..(263)
<223> OTHER INFORMATION: GFP

<400> SEQUENCE: 7

Met Ala Ser Met Thr Gly Gly Gln Gln Met Gly Arg Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Ser Thr Thr Gly Lys
    50                  55                  60

Leu Pro Val Pro Trp Pro Thr Leu Val Thr Thr Leu Thr Tyr Gly Val
65                  70                  75                  80

Gln Cys Phe Ser Arg Tyr Pro Asp His Met Lys Arg His Asp Phe Phe
                85                  90                  95

Lys Ser Ala Met Pro Glu Gly Tyr Val Gln Glu Arg Thr Ile Ser Phe
            100                 105                 110

Lys Asp Asp Gly Asn Tyr Lys Thr Arg Ala Glu Val Lys Phe Glu Gly
            115                 120                 125

Asp Thr Leu Val Asn Arg Ile Glu Leu Lys Gly Ile Asp Phe Lys Glu
            130                 135                 140

Asp Gly Asn Ile Leu Gly His Lys Leu Glu Tyr Asn Tyr Asn Ser His
145                 150                 155                 160

Asn Val Tyr Ile Thr Ala Asp Lys Gln Lys Asn Gly Ile Lys Ala Asn
                165                 170                 175

Phe Lys Thr Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
            195                 200                 205

Asp Asn His Tyr Leu Ser Thr Gln Ser Ala Leu Leu Lys Asp Pro Asn
210                 215                 220

Glu Lys Arg Asp His Met Val Leu Leu Glu Phe Val Thr Ala Ala Gly
225                 230                 235                 240

Ser Gly Ile Thr Asp Glu Val Asp Gly Thr Cys Glu Leu Tyr Lys Gly
                245                 250                 255

Gly His His His His His
            260

<210> SEQ ID NO 8
<211> LENGTH: 258
<212> TYPE: PRT
<213> ORGANISM: Aequorea victoria
<220> FEATURE:
<221> NAME/KEY: PEPTIDE
<222> LOCATION: (1)..(258)
<223> OTHER INFORMATION: GFP

<400> SEQUENCE: 8

Met Ala Ser Met Thr Gly Gly Gln Gln Met Gly Arg Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
            35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Leu Thr Tyr Gly Val
65                  70                  75                  80

Gln Cys Phe Ser Arg Tyr Pro Asp His Met Lys Arg His Asp Phe Phe
                85                  90                  95

Lys Ser Ala Met Pro Glu Gly Tyr Val Gln Glu Arg Thr Ile Ser Phe
            100                 105                 110

Lys Asp Asp Gly Asn Tyr Lys Thr Arg Ala Glu Val Lys Phe Glu Gly
            115                 120                 125

Asp Thr Leu Val Asn Arg Ile Glu Leu Lys Gly Ile Asp Phe Lys Glu

```
                    130                 135                 140
Asp Gly Asn Ile Leu Gly His Lys Leu Glu Tyr Asn Tyr Asn Ser His
145                 150                 155                 160

Asn Val Tyr Ile Thr Ala Asp Lys Gln Lys Asn Gly Ile Lys Ala Asn
                    165                 170                 175

Phe Lys Thr Arg His Asn Ile Glu Asp Gly Ser Val Gln Leu Ala Asp
                    180                 185                 190

His Tyr Gln Gln Asn Thr Pro Ile Gly Asp Gly Pro Val Leu Leu Pro
                    195                 200                 205

Asp Asn His Tyr Leu Ser Thr Gln Ser Ala Leu Leu Lys Asp Pro Asn
                    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Gly Gly His His His His
                    245                 250                 255

His His

<210> SEQ ID NO 9
<211> LENGTH: 259
<212> TYPE: PRT
<213> ORGANISM: Aequorea victoria
<220> FEATURE:
<221> NAME/KEY: PEPTIDE
<222> LOCATION: (1)..(259)
<223> OTHER INFORMATION: GFP

<400> SEQUENCE: 9

Met Ala Ser Met Thr Gly Gly Gln Gln Met Gly Arg Met Val Ser Lys
1               5                   10                  15

Gly Glu Glu Leu Phe Thr Gly Val Val Pro Ile Leu Val Glu Leu Asp
                20                  25                  30

Gly Asp Val Asn Gly His Lys Phe Ser Val Ser Gly Glu Gly Glu Gly
            35                  40                  45

Asp Ala Thr Tyr Gly Lys Leu Thr Leu Lys Phe Ile Cys Thr Thr Gly
        50                  55                  60

Lys Leu Pro Val Pro Trp Pro Thr Leu Val Thr Thr Leu Thr His Gly
65                  70                  75                  80

Val Gln Cys Phe Ser Arg Tyr Pro Asp His Met Lys Gln His Asp Phe
                85                  90                  95

Phe Lys Ser Ala Met Pro Glu Gly Tyr Val Gln Glu Arg Thr Ile Phe
                100                 105                 110

Phe Lys Asp Asp Gly Asn Tyr Lys Thr Arg Ala Glu Val Lys Phe Glu
                115                 120                 125

Gly Asp Thr Leu Val Asn Arg Ile Glu Leu Lys Gly Ile Asp Phe Lys
            130                 135                 140

Glu Asp Gly Asn Ile Leu Gly His Lys Leu Glu Tyr Asn Phe Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
                180                 185                 190

Asp His Tyr Gln Gln Asn Thr Pro Ile Gly Asp Gly Pro Val Leu Leu
            195                 200                 205

Pro Asp Asn His Tyr Leu Ser Thr Gln Ser Ala Leu Ser Lys Asp Pro
        210                 215                 220
```

```
Asn Glu Lys Arg Asp His Met Val Leu Leu Glu Phe Val Thr Ala Ala
225                 230                 235                 240

Gly Ile Thr Leu Gly Met Asp Glu Leu Tyr Lys Gly Gly His His His
                245                 250                 255

His His His

<210> SEQ ID NO 10
<211> LENGTH: 259
<212> TYPE: PRT
<213> ORGANISM: Aequorea victoria
<220> FEATURE:
<221> NAME/KEY: PEPTIDE
<222> LOCATION: (1)..(259)

<400> SEQUENCE: 10

Met Ala Ser Met Thr Gly Gly Gln Gln Met Gly Arg Met Val Ser Lys
1               5                   10                  15

Gly Glu Glu Leu Phe Thr Gly Val Val Pro Ile Leu Val Glu Leu Asp
                20                  25                  30

Gly Asp Val Asn Gly His Lys Phe Ser Val Ser Gly Glu Gly Glu Gly
            35                  40                  45

Asp Ala Thr Tyr Gly Lys Leu Thr Leu Lys Phe Ile Cys Thr Thr Gly
50                  55                  60

Lys Leu Pro Val Pro Trp Pro Thr Leu Val Thr Thr Phe Gly Tyr Gly
65                  70                  75                  80

Leu Gln Cys Phe Ala Arg Tyr Pro Asp His Met Lys Gln His Asp Phe
                85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Tyr Gln Ser Ala Leu Ser Lys Asp Pro
210                 215                 220

Asn Glu Lys Arg Asp His Met Val Leu Leu Glu Phe Val Thr Ala Ala
225                 230                 235                 240

Gly Ile Thr Leu Gly Met Asp Glu Leu Tyr Lys Gly Gly His His His
                245                 250                 255

His His His

<210> SEQ ID NO 11
<211> LENGTH: 236
<212> TYPE: PRT
<213> ORGANISM: Actinia equina
<220> FEATURE:
<221> NAME/KEY: PEPTIDE
<222> LOCATION: (1)..(236)
<220> FEATURE:
<221> NAME/KEY: PEPTIDE
```

<222> LOCATION: (1)..(236)
<223> OTHER INFORMATION: GFP

<400> SEQUENCE: 11

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
210                 215                 220

Leu Gly Thr Cys Gly Gly His His His His His
225                 230                 235

<210> SEQ ID NO 12
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(45)

<400> SEQUENCE: 12
cctggtactg ttcttcctgg tggtatgagt aaaggagaag aactt            45

<210> SEQ ID NO 13
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: prim_transcript
<222> LOCATION: (1)..(27)
<223> OTHER INFORMATION: Primer

<400> SEQUENCE: 13

```
catatcgcga cccatttgct gtccacc                                           27
```

<210> SEQ ID NO 14
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(45)
<223> OTHER INFORMATION: Primer for MCF7-1

<400> SEQUENCE: 14

```
actgatactg attatagtgg aggaatgagt aaaggagaag aactt                       45
```

<210> SEQ ID NO 15
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(27)
<223> OTHER INFORMATION: Primer for MCF7-1

<400> SEQUENCE: 15

```
aggaacgcga cccatttgct gtccacc                                           27
```

<210> SEQ ID NO 16
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(51)
<223> OTHER INFORMATION: Primer for MCF7-2

<400> SEQUENCE: 16

```
caacaacaac aacatcaatg ggcaaaacaa gaaatgagta aaggagaaga a                51
```

<210> SEQ ID NO 17
<211> LENGTH: 42
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(42)
<223> OTHER INFORMATION: Primer for MCF7-2

<400> SEQUENCE: 17

```
ccattcacct tcactaccac caccaccacc aggaagaaca gt                          42
```

<210> SEQ ID NO 18
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(22)
<223> OTHER INFORMATION: Primer for MCF7-1+alpha stand peptide

<400> SEQUENCE: 18
cattgaagat ggctccgttc aa                                              22

<210> SEQ ID NO 19
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(22)
<223> OTHER INFORMATION: Primer for MCF7-1+alpha stand peptide

<400> SEQUENCE: 19
ttgtggcgag ttttgaagtt ag                                              22

<210> SEQ ID NO 20
<211> LENGTH: 70
<212> TYPE: DNA
<213> ORGANISM: Artificial Sequence
<220> FEATURE:
<223> OTHER INFORMATION: Primer for inverse PCR
<220> FEATURE:
<221> NAME/KEY: prim_transcript
<222> LOCATION: (1)..(70)
<223> OTHER INFORMATION: Primer for inverse PCR

<400> SEQUENCE: 20
ctcgaccata tggctagcat gactggtgga cagcaaatgg gtcgcatgag taaaggagaa     60
gaacttttca                                                            70

<210> SEQ ID NO 21
<211> LENGTH: 54
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(54)
<223> OTHER INFORMATION: Primer for inverse PCR

<400> SEQUENCE: 21
tgacgtgaat tcattagtga tggtgatggt gatgtttgta gagctcatcc atgc           54

<210> SEQ ID NO 22
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(25)
<223> OTHER INFORMATION: Primer for inverse PCR
<220> FEATURE:
<221> NAME/KEY: misc_feature
<222> LOCATION: (13)..(14)
<223> OTHER INFORMATION: n is a, c, g, or t

<400> SEQUENCE: 22
cttaaattta ttnnkactgg aaaac                                           25

<210> SEQ ID NO 23
<211> LENGTH: 20
<212> TYPE: DNA
<213> ORGANISM: Artificial Sequence
<220> FEATURE:

```
<223> OTHER INFORMATION: Primer
<220> FEATURE:
<221> NAME/KEY: prim_transcript
<222> LOCATION: (1)..(20)
<223> OTHER INFORMATION: Primer for inverse PCR

<400> SEQUENCE: 23
ggtaagtttt ccgtatgttg                                               20

<210> SEQ ID NO 24
<211> LENGTH: 26
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(26)
<220> FEATURE:
<221> NAME/KEY: misc_feature
<222> LOCATION: (9)..(10)
<223> OTHER INFORMATION: n is a, c, g, or t

<400> SEQUENCE: 24
gtgttcaann kttttcccgt tatccg                                        26

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(22)

<400> SEQUENCE: 25
catacgtcag agtagtgaca ag                                            22

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(23)

<400> SEQUENCE: 26
tgtcttttca ctggagttgt ccc                                           23

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(21)

<400> SEQUENCE: 27
ttctccttta ctcatttttt c                                             21

<210> SEQ ID NO 28
<211> LENGTH: 24
<212> TYPE: DNA
<213> ORGANISM: Artificial Sequence
```

```
<220> FEATURE:
<223> OTHER INFORMATION: Primer
<220> FEATURE:
<221> NAME/KEY: prim_transcript
<222> LOCATION: (1)..(24)
<223> OTHER INFORMATION: Primer for inverse PCR

<400> SEQUENCE: 28
tgcacacatg gcatggatga gctc                                          24

<210> SEQ ID NO 29
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 29
cccagcagca gttacaaact c                                             21

<210> SEQ ID NO 30
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(33)
<223> OTHER INFORMATION: Primer for inverse PCR

<400> SEQUENCE: 30
cagcgccgtt gtgagctcta caaataatga att                                33

<210> SEQ ID NO 31
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 31
tgtaatccca gcagcagtta c                                             21

<210> SEQ ID NO 32
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 32
acatgtgagc tctacaaata a                                             21

<210> SEQ ID NO 33
<211> LENGTH: 18
<212> TYPE: DNA
```

```
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(18)

<400> SEQUENCE: 33
acggccctgt gtaatccc                                                 18

<210> SEQ ID NO 34
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 34
ggaacatgtg agctctacaa a                                             21
```